US009005617B2

(12) United States Patent
Allison et al.

(10) Patent No.: US 9,005,617 B2
(45) Date of Patent: *Apr. 14, 2015

(54) ANTIKINE ANTIBODIES THAT BIND TO MULTIPLE CC CHEMOKINES

(71) Applicant: Regeneron Pharmaceuticals, Inc., Tarrytown, NY (US)

(72) Inventors: Dan Allison, Lake Forest Park, WA (US); Carol Raport, Bothell, WA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 6 days.

This patent is subject to a terminal disclaimer.

(21) Appl. No.: 13/657,120

(22) Filed: Oct. 22, 2012

(65) Prior Publication Data

US 2013/0108640 A1 May 2, 2013

Related U.S. Application Data

(63) Continuation of application No. 12/870,573, filed on Aug. 27, 2010, now Pat. No. 8,313,747.

(60) Provisional application No. 61/238,015, filed on Aug. 28, 2009.

(51) Int. Cl.
| A61K 39/395 | (2006.01) |
| C07K 16/24 | (2006.01) |
| C07K 16/46 | (2006.01) |

(52) U.S. Cl.
CPC .............. *C07K 16/468* (2013.01); *C07K 16/24* (2013.01); *C07K 2317/24* (2013.01); *C07K 2317/55* (2013.01); *C07K 2317/76* (2013.01); *C07K 2317/33* (2013.01); *C07K 2317/34* (2013.01); *C07K 2317/92* (2013.01)

(58) Field of Classification Search
CPC ........... C07K 2317/33; C07K 2317/34; C07K 2317/92
USPC ................ 424/141.1, 145.1, 1.41; 530/388.1, 530/388.23, 387.3
See application file for complete search history.

(56) References Cited

U.S. PATENT DOCUMENTS

| 5,530,101 | A | 6/1996 | Queen et al. |
| 6,316,420 | B1 | 11/2001 | Karin et al. |
| 6,632,927 | B2 | 10/2003 | Adair et al. |
| 7,482,434 | B2 | 1/2009 | Gudas et al. |
| 2004/0086483 | A1 | 5/2004 | Karin |
| 2006/0057112 | A1 | 3/2006 | Gray et al. |
| 2007/0134236 | A1 | 6/2007 | De Fougerolles et al. |
| 2009/0068173 | A1 | 3/2009 | Proudfoot et al. |
| 2009/0148455 | A1 | 6/2009 | Fischer et al. |
| 2011/0236968 | A1 | 9/2011 | De Fougerolles et al. |

FOREIGN PATENT DOCUMENTS

| JP | H7-509137 A | 10/1995 |
| JP | H7-509137 T | 10/1995 |
| RU | 2339647 C2 | 11/2008 |
| WO | 94/02602 A1 | 2/1994 |
| WO | WO 99/15666 | 4/1999 |
| WO | WO 2004/050836 A2 | 6/2004 |

OTHER PUBLICATIONS

Roitt et al., "Antigen Processing and Presentation", Immunology 6:106-112 (2001).
Official Action from corresponding Russian patent application 2012111820 dated May 30, 2014.
Official Action from corresponding Russian patent application 2012111820 dated May 30, 2014. English Translation.
Extended Search Report issued Feb. 28, 2013 in European Application No. 10812667.3.
Lucy J. Holt, et al., "Domain antibodies: proteins for therapy", Trends in Biotechnology, vol. 21, No. 11, Nov. 2003, pp. 484-490.
Julian Davies, et al., "Affinity improvement of single antibody VH domains: residues in all three hypervariable regions affect antigen binding", Immunotechnology, vol. 2, No. 3, Sep. 1, 1996, pp. 169-179.
Sarah Main, et al., "A Potent Human Anti-Eotaxin1 Antibody, CAT-213: Isolation by Phage Display and in Vitro and in Vivo Efficacy", The Journal of Pharmacology and Experimental Therapeutics, vol. 319, No. 3, Dec. 1, 2006, pp. 1695-1404.
Isabelle Fillion, et al., "Role of Chemokines and Formyl Peptides in Pneumococcal Pneumonia-Induced Monocyte/Macrophage Recruitment", The Journal of Immunology, vol. 166, No. 12, Jun. 1, 2001, pp. 7353-7361.
Michelle L. Scalley-Kim, et al., "A Novel Highly Potent Therapeutic Antibody Neutralizes Multiple Human Chemokines and Mimics Viral Immune Modulation", PLOS ONE, vol. 7, No. 8, Aug. 2012, 14 pages.
International Preliminary Report on Patentability issued Jul. 5, 2012 in PCT/US10/47004 filed Aug. 27, 2010.
Notification of Transmittal of the International Search Report and the Written Opinion of the International Searching Authority or the Declaration issued Jan. 26, 2011 in PCT/US10/47004.
Judy M. Opalek, et al., "Alveolar macrophages lack CCR2 expression and do not migrate to CCL2", Journal of Inflammation, vol. 4, No. 19, 2007, pp. 1-10.
Katrin Ottersbach, et al., "A310 helical turn is essential for the proliferation-inhibiting properties of macrophage inflammatory protein-1-alpha (CCL3)", Blood, vol. 107, No. 4, 2006, pp. 1284-1291 (with an additional page).

(Continued)

*Primary Examiner* — Prema Mertz
(74) *Attorney, Agent, or Firm* — Veronica Mallon; Merchant & Gould PC

(57) ABSTRACT

An antikine antibody binds to two, three, four, five or more CC chemokines, such as RANTES/CCL5, MIP-1α/CCL3, MIP-1β/CCL4, or MCP-1/CCL2. Methods for affinity maturation and humanization of antikine antibodies as well as the production of hybridoma cell lines producing antikine antibodies by sequential immunization are also disclosed.

19 Claims, 14 Drawing Sheets

(56) References Cited

OTHER PUBLICATIONS

Yasuyuki Eda, et al., "Sequential Immunization with V3 Peptides from Primary Human Immunodeficiency Virus Type 1 Produces Cross-Neutralizing Antibodies against Primary Isolates with a Matching Narrow-Neutralization Sequence Motif", Journal of Virology, vol. 80, No. 11, Jun. 2006, pp. 5552-5562.

Cedric Bianpain, et al., "CCR5 Binds Multiple CC-Chokines: MCP-3 Acts as a natural Antagonist", Blood, vol. 94, No. 6, 1999, pp. 1899-1904 (with an additional page).

Written Opinion of the International Preliminary Examining Authority issued on Dec. 7, 2011 in International Patent Application No. PCT/US10/47004 filed on Aug. 27, 2010.

Roitt et al., "Hypervariable sequences in the antigen-binding site allow antibodies to bind a range of antigens", Immunology Fifth Ed, 6:80 (1998).

Japanese Office Action mailed Nov. 11, 2014, for corresponding Japanese Patent Application No. 2012-527033.

Japanese Office Action (English translation) mailed Nov. 11, 2014, for corresponding Japanese Patent Application No. 2012-527033.

Titration of inhibitory activity of purified 3C12F in chemotaxis assays.

Titration of inhibitory activity of purified 7D12A in chemotaxis assays.

Titration of inhibitory activity of purified 7D1G in chemotaxis assays.

Titration of inhibitory activity of purified 18V4F in chemotaxis assays.

Titration of inhibitory activity of purified 18P7E in chemotaxis assays.

Fig. 11A CHEMOKINE BINDING SPECIFICITY OF ANTIKINE ANTIBODY 18V4F (MSD PLATFORM). BACKGROUND BINDING IS INDICATED BY DOTTED LINE.

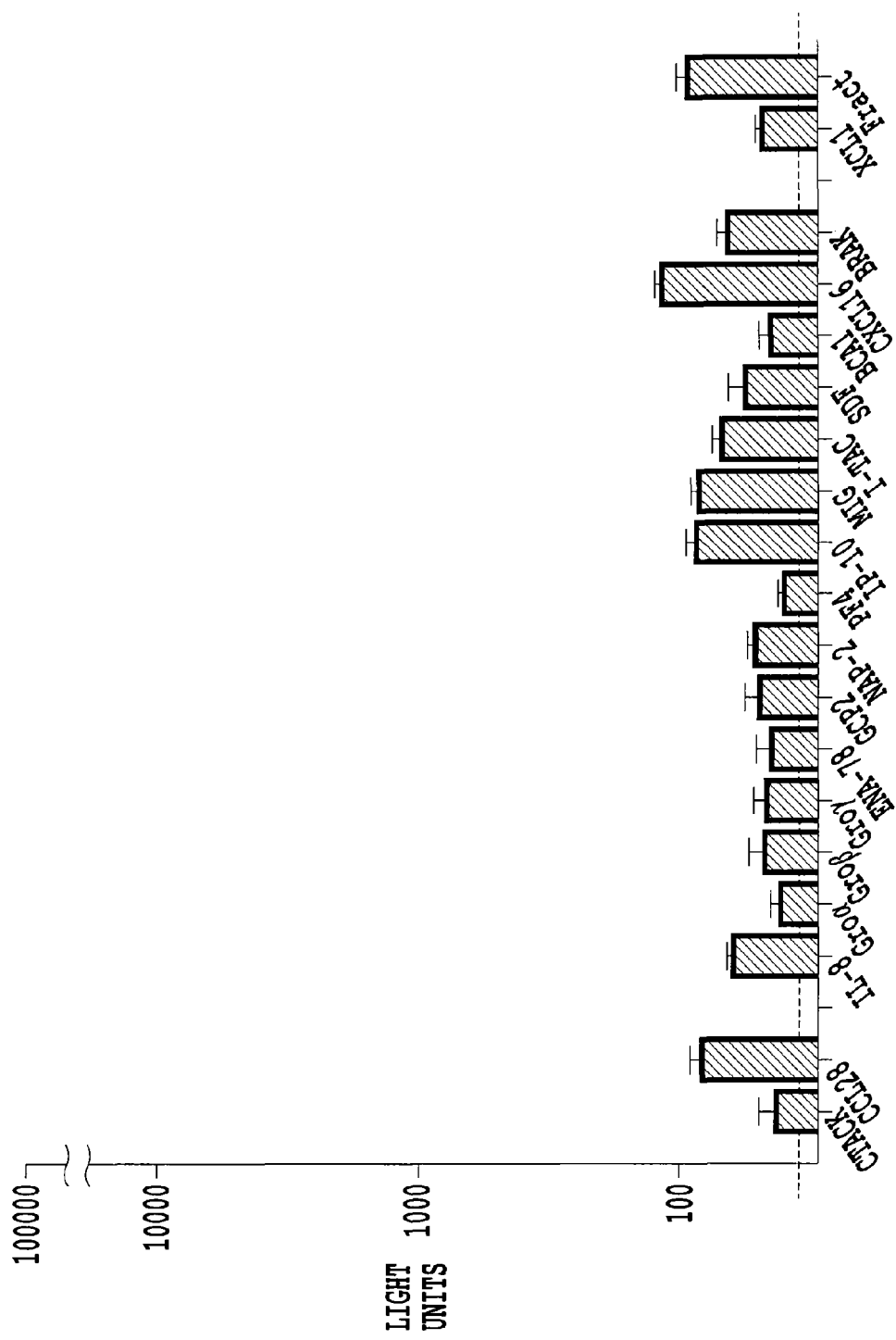
Fig. 11B  CHEMOKINE BINDING SPECIFICITY OF ANTIKINE ANTIBODY 18V4F (MSD PLATFORM). BACKGROUND BINDING IS INDICATED BY DOTTED LINE.

CHEMOKINE BINDING SPECIFICITY OF ANTIKINE ANTIBODY 18P7E (MSD PLATFORM). BACKGROUND BINDING IS INDICATED BY DOTTED LINE

Alignment of amino acid sequences of CC-chemokines bound by MAb3C12F

```
              1           10         20         30         40         50         60          77
MIP-1a   (1) ASLAADTPTACCFSYTSRQIPQNFIADYFETSSQCSKPGVIFLTKRSRQVCADPSEEWVQKYVSDLELSA----------
RANTES   (1) -SPYSSDTTPCCFAYIARPLPRAHIKEYFYTSGKCSNPAVVFVTRKNRQVCANPEKKWVREYINSLEMS----------
MIP-1b   (1) APMGSDPPTACCFSYTARKLPHNFVVDYYETSSLCSQPAVVFQTKRGKQVCADPSESWVQEYVYDLELN----------
MPIF-1   (1) --RFHATSADCCISYTPRSIPCSLLESVFETNSECSKPGVIFLTKKGRRFCANPSDKQVQVCMRMLKLDTRIKTRKN
HCC-2    (1) ---SFHFAADCCTSYISQSIPCSLMKSYFETSSECSKPGVIFLTKKGRQVIFLTKKGRQVCADPSEEWVQKYVSDLELSA
```

Fig. 13A

Alignment of amino acid sequences of CC-chemokines bound by MAb7D12A

```
              1           10         20         30         40         50         60          77
MIP-1a   (1) ASLAADTPTACCFSYTSRQIPQNFIADYFETSSQCSKPGVIFLTKRSRQVCADPSEEWVQKYVSDLELSA----------
RANTES   (1) -SPYSSDTTPCCFAYIARPLPRAHIKEYFYTSGKCSNPAVVFVTRKNRQVCANPEKKWVREYINSLEMS----------
MIP-1b   (1) APMGSDPPTACCFSYTARKLPHNFVVDYYETSSLCSQPAVVFQTKRGKQVCADPSESWVQEYVYDLELN----------
MPIF-1   (1) --RFHATSADCCISYTPRSIPCSLLESVFETNSECSKPGVIFLTKKGRRFCANPSDKQVQVCMRMLKLDTRIKTRKN
```

Fig. 13B

Alignment of amino acid sequences of CC-chemokines bound by MAb7D1G

```
              1         10        20        30        40        50        60        70    77
MIP-1a   (1) ASLAADTPTACCFSYTSRQIPQNFIADYFETSSQCSKPGVIFLTKRSRQVCADPSEEWVQKYVSDLELSA-------
RANTES   (1) -SPYSSDTTPCCFAYIARPLPRAHIKEYFYTSGKCSNPAVVFVTRKNRQVCANPEKKWVREYINSLEMS-------
MIP-1b   (1) APMGSDPPTACCFSYTARKLPHNFVVDYYETSSLCSQPAVVFQTKRGKQVCADPSESWVQEYVYDLELN-------
HCC-1    (1) ---GPYHPSECCFTVTTYKIPRQRIMDYYETNSQCSKPGIVFITKRGHSVCTNPSDKWVQDYIKDMKEN-------
MPIF-1   (1) --RFHATSADCCISYTPRSIPCSLLESVFETLSEGCSKPGVIFLTKKGRRFCANPSDKQVQVCMRMLKLDTRIKTRKN
PARC     (1) -AQVGTNKELCCLVVTSWQIPQKFIVDYSEISPQCPKPGVILLTKRGRQICADPNKKWVWQKYISDLKLNA------
```

Fig. 13C

Alignment of amino acid sequences of CC-chemokines bound by MAb18V4F

```
              1         10        20        30        40        50        60
MIP-1a   (1) ASLAADTPTACCFSYTSRQIPQNFIADYFETSSQCSKPGVIFLTKRSRQVCADPSEEWVQKYVSDLELSA-
RANTES   (1) -SPYSSDTTPCCFAYIARPLPRAHIKEYFYTSGKCSNPAVVFVTRKNRQVCANPEKKWVREYINSLEMS--
MIP-1b   (1) APMGSDPPTACCFSYTARKLPHNFVVDYYETSSLCSQPAVVFQTKRGKQVCADPSESWVQEVVYDLELN--
```

Fig. 13D

ANTIKINE ANTIBODIES THAT BIND TO MULTIPLE CC CHEMOKINES

CROSS-REFERENCE TO RELATED APPLICATION(S)

This application is a continuation of U.S. application Ser. No. 12/870,573, filed Aug. 27, 2010, now U.S. Patent No. 8,313,747, issued Nov. 20, 2012, and claims priority under 35 U.S.C. 119(e) to U.S. Provisional Application 61/238,015, filed Aug. 28, 2009. Each of these applications is hereby incorporated by reference in its entirety.

BACKGROUND OF THE INVENTION

1. Field of the Invention

The invention encompasses antikine antibodies, or antibodies that bind to two, three, four, five, or more CC chemokines (CC chemokines are also known as β-chemokines), particularly those antibodies which bind to at least two chemokines selected from the group consisting of RANTES/CCL5, MIP-1α/CCL3, MIP-1β/CCL4, and MCP-1/CCL2. Unlike antibodies that bind to only a single CC chemokine, antikine antibodies practically address the problem of functional redundancy amongst CC chemokines by binding to, detecting, and/or neutralizing more than one CC chemokine at a time. Other aspects of the invention include diagnostic and therapeutic uses of antikine antibodies including the treatment of conditions, disorders, or diseases mediated by CC chemokines; hybridoma cell lines producing antikine antibodies and methods for producing hybridomas by sequential immunization; methods for humanizing antikine antibodies; and methods for improving antikine antibodies by affinity maturation.

2. Description of the Related Art

Chemokines are key mediators of inflammation and are implicated in the development of autoimmune disease; Viola & Luster, Ann. Rev. Pharmacol. Toxicol. 48: 171-197 (2008). They are produced at sites of inflammation or infection and induce the migration of leukocytes from the circulation into the tissue. Simple and effective ways for modulating inflammation or immunological processes mediated by chemokines have long been sought. These efforts are complicated by the redundancy and overlap in the functions of numerous different chemokines and their receptors. For example, chemokine inhibitors have been used to treat autoimmune conditions in preclinical animal models, but have yet to succeed in the clinic for treating autoimmune indications. It has been proposed that this lack of efficacy may be due to the redundancy in the functions of chemokines. Over 50 different chemokines have been identified and each has different structural and functional properties. The specificity of some chemokines overlap, that is, they bind to the same type of receptor or act on similar types of cells; Vergunst, et al., Arthritis Rheum. 58: 1931-1939 (2008). A particular chemokine may bind to more than one type of chemokine receptor and a given chemokine receptor may be bound by more than one type of chemokine. Therefore, the development of a single agent capable of binding to, blocking chemokine binding to a receptor, or otherwise neutralizing the activity of more than one chemokine is highly desirable.

Chemokines which take their name from chemotactic cytokines, are small secreted polypeptides that regulate movement of immune cells into tissues; Baggiolini, et al., Adv. Immunol. 55:97-179 (1994); Oppenheim et al., Ann. Rev. Immunol. 9:617-648 (1991).

All chemokines share a Greek key structure that is stabilized by disulfide bonds between conserved cysteine residues. However, chemokines are further assigned to four different families based on the number and position of these conserved cysteine residues. The α- and β-chemokines each contain four conserved cysteine residues. The first two cysteines of an α-chemokine are separated by a single amino acid, thus forming a characteristic CXC amino acid motif. The first two conserved cysteines of a β-chemokine are adjacent. Thus, the β-chemokines are also known as CC chemokines. By contrast, lymphotactin is the sole member of a third class of XC chemokines and contains only the second and fourth conserved cysteine residues. A fourth class of chemokines, of which fractalkine is the sole member, is the CXXXC or $CX_3C$ class which has 3 amino acids separating the first two conserved cysteines. In humans, α-chemokines are mainly encoded by genes clustered on chromosome 4 and β-chemokines are mainly encoded by genes on chromosome 17. Lymphotactin is encoded on chromosome 1 and fractalkine on chromosome 16.

Chemokines form gradients that serve as chemoattractants and potential proliferation signals for immune and other cells such as monocytes, macrophages, basophils, eosinophils, T lymphocytes and fibroblasts. CC chemokines exhibit chemoattractant properties by forming concentration gradients recognized by chemotactic cells; CC chemokines also signal particular cell types to proliferate, including fibroblasts and immune cells such as monocytes, macrophages, T lymphocytes, basophils, and eosinophils. The target receptors and cells of chemokines, including CC chemokines are described by Viola, et al., Annu Rev. Pharmacol. Toxicol. 48:171-197 (2008), see e.g., FIG. 1, which document is hereby incorporated by reference for its teachings regarding CC chemokine chemoattractant and signaling functions.

Chemokines share structural features associated with particular chemokine functions, such as with binding to a chemokine receptor. Common structures include an elongated N-terminus segment (N terminal domain) that precedes the first cysteine residue, N loop, $3_{10}$ helix, beta strands β1, β2, and β3, the 30's, 40's and 50s loops; location of disulfide bonds, and the C-terminal α-helical segment.

These and other CC chemokine structures, including conserved or homologous amino acid residues among different CC chemokines, as well as the solvent-accessible, partially solvent accessible, and buried amino acid residues of CC chemokines are incorporated by reference Fernandez, et al., Annu. Rev. Pharmacol. Toxicol. 42:469-99 (2002), see e.g., FIGS. 1 and 2. Buried amino acid residues of intact, undenatured chemokines are unlikely to form epitopes or antigenic determinants contacted by antibodies to a chemokine. In contrast, solvent or surface-exposed CC chemokine residues are more accessible to antibody binding.

CC chemokine residues associated with chemokine receptor binding of CCL3/MIP-1α include residues 11-15 (CCFSY), residues 17-24 (SRQIPQNF), residues 34-35 (QC), and residues 57-67 (EWVQKYVSDLE) of SEQ ID NO: 71;

residues associated with CCL4/MIP-1β chemokine receptor binding include residues 11-15 (CCFSY), residues 17-24 (ARKLPHNF), residues 34-35 (LC), or residues 57-67 (SWVQEYVYDLE) of SEQ ID NO: 72;

residues associated with CCL5/RANTES binding include residues 10-14 (CCFAY), residues 16-23 (ARPLPRAH), residues 33-34 (KC), or residues 56-66 (KWVREYINSLE) of SEQ ID NO: 73;

residues associated with CCL23/MPIF-1 binding include residues 9-13 (CCISY), residues 15-22 (PRSIPCSL), residues 32-33 (EC), or residues 55-65 (KQVQVCMRMLK) of SEQ ID NO: 81; and residues associated with CCL15/HCC-2 include residues 8-12 (CCTSY), residues 14-21 (SQSIPCSL), residues 31-32 (EC), or residues 54-64 (PGVQDCMKKLK) of SEQ ID NO: 79. Corresponding amino acid residues of other CC chemokines are depicted, for example, by FIG. 1 of Fernandez, et al., id. (2002).

Conserved domains for CC chemokines are disclosed at http://www.ncbi.nlm.nih.gov/. This structural data is incorporated by reference to the protein and conserved domain database information at the website named above as last accessed Aug. 24, 2010.

Chemokines in the CC chemokine class interact with seven transmembrane G-protein coupled receptors termed CC chemokine receptors or CCRs, Rossi & Zlotnik, Ann. Rev. Immunol. 18:217-242 (2002). Interaction of the chemokine with its receptor regulates activation of adhesion molecules and affects diapedesis and extravasation of immune cells from the circulation into tissues.

Chemokines have been implicated in the development and maintenance of numerous inflammatory and immunological conditions, disorders and diseases. These include rheumatoid arthritis, multiple sclerosis, atherosclerosis, psoriasis, inflammatory bowel disease (including Crohn's disease, ulcerative colitis, Celiac disease), vascular restenosis, lupus nephritis, glomerulonephritis, transplant rejection, scleroderma, fibrotic disease, asthma (and other lung inflammatory conditions). For example, levels of CC-chemokines are elevated in affected tissues from patients with rheumatoid arthritis, multiple sclerosis (MS), atherosclerosis, and others. Preclinical animal models of these diseases show that inhibition of individual chemokines can at least partially ameliorate disease symptoms. For example, Kasama, et al., J. Clin. Invest. 95: 2868-2876 (1995) demonstrated that administration of an antibody which inhibited MIP-1α/CCL3 could reduce arthritis clinical scores by approximately 50% in a rodent model of rheumatoid arthritis. Similarly, Ogata, et al., J. Pathol. 182: 106-114 (1997) showed that an anti-MCP-1/CCL2 antibody could decrease joint swelling by approximately 30%. Receptors for MIP-1α/CCL3 (including CCR1 and CCR5) and MCP-1/CCL2 (CCR2) are expressed in an overlapping pattern in leukocytes, and thus it is possible that an inhibitor of both MIP-1α/CCL3 and MCP-1/CCL2 could be more efficacious than individual inhibitors of each chemokine alone. Viola, et al., Annu. Rev. Pharmacol. Toxicol. 48:171-197 (2008), is hereby incorporated by reference for its disclosure of specific classes or types of diseases and disorders associated with or mediated by such CC chemokines, see e.g., Table 1.

Natural inhibitors of chemokine activity are known and specific agents, such as antibodies or small molecule inhibitors that bind to or interfere with the activity of particular chemokines have been developed, see Fernandez, et al., Annu. Rev. Pharmacol. Toxicol. 42: 469-99 (2002), to which such inhibitors and agents are incorporated by reference, see e.g., pages 482-488. Vaccinia and related pox viruses produce a soluble 35 kD protein termed vCCI (SEQ ID NO: 117) which binds and inhibits multiple chemokines within the CC class of chemokines. The CC class of chemokines generally acts upon leukocytes including T cells and monocytes; Smith et al., Virology 236: 316-327 (1997), Burns et al., J. Biol. Chem. 277: 2785-2789 (2002). Recombinant vCCI has been shown to be effective in reducing leukocyte infiltration in several models of chronic inflammatory disease, including experimental autoimmune encephalitis; Jones et al., Cytokine 43: 220-228 (2008) and asthma; Dabbagh, et al., J. Immunol. 165: 3418-3422 (2000). However, use of natural substances such as viral proteins like vCCI foreign to a subject's immune system raises safety issues. Administration of substances, such as vCCI can induce undesired physiological or immune responses and such substances can be neutralized, removed or destroyed as foreign by host clearance or defense mechanisms.

With this in mind, the inventors focused on developing a method for producing antibodies, especially humanized antibodies, that can specifically bind to and neutralize more than one chemokine, but which do not pose the risks associated with molecules like vCCI. Prior art chemokine inhibitors, such as antibodies that bind to a single CC chemokine suffer from the problem of CC chemokine receptor redundancy. For example, CCL3/MIP-1α and CCL5/RANTES each bind to chemokine receptors 1 (CCR1) and 5 (CCR5), see FIG. 1 of Viola, id. (2008). An antibody that only inhibits CCL3 binding to these chemokine receptors wouldn't prevent receptor activation by the binding of other CC chemokines, such as CCL5.

The inventors initially targeted CC chemokines MIP-1α/CCL3, MIP-1β/CCL4 and RANTES/CCL5, which constitute the primary ligands for chemokine receptors CCR1 and CCR5. CCL2/MCP-1 was also targeted as a ligand for CCR2. As shown by FIG. 1 of Viola, et al., id. (2008), these receptors are broadly expressed on monocytes and T cells, as well as on other leukocyte subsets. They are implicated in numerous inflammatory disease states both in preclinical animal models of disease and in human disease.

BRIEF DESCRIPTION OF THE INVENTION

One aspect of the invention is an isolated antikine antibody or antigen binding fragment thereof that can bind to at least two, three, four, five, six or seven or more different CC chemokines. One example of an antikine antibody is one that can bind to two or more CC chemokines, including at least one CC chemokine that interacts with chemokine receptor CCR1, CCR2, CCR3, CCR4, CCR5, CCR6, CCR7, CCR8, CCR9 or CCR10. In another embodiment, an antikine will bind to at least two or three of CCL3/MIP-1α, CCL4/MIP-1β, CCL5/RANTES, and CCL2/MCP-1 which interact with CCR1, CCR2 and CCR5. Other examples of an antikine antibody or antigen binding fragment of an antikine antibody include those binding to at least three different CC chemokines selected from the group consisting of CCL2/MCP-1, CCL3/MIP-1α, CCL4/MIP-1β, CCL5/RANTES, CCL14/HCC-1, CCL15/HCC-2, CCL18/PARC, and CCL23/MPIF-1.

Binding occurs via contact between the antikine antibody and at least one determinant of the CC chemokine. For example, binding may occur between the antibody and a determinant of CCL2/MCP-1, CCL3/MIP-1α, CCL4/MIP-1β, CCL5/RANTES, CCL14/HCC-1, CCL15/HCC-2, CCL18/PARC, or CCL23/MPIF-1 that is located between the CC residues of the CC-chemokine and the last C residue of the CC chemokine. The location of the adjacent CC (cysteine-cysteine) residues and the last cysteine residue in CC chemokines is well known in the art and may be easily identified in the sequences of CC chemokines shown in the sequence listing.

Antikine antibodies and their antigen binding fragments can also bind to at least one determinant of a CC chemokine, including CCL2/MCP-1, CCL3/MIP-1α, CCL4/MIP-1β, CCL5/RANTES, CCL14/HCC-1, CCL15/HCC-2, CCL18/

PARC, and CCL23/MPIF-1, which is located in the N-loop, 30's loop, or 40's loop of said CC chemokine.

An antikine antibody may also be characterized by its ability to bind to some CC chemokines but not to others. For example, an antikine antibody may bind to CCL3/MIP-1α and CCL4/MIP-1β, but not bind to CCL5/RANTES, CCL2/MCP-1, CCL8/MCP-2 or CCL7/MCP-3. Others will not bind to some or all of the chemokines and other biologically active molecules named in the figures including MIP-1α, MIP-1β, RANTES, MPIF-1, HCC-1, HCC-2, HCC-4, Parc, MCP-2, MCP-3, MCP-4, Eotaxin, MDC, ELC, 1-309, IL-8, SDF or Fractalkine, as well as to other chemokines. For example, antikines which do not bind to at least one of MCP-1, MCP-2 or MCP-3 are exemplified herein.

An antikine may also be characterized by an ability to bind to two or more CC chemokine of one species, but not to a corresponding CC chemokine of another species. For example, an antikine may bind to human CCL3, but not substantially bind to murine CCL3. Specific examples of binding specificity of antikine antibodies appear in FIGS. 8-12.

Some antikine antibodies and their antigen-binding fragments can also inhibit the interaction of a CC chemokine with a corresponding receptor. Such inhibition may have functional effects, such as inhibiting chemotaxis or other effects activated by chemokine binding to a receptor.

The antikine antibody may bind to at least one determinant within CC receptor binding residues of a CC chemokine. Receptor binding amino acid residues and segments of CC chemokines thought or known to be associated with CC chemokine receptor binding are documented in the art.

The N-terminus, N-loop, 30s-loop, and residues next to the disulfides and in the alpha helix are thought to be involved in receptor binding for the CC chemokine family in general. Description of particular structural features of chemokines that correlate to their various functions is incorporated by reference to the following two publications. Baysal, et al., Proteins 43(2):150-60 (2001) and Kuloglu, et al., Biochemistry, 40(42):12486-96 (2001). See NCBI Conserved Domain Database CDD 29111 for the proposed functional domains of CC chemokines.

The inventors have produced and identified specific antikine monoclonal antibodies 3C12F, 7D1G, 7D12A, 18V4F and 18P7E. These antikines may be used to identify other antibodies or substances that competitively block the binding of these antikine monoclonal antibodies to one or more of the CC chemokines they recognized using competitive inhibition assays known in the art. Competitive inhibitors, such as antibodies that inhibit antikine antibody binding are also encompassed by the invention as well as methods of detecting such competitive inhibitors using antikine monoclonal antibodies 3C12F, 7D1G, 7D12A, 18V4F and 18P7E.

Antikine antibodies may be human antibodies, humanized antibodies, chimeric human-murine antibodies, murine or other vertebrate, avian or mammalian antibodies, or their antigen binding fragments.

One type of antikine antibody of the invention has binding specificities identical or similar to that of monoclonal antibody 3C12F and can bind to at least two, three, four or five CC chemokines selected from the group consisting of CCL3/MIP-1α, CCL4/MIP-1β, CCL5/RANTES, CCL15/HCC-2, and CCL23/MPIF-1. These may exhibit no or substantially no binding to other chemokines, including other chemokines shown in FIG. 8, such as HCC-1, PARC, or MCP 1, 2 or 3. Antibodies of this type may bind to domains which may be important in binding to chemokine receptors, including:

a determinant in the N loop, 30s loop, or 40's loop of a CC chemokine;

at least one antigenic determinant of CCL3/MIP-1α located within residues 11-15 (CCFSY), residues 17-24 (SRQIPQNF), residues 34-35 (QC), or residues 57-67 (EWVQKYVSDLE) of SEQ ID NO: 71;

at least one antigenic determinant of CCL4/MIP-1β located within residues 11-15 (CCFSY), residues 17-24 (ARKLPHNF), residues 34-35 (LC), or residues 57-67 (SWVQEYVYDLE) of SEQ ID NO: 72;

at least one antigenic determinant of CCL5/RANTES located within residues 10-14 (CCFAY), residues 16-23 (ARPLPRAH), residues 33-34 (KC), or residues 56-66 (KWVREYINSLE) of SEQ ID NO: 73;

at least one antigenic determinant of CCL23/MPIF-1 located within residues 9-13 (CCISY), residues 15-22 (PRSIPCSL), residues 32-33 (EC), or residues 55-65 (KQVQVCMRMLK) of SEQ ID NO: 81; or at least one antigenic determinant of CCL15/HCC-2 located within residues 8-12 (CCTSY), residues 14-21 (SQSIPCSL), residues 31-32 (EC), or residues 54-64 (PGVQDCMKKLK) of SEQ ID NO: 79.

This type of antibody may comprise at least one complementarity determining region (CDR) of MAb 3C12F selected from the group consisting of SEQ ID NOS: 3, 4, 5, 8, 9 or 10, or SEQ ID NOS: 53, 54, 55, 58, 59 or 60 or at least one CDR of an antibody that competitively inhibits or blocks the binding of MAb 3C12F to the CC chemokines it binds or blocks binding of RANTES to vCCI (see FIG. 2). An antikine antibody of this type may contain 1, 2, 3, 4, 5 or 6 CDRs of MAb 3C12F or CDRs in which 1, 2, 3, 4, 5, 6, 7, 8 or more amino acid residues of SEQ ID NOS: 3, 4, 5, 8, 9 and/or 10, or SEQ ID NOS: 53, 54, 55, 58, 59 and/or 60 have been deleted, inserted or substituted. Thus, CDR sequences may be identical to those of an antibody produced by hybridoma cell line 3C12F or by a subculture thereof; may correspond to those of an antikine antibody analog of 3C12F, or correspond to those of an antikine monoclonal antibody that competitively blocks or inhibits the binding of MAb 3C12F to two or more of the CC chemokines to which it binds. Such antibodies may be in the form of a human antibody, a humanized antibody, a chimeric human-murine antibody, murine, avian or other vertebrate antibody; or an antigen binding fragment thereof.

A second type of antibody has a binding specificity that is similar or identical to 7D1G, and binds to at least two, three, four, five or six CC chemokines selected from the group consisting CCL3/MIP-1α, CCL4/MIP-1β, CCL5/RANTES, CCL14/HCC-1, CCL23/MPIF-1, and CCL18/PARC. This type of antibody may exhibit no or substantially no binding to other chemokines, such as the other chemokines shown in FIG. 10, such as FICC-2, Eotaxin, or MCP 1, 2, 3 or 4.

Antibodies of this second type may bind to structural determinants of a chemokine or CC chemokine, including to a determinant in the N loop or 40's loop of at least one of the CC chemokines bound by MAb 7D1G;

at least one antigenic determinant of CCL3/MIP-1α located within residues 11-15 (CCFSY), residues 17-24 (SRQIPQNF), residues 34-35 (QC), or residues 57-67 (EWVQKYVSDLE) of SEQ ID NO: 71;

at least one antigenic determinant of CCL4/MIP-1β located within residues 11-15 (CCFSY), residues 17-24 (ARKLPHNF), residues 34-35 (LC), or residues 57-67 (SWVQEYVYDLE) of SEQ ID NO: 72;

at least one antigenic determinant of CCL5/RANTES located within residues 10-14 (CCFAY), residues 16-23 (ARPLPRAH), residues 33-34 (KC), or residues 56-66 (KWVREYINSLE) of SEQ ID NO: 73;

at least one antigenic determinant of CCL23/MPIF-1 located within residues 9-13 (CCISY), residues 15-22 (PRSIPCSL), residues 32-33 (EC), or residues 55-65 (KQVQVCMRMLK) of SEQ ID NO: 81;

at least one antigenic determinant of CCL14/HCC-1 residues 8-12 (CCFTY), residues 14-21 (TYKIPRQR), residues 31-32 (QC), or residues 54-64 (KWVQDYIKDMK) of SEQ ID NO: 78; or at least one antigenic determinant of CCL18/PARC residues 10-14 (CCLVY), residues 16-23 (SWQIPQKF), residues 33-34 (QC), or residues 56-66 (KWVQKYISDLK) of SEQ ID NO: 82.

Structurally, these antibodies may comprise one or more CDRs of MAb 7D1G, selected from the group consisting of SEQ ID NOS: 23, 24, 25, 28, 29 or 30, or a CDR from an antibody that competitively inhibits or blocks the binding of MAb 7D1G to the CC chemokines it binds. One kind of an antikine antibody of this type will contain 1, 2, 3, 4, 5 or 6 CDRs of MAb 7D1G or CDRs in which 1, 2, 3, 4, 5, 6, 7, 8 or more amino acid residues of SEQ ID NOS: 23, 24, 25, 28, 29 and/or 30 have been deleted, inserted or substituted. Thus, CDR sequences may be identical to those of an antibody produced by hybridoma cell line 7D1G or by a subculture thereof; may correspond to those of an antikine antibody analog of 7D1G, or correspond to those of an antikine monoclonal antibody that competitively blocks or inhibits the binding of MAb 7D1G to two or more of the CC chemokines to which it binds. Such antibodies may be in the form of a human antibody, a humanized antibody, a chimeric human-murine antibody, murine, avian or other vertebrate antibody; or an antigen binding fragment thereof.

A third type of antikine antibody has a binding specificity similar or identical to 7D12A and binds to at least two, three or four CC chemokines selected from the group consisting of CCL3/MIP-1α, CCL4/MIP-1β, CCL5/RANTES, and CCL23/MPIF-1. These may exhibit no or substantially no binding to other chemokines, including other chemokines shown in FIG. 9, such as CCL2/MCP-1.

Such an antibody product may bind to a determinant in the N loop or 40's loop of at least one of said CC chemokines; may bind to at least one antigenic determinant of CCL3/MIP-1α located within residues 11-15 (CCFSY), residues 17-24 (SRQIPQNF), residues 34-35 (QC), or residues 57-67 (EWVQKYVSDLE) of SEQ ID NO: 71;

at least one antigenic determinant of CCL4/MIP-1β located within residues 11-15 (CCFSY), residues 17-24 (ARKLPHNF), residues 34-35 (LC), or residues 57-67 (SWVQEYVYDLE) of SEQ ID NO: 72;

at least one antigenic determinant of CCL5/RANTES located within residues 10-14 (CCFAY), residues 16-23 (ARPLPRAH), residues 33-34 (KC), or residues 56-66 (KWVREYINSLE) of SEQ ID NO: 73; or at least one antigenic determinant of CCL23/MPIF-1 residues 9-13 (CCISY), residues 15-22 (PRSIPCSL), residues 32-33 (EC), or residues 55-65 (KQVQVCMRMLK) of SEQ ID NO: 81.

Structurally these third type antibodies may comprise at least one CDR of MAb 7D12A selected from the group consisting of SEQ ID NOS: 13, 14, 15, 18, 19 or 20, or at least one CDR from an antibody that competitively inhibits the binding of MAb 7D12A to CC chemokines it binds. An antikine antibody of this type may contain 1, 2, 3, 4, 5 or 6 CDRs of MAb 7D12A or CDRs in which 1, 2, 3, 4, 5, 6, 7, 8 or more amino acid residues of SEQ ID NOS: 13, 14, 15, 18, 19 and/or 20, have been deleted, inserted or substituted. Thus, CDR sequences may be identical to those of an antibody produced by hybridoma cell line 7D12A or by a subculture thereof; may correspond to those of an antikine antibody analog of 7D12A, or correspond to those of an antikine monoclonal antibody that competitively blocks or inhibits the binding of MAb 7D12A to two or more of the CC chemokines to which it binds. Such antibodies may be in the form of a human antibody, a humanized antibody, a chimeric human-murine antibody, murine, avian or other vertebrate antibody; or an antigen binding fragment thereof.

A fourth type of antikine antibody has a binding specificity similar or identical to 18V4F and binds to at least two or three CC chemokines selected from the group consisting of CCL3/MIP-1α, CCL4/MIP-1β, and CCL5/RANTES. These may exhibit no or substantially no binding to other chemokines, including other chemokines shown in FIG. 11, such as CCL2/MCP-1. Such an antibody product may bind to a determinant in the N loop or 40's loop of at least one of said CC chemokines; may bind to at least one antigenic determinant of CCL3/MIP-1α located within residues 11-15 (CCFSY), residues 17-24 (SRQIPQNF), residues 34-35 (QC), or residues 57-67 (EWVQKYVSDLE) of SEQ ID NO: 71;

at least one antigenic determinant of CCL4/MIP-1β located within residues 11-15 (CCFSY), residues 17-24 (ARKLPHNF), residues 34-35 (LC), or residues 57-67 (SWVQEYVYDLE) of SEQ ID NO: 72;

at least one antigenic determinant of CCL5/RANTES located within residues 10-14 (CCFAY), residues 16-23 (ARPLPRAH), residues 33-34 (KC), or residues 56-66 (KWVREYINSLE) of SEQ ID NO: 73.

Structurally this fourth type of antibody may comprise at least one CDR of MAb 18V4F selected from the group consisting of SEQ ID NOS: 33, 34, 35, 38, 39, or 40 or SEQ ID NOS: 63, 64, 65, 68, 69 or 70, or at least one CDR from an antibody that competitively inhibits the binding of MAb 18V4F to CC chemokines it binds. An antikine antibody of this type may contain 1, 2, 3, 4, 5 or 6 CDRs of MAb 18V4F or CDRs in which 1, 2, 3, 4, 5, 6, 7, 8, or more amino acid residues of 33, 34, 35, 38, 39 and/or 40; or SEQ ID NOS: 63, 64, 65, 68, 69 and/or 70 have been deleted, inserted or substituted with other amino acid residues. Thus, CDR sequences may be identical to those of an antibody produced by hybridoma cell line 18V4F or by a subculture thereof; may correspond to those of an antikine antibody analog of 18V4F, or correspond to those of an antikine monoclonal antibody that competitively blocks or inhibits the binding of MAb 18V4F to two or more of the CC chemokines to which it binds. Such antibodies may be in the form of a human antibody, a humanized antibody, a chimeric human-murine antibody, murine, avian or other vertebrate antibody; or an antigen binding fragment thereof.

A fifth type of antikine antibody has a binding specificity similar or identical to 18P7E and binds to at least two, or three CC chemokines selected from the group consisting of CCL3/MIP-1α, CCL4/MIP-1β, and CCL5/RANTES. These may exhibit no or substantially no binding to other chemokines, including other chemokines shown in FIG. 12, such as CCL2/MCP-1. Such an antibody product may bind to a determinant in the N loop or 40's loop of at least one of the three CC chemokines mentioned above.

Such an antibody product may bind to a determinant in the N loop or 40's loop of at least one of said CC chemokines; may bind to at least one antigenic determinant of CCL3/MIP-1α located within residues 11-15 (CCFSY), residues 17-24 (SRQIPQNF), residues 34-35 (QC), or residues 57-67 (EWVQKYVSDLE) of SEQ ID NO: 71;

at least one antigenic determinant of CCL4/MIP-1β located within residues 11-15 (CCFSY), residues 17-24

(ARKLPHNF), residues 34-35 (LC), or residues 57-67 (SWVQEYVYDLE) of SEQ ID NO: 72;

at least one antigenic determinant of CCL5/RANTES located within residues 10-14 (CCFAY), residues 16-23 (AR-PLPRAH), residues 33-34 (KC), or residues 56-66 (KWVREYINSLE) of SEQ ID NO: 73.

Structurally this fifth type of antibody may comprise at least one CDR of MAb 18P7E selected from the group consisting of SEQ ID NOS: 43, 44, 45, 48, 49 or 50, or at least one CDR from an antibody that competitively inhibits the binding of MAb 18P7E to CC chemokines it binds. An antikine antibody of this type may contain 1, 2, 3, 4, 5 or 6 CDRs of MAb 18P7E or CDRs in which 1, 2, 3, 4, 5, 6, 7, 8 or more amino acid residues of ID NOS: 43, 44, 45, 48, 49 and/or 50 have been deleted, inserted or substituted with other amino acids. Thus, CDR sequences may be identical to those of an antibody produced by hybridoma cell line 18P7E or by a subculture thereof; may correspond to those of an antikine antibody analog of 18P7E, or correspond to those of an antikine monoclonal antibody that competitively blocks or inhibits the binding of MAb 18P7E to two, three or more of the CC chemokines to which it binds. Such antibodies may be in the form of a human antibody, a humanized antibody, a chimeric human-murine antibody, murine, avian or other vertebrate antibody; or an antigen binding fragment thereof.

The light and heavy variable domain sequences, including those of each CDR, of 3C12F, 7D1G, 7D12A, 18V4F, 18P7E and their analogs, or other antikine antibodies, may be employed as a core structure for drug design of antibody mimics, as competitive inhibitors which interfere with CC chemokine-receptor binding, as ligands to isolate or identify chemokines or anti-ithotypic antibodies to CC chemokine antibodies, or as immunogens to induce anti-idiotype antibodies against antibodies to CC chemokines. Such peptides include modified or stabilized peptides or conformationally constrained peptides, such as a circular or looped peptide comprising the CDRs of an antikine antibody. Methods of peptide design using the CDR of antibodies are known in the art and are incorporated by reference to Takahashi, et al., Chem. Eur. J. 6(17):3196-3203 or Feng, et al., Cell. Host. Microb. 98(2): 311-316. These CDRs include those of SEQ ID NOS: 3-5, 8-10, 13-15, 18-20, 23-25, 28-30, 33-35, 38-40, 43-45, 48-50, 53-55, 58-60, 63-65 and 68-70 as well as analogs of these peptide sequences produced by affinity maturation. Combinations of different CDRs either as combinations of separate peptides comprising different CDRs, or as a conjugate, hybrid, or fusion of two or more CDR peptide sequences to form a unitary peptide product may be used to modulate or inhibit CC chemokine binding or activity, inhibit chemokine dimer- or multimerization, or induce useful physiological or immunological responses.

The antikine antibodies of the invention may be formulated as a composition comprising the antikine antibody or its antigen binding fragments with a carrier, excipient or buffer as described in more detail below.

Methods for making hybridoma cell lines producing antikine antibodies include sequentially immunizing a mammal, such as a mouse, with a particular CC chemokine, followed by boosting with one or more different CC chemokines, and then producing a hybridoma cell line from said mammal, for example by fusion of its spleen cells with a myeloma or immortalized B cell line, and isolating a hybridoma cell line that produces an antikine antibody binding to two or more chemokines or CC chemokines.

Methods for treating a disease, disorder or condition mediated by one or more CC chemokines, especially those mediated by at least two or three CC chemokines recognized by an antikine antibody comprise administering to a subject in need thereof the antikine antibody or an antigen binding fragment thereof. The disease, disorder, or condition may be characterized by inflammation or by autoimmunity.

Other aspects of the invention will be apparent from the drawings and the detailed description of the embodiments which follows.

BRIEF DESCRIPTION OF THE DRAWINGS

FIGS. 11A and 11B depict the chemokine binding specificity of 18V4F using the MSD platform.

FIGS. 13A, 13B, 13C, and 13D show alignments of the chemokine sequences recognized by the five antikine antibodies.

DETAILED DESCRIPTION OF THE INVENTION

Figure 1:
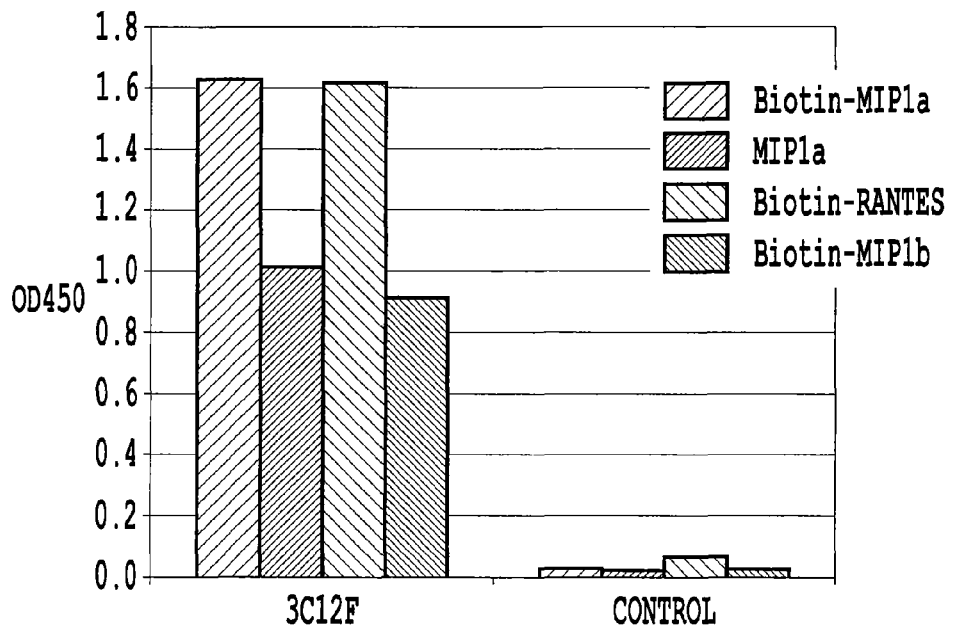
FIG. 1 depicts binding of purified 3C12F to chemokines by ELISA.

The term "antibody" is to be construed broadly as describing single monoclonal antibodies, antibody compositions with polyepitopic specificity, as well as antibody fragments (e.g., Fab, F(ab')$_2$, scFv and Fv), as long as they exhibit the desired biological activity, such as an ability to bind to a particular antigen, epitope, or antigenic determinant. This term includes intact antibodies, full-length or non-truncated antibodies, as well as antibody fragments, and antibody derivatives, variants and analogs.

Antibodies, including antikine antibodies described below, may have different isotypes—e.g., IgA, IgD, IgE, IgG, IgM, and IgY—as well as various isotype subclasses, such as human IgG subclasses 1, 2, 3 and 4 or IgA subclasses 1 and 2. Multivalent antibodies may be characterized by their avidity for a multivalent antigen. Avidity strengthens binding to antigens with repeating identical epitopes, and some chemokines have been characterized by dimeric or tetrameric structures. The more antigen-binding sites an individual antibody molecule has, the higher its avidity for antigen. Antibodies may be obtained or derived from various vertebrates, including those of mammals and birds.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Köhler & Milstein, Nature, 256:495 (1975), or may be made by recombinant DNA methods, see e.g., Cabilly, et al., U.S. Pat. No. 4,816,567.

A "chimeric antibody" refers to antibodies containing amino acid sequences from two different sources, e.g., one that contains conserved human antibody segments spliced to variable segments of a murine antibody known to bind to a particular epitope or antigen. One portion of each of the amino acid sequences of heavy and light chains is identical or homologous to sequences in antibodies derived from a particular species or belonging to a particular class, while the remaining segment of the chains is homologous or identical to sequences from another species. In one embodiment, the invention features a chimeric antibody or antigen-binding fragment, in which the variable regions of both light and heavy chains mimic the variable regions of antibodies derived from one species of mammals, while the constant portions are homologous to the sequences in antibodies derived from another species. In one embodiment of the invention, chimeric antibodies are made by grafting CDRs from a mouse antibody onto the framework regions of a human antibody. Thus, the monoclonal antibodies of the invention include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies retaining an ability to bind to a CC chemokine. The features of chimeric antibodies and methods for making them are incorporated by reference to Cabilly, et al., U.S. Pat. No. 4,816,567; and Morrison et al., Proc. Natl. Acad. Sci. USA, 81:6851-6855 (1984).

A "complementarity determining region (CDR)" forms part of a variable region of a light or heavy chain of an immunoglobulin molecule. These sections of an antibody chain form a portion of the region which determines specificity of an antibody for a particular epitope on an antigen and form portions of the antibody molecule that may directly bind to the epitope. CDR3 shows the most variability amongst the different CDRs forming an antibody. CDRs mediate contact between an antibody and the epitope it recognizes. Isolated peptides comprising or analogous to CDR sequences may exhibit additional functional activities: Polonelli, et al., PLoS One 3:e2371 (2008).

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or decrease immunogenicity. A "humanized antibody" encompasses not completely human antibodies that are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to two or more CC chemokines that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). Methods for producing humanized antibodies are incorporated by reference to European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, Molecular Immunology 28(4/5):489-498 (1991); Studnicka, et al., Protein Engineering 7(6):805-814 (1994); Roguska, et al., Proc. Natl. Acad. Sci. USA 91:969-973 (1994); Tan, et al., J. Immunol. 169:1119-25 (2002); Caldas, et al., Protein Eng. 13:353-60 (2000); Morea, et al., Methods 20:267-79 (2000); Baca, et al., J. Biol. Chem. 272:10678-84 (1997); Roguska, et al., Protein Eng. 9:895-904 (1996); Couto, et al., Cancer Res. 55 (23 Supp):5973s-5977s (1995); Couto, et al., Cancer Res. 55:1717-22 (1995); Sandhu, Gene 150:409-10 (1994); Pedersen, et al., J. Mol. Biol. 235:959-73 (1994); Jones, et al., Nature 321:522-525 (1986); Reichmann et al., Nature 332:323-329 (1988); and Presta, Curr. Op. Struct. Biol. 2:593-596 (1992).

A "variant" or "analog" antibody, refers herein to a molecule which differs in amino acid sequence from a "parent" antibody amino acid sequence by virtue of addition, deletion and/or substitution of one or more amino acid residue(s) in the parent antibody sequence. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind the receptor and preferably has properties which are superior to those of the parent antibody. For example, the variant may have a stronger binding affinity, enhanced ability to activate the receptor, etc. To analyze such properties, one should compare a Fab form of the variant to a Fab form of the parent antibody or a full length form of the variant to a full length form of the parent antibody, for example, since it has been found that the format of the antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody.

The "parent" antibody herein is one which is encoded by an amino acid sequence used for the preparation of the variant. Preferably, the parent antibody has a human framework region and has human antibody constant region(s). For example, the parent antibody may be a human antibody into which the CDRs of a donor (murine) antibody are embedded.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The phrase "substantially free of cellular material" includes preparations of an antibody or antibody fragment in which the antibody or antibody fragment is separated from cellular components of the cells from which it is isolated or recombinantly produced. Thus, an antibody or antibody fragment that is substantially free of cellular material includes preparations of antibody or antibody fragment having less than about 30%, 20%, 10%, or 5% (by dry weight) of heterologous protein (also referred to herein as a "contaminating protein"). When the antibody or antibody fragment is recombinantly produced, it is also preferably substantially free of culture medium, i.e., culture medium represents less than about 20%, 10%, or 5% of the volume of the protein preparation. When the antikine antibody or its antibody fragment is produced by chemical synthesis, preferably it is produced free of chemical precursors or other chemicals, i.e., it is separated from chemical precursors or other chemicals which are involved in the synthesis of the protein. Accordingly such preparations of the antibody or antibody fragment have less than about 30%, 20%, 10%, 5% (by dry weight) of chemical precursors or compounds other than the antibody or antibody fragment of interest. In a one embodiment, antibodies of the invention or fragments thereof are isolated or purified.

The term "antikine antibody" refers to an antibody as defined above that binds to two or more chemokines, preferably the antikine antibody will bind three or more human CC chemokines. An antikine antibody may be a monoclonal or polyclonal antibody, and preferably will be an isolated or purified monospecific or monoclonal antibody. An antikine antibody may be a mammalian antibody, such as a murine or human antibody, or a chimeric or humanized antibody. Fully human antibodies may be obtained from humans or from transgenic animals or phage display platforms, see Lonberg, Curr. Opin. Immunol. 20(4):450-9 (2008) to which procedures of obtaining human antibodies from transgenic animals is incorporated by reference. Antikine antibodies may be synthetic antibodies, single domain antibodies, such as nanobodies ($V_HH$) or camelized antibodies, single-chain Fvs (scFv), single chain antibodies, Fab fragments, F(ab') fragments, disulfide-linked Fvs, intrabodies, and anti-idiotypic (anti-Id) antibodies (including anti-idiotype and anti-anti-idiotype antibodies to the antikine antibodies of the invention, such as 3C12F, etc.), bispecific, and fragments of any of the above that bind to determinants or epitopes of a CC chemokine. Various structural forms of engineered antibodies are incorporated by reference to Antibody Engineering: A Practical Approach, edited by McCafferty, et al., Oxford University Press (1996). The term "antikine antibody" encompasses immunoglobulin molecules and immunologically active fragments of immunoglobulin molecules containing at least one antigen binding site (ABS). These may be of any isotype including IgA, IgD, IgE, IgG, IgM, and IgY and may be derived from vertebrates, such as mammals and birds, which produce antibodies. Preferably, antikine antibodies will be human or humanized, though antikine antibodies may be suitable for administration to animals, such as domestic or commercially raised animals, or wild animals or animals raised in captivity. These include companion animals, such as dogs and cats; livestock, such as bovine, equine, buffalo, water buffalo, swine, goats, sheep, camels, llamas, etc.; and fowl, such as chickens, turkeys, geese, falcons, etc. Those of skill in the art would understand how to produce and adapt antikine antibodies for non-human uses, e.g., by inducing antibodies to CC chemokines expressed by a particular type of animal and/or by an antibody-engineering process analogous to humanization.

Antikine antibodies or fragments thereof will bind to specific CC chemokines and not non-specifically bind to other chemokines or polypeptides. Antikine antibodies or their fragments that immunospecifically bind to a CC chemokine or a fragment of a CC chemokine may cross-react with other antigens. However, antikine antibodies or fragments that immunospecifically bind to a CC chemokine or fragment thereof may be selected that do not cross-react with other antigens. Antikine antibodies or their fragments that immunospecifically bind to specific CC chemokines can be identified, for example, by immunoassays or other techniques known to those of skill in the art.

A "fragment" describes a portion of an intact polypeptide molecule, such as a CC chemokine or an antikine immunoglobulin. A "fragment" may encompass a peptide or polypeptide comprising an amino acid sequence of at least 5, 10, 15, 20, 25, 30, 35, 40, 45, 50, 60, 70, 75, 80, 90, 100, 120, 130, 150, 175, 200, or 250 contiguous amino acid residues of an amino acid sequence, such as the sequence of an intact mature CC chemokine or of a light or heavy antibody polypeptide chain. For a CC chemokine, a fragment will be a portion of the molecule that is shorter than the length of the mature chemokine, such as a CC chemokine fragment comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, or any intermediate value up to but not including the full amino acid sequence of the mature CC chemokine. For an antikine antibody, a fragment includes a peptide or polypeptide comprising an amino acid of at least 5, 10, 15, 20, 25, 30, 35, 40, 45, or 50 contiguous amino acid residues, or up to but not including the full length of a $V_H$ and/or $V_L$ portion of an antibody that specifically binds to a CC chemokine, and which binds to at least two or three CC chemokines bound by the intact antikine antibody. An antikine antibody fragment may be a single chain fragment, e.g., a light or heavy chain or a portion of a light or heavy chain, but also includes fragments with multiple chains, such as a Fab or $F(ab')_2$ fragments.

"Affinity matured antibodies" are antibodies that have had their binding affinity and/or biological activity increased by altering the type or location of one or more residues in the variable region. An example of alteration is a mutation which may be in either a CDR or a framework region. An affinity matured antibody will typically have its binding affinity increased above that of the isolated or natural antibody or fragment thereof by from 2 to 500 fold. Affinity matured antibodies may have nanomolar or even picomolar affinities to the receptor antigen. Affinity matured antibodies are produced by procedures known in the art. Marks, J. D. et al., Bio/Technology 10:779-783 (1992), which is incorporated by reference, describes affinity maturation by $V_H$ and $V_L$ domain shuffling. Random mutagenesis of CDR and/or framework residues are incorporated by reference to Barbas, C. F. et al. Proc Nat. Acad. Sci, USA 91:3809-3813 (1994), Schier, R. et al. Gene 169:147-155 (1995), Yelton, D. E. et al. J. Immunol. 155; 1994-2004 (1995), Jackson, J. R. et al. J. Immunol. 154(7):3310-9 (1995), and Hawkins, R. E. et al., J. Mol. Biol. 226:889-896 (1992).

An "antikine antibody derivative" refers to a polypeptide that comprises an amino acid sequence of an antikine antibody or a CC chemokine binding antibody fragment that specifically binds to at least two, three, four or more CC chemokines, which has been altered by the introduction of amino acid residue substitutions, deletions or additions. The term "derivative" as used herein also refers to an antikine antibody or a fragment of an antikine antibody that has been covalently modified, e.g., by glycosylation, acetylation, pegylation, phosphorylation, amidation, derivatization by known protecting/blocking groups, proteolytic cleavage, linkage to a cellular ligand or other protein, etc. Such an antikine antibody derivative may be produced by chemical modifications using techniques known to those of skill in the art, including, but not limited to specific chemical cleavage, acetylation, formylation, metabolic synthesis of tunicamycin, etc. An antikine antibody derivative will retain an ability to specifically bind to two or more CC chemokines.

An "antikine antibody analog" refers to a polypeptide comprising a substantially similar amino acid sequence as a known antikine antibody and which retains the ability of the known antikine antibody to bind to two or more CC chemokines. An analog may also contain 1, 2, 3, 5 or 10 or more non-classical amino acids. A polypeptide that has a similar amino acid sequence to an antikine antibody polypeptide may be described by reference to identity to another protein or by reference to an encoding polynucleotide sequence include as:

(i) a polypeptide having an amino acid sequence that is at least 50%, at least 55%, at least 60%, at least 65%, at least 70%, at least 75%, at least 80%, at least 85%, at least 90%, at least 95% or at least 99% identical to the amino acid sequence of at least one light or heavy chain, or at least one CDR of a known antikine antibody;

(ii) a polypeptide encoded by a polynucleotide sequence that hybridizes under stringent conditions to a nucleotide sequence encoding an antikine antibody, or antikine antibody fragment described herein, which polypeptide comprises at least 5, 10, 15, 20, 25, 30, 35, 40, 50, 75, 90, 100, 125, or at least 150 amino acid residues. The conditions of temperature and ionic strength determine the "stringency" of the hybridization. Low stringency hybridization conditions, corresponding to a $T_m$ of 55° C., include e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC and high stringency hybridization conditions correspond to the highest $T_m$, e.g., 50% formamide, 0.1×SSC; and (iii) a polypeptide encoded by a nucleotide sequence that is at least 50%, 55%, 60%, 65%, 70%, 75%, 80%, 85%, 90%, 95% or at least 99% identical to the nucleotide sequence encoding a known antikine antibody, or antikine antibody fragment. A polypeptide with similar structure to an antikine antibody, or antikine antibody fragment described herein refers to a polypeptide that has a similar secondary, tertiary or quaternary structure to the known antikine antibody of its fragment. Polypeptide and protein structure may be determined by methods known to those skilled in the art, including but not limited to, X-ray crystallography, nuclear magnetic resonance, and crystallographic electron microscopy.

The term "hypervariable region" refers to the amino acid residues of an antibody which are responsible for antigen binding. The hypervariable region comprises amino acid residues from a "Complementarity Determining Region" or "CDR" in the heavy chain and light chain variable domains; Kabat, et al., Sequences of Proteins of Immunological Interest, 5th Ed. Public Health Service, National Institutes of Health, Bethesda, Md. (1991) and/or those residues from a "hypervariable loop" in the heavy chain and light chain variable domains; Chothia and Lesk, J. Mol. Biol. 196:901-917 (1987). "Framework Region" or "FR" residues are those variable domain residues other than the hypervariable region residues as herein defined. Structural features of antibodies and methods for determining or analyzing antibody structure are well-known to those in the art are incorporated by reference to Kabat, id., Chothia, et al., id.; Déret, et al., Comput. Appl. Biosci. 11(4):435-9 (1995); Martin, Protein 25(1):130-3 (1996) and Abhinandan, et al., Mol. Immunol. 45(14):3832-9 (2008); and Abhinandan, et al., J. Mol. Biol. 369(3):852-62 (2007).

A "CC-chemokine" refers to a polypeptide from the family of chemotactic cytokines containing four conserved cysteine residues, the first two of which are adjacent as described for example by Van Coillie, et al., Cytokine & Growth Factor Rev. 10:61-86 (1999). CC chemokines are also known as β-chemokines. Based on these adjacent cysteine-cysteine (cys-cys, or C—C) residues the β-chemokines are known as "CC" chemokines, where "CC" denotes the adjacent cysteine residues. Examples of CC chemokines are those binding to CCR1 and CCR5, including CCL3/MIP-1α, CCL4/MIP-1β and CCL5/RANTES. CC chemokines exist in mammals and birds. Terms used for the human or murine version of a particular chemokine, e.g., human CCL3/MIP-1α may be used to identify the corresponding molecule in another species, e.g., "murine MIP-1α" or "bovine MIP-1α" and should be understood to refer to the analogous, structurally similar molecule in the species being referred to. Analogous chemokines among mammalian and avian species may have at least 40%, 50%, 60%,70%, 80%, 90%, 95% or 99%, or any intermediate value within this range, sequence identity and will exhibit the same or similar functional immunological activities.

Sequences for vertebrate CC chemokines, including those of mammals and birds, are incorporated by reference to the NCBI database with specific reference to those sequences identified by the last updated accession numbers in that database (last accessed on Aug. 9, 2010) and to Fernandez & Lolis, Annu Rev. Pharmacol. Toxicol. 42:469 (2002) which is hereby incorporated by reference.

The specific accession numbers for the polynucleotide and polypeptide sequences of human chemokines CCL2/MCP-1, CCL3/MIP-1α, CCL4/MIP-1β, CCL5/RANTES, CCL14/HCC-1, CCL15/HCC-2, CCL18/PARC, and CCL23/MPIF-1 and others are provided in Table 4. Each is specifically incorporated by reference to the catalog, supplier, or NCBI accession numbers described in Table 4. These chemokines are commercially available from the suppliers described in Table 4.

The term "CC chemokine determinant" as used herein refers to portions of a CC chemokine which are contacted by the antigen binding residues of an antibody. This term encompasses both conventional linear epitopes recognized by an antikine antibody on a CC chemokine as well as conformational epitopes, including nonlinear epitopes. The one or more portions of a CC chemokine bound by an antikine antibody or directly in contact with its antigen binding amino acid residues are its determinants. Removal, replacement, disruption or denaturation of an antigenic determinant of a CC chemokine may reduce or eliminate the ability of an antikine antibody to bind to the CC chemokine. Methods for determining antibody binding epitopes are well-known in the art as shown by Ladner, Biotechnol. Genet. Eng. Rev. 24:1-30 (2007), which is incorporated by reference. CC chemokine determinants include segments or domains involved in binding to a chemokine receptor (e.g., CCR1 or CCR5), such as its N-loop, β-1, 2 and 3 strands, the 30's, 40's and 50's loops and its C terminal helical segment, these determinants are incorporated by reference to Fernandez & Lolis, Annu. Rev. Pharmacol. Toxicol. 42:469 (2002), Viola, et al., Annu. Rev. Pharmacol. Toxicol. 48:171, and Pakianathan, et al., Biochem. 36(32):9642 (1997).

CC chemokine determinants are also defined by binding of proteins from pathogens, such as the CC chemokine determinants bound by vCCI of vaccinia virus, these determinants are incorporated by reference to Zhang et al., Proc. Natl. Acad. Sci. 103(38):13985-13990 (2006).

The terms "bind" or "binding" refer to a chemical or physical contact or interaction between two different substances. This includes an association between an antikine antibody and a corresponding determinant, such as an epitope on a CC chemokine molecule. Such contact or interaction may be by one or more of ionic, non-ionic, hydrogen bonding, van der Waals bonding, hydrophobic bonding, or other known types of intermolecular bonding. Binding may involve direct contact between two molecules, such as between a ligand and its corresponding receptor, or indirect through an intervening moiety, such as covalent or noncovalent binding via a linker or bi- or polyvalent moiety.

"Binding affinity" is described by affinity constant $K_a$, which is the ratio between the rate constants for binding and dissociation of antibody and antigen. Typical affinities for IgG antibodies are $10^{-5}$-$10^{-9}$ mole/L. Antibody affinity is measured by many different techniques known in the art including: equilibrium dialysis, surface plasmon resonance (BIAcore®), and kinetic exclusion assay (KinExA®). The relationship between bound and free antigen and antibody affinity is expressed by the Scatchard equation, $r/c=Kn-Kr$, where r=the ratio of [bound antigen] to [total antibody], c=[free antigen], K=affinity, and n=number of binding sites per antibody molecule (valence). If all the antibodies have the same affinity for antigen (e.g., a monoclonal antibody), a plot of r/c versus r will yield a straight line with a slope of $-K$ and an r intercept approaching n. If the antibody is heterogeneous (e.g., polyclonal), the plot of r/c versus r will yield a curved line; the average affinity can be determined by the slope of the curve when half the binding sites are full ($r=1$).

The phrase "specifically binds to a CC chemokine" describes an above-background interaction of antibody or an antibody fragment with a particular CC chemokine or set of CC chemokines, but not with other chemokines. CC chemokines include, but are not limited to, CCL3/MIP-1α, CCL4/MIP-1β, and CCL5/RANTES, and examples of CC chemokine segments or domains include its chemokine receptor binding residues, its N-loop, β-1, 2 and 3 strands, the 30's, 40's and 50's loops and its C terminal helical segment. An antibody that specifically binds to a CC chemokine or one of its domains or segments may bind to other antigens with lower affinity as determined by, e.g., immunoassays, surface plasmon resonance (BIAcore®), or other assays known in the art. For example, an antikine antibody that has a four-fold or greater ability to bind to a particular CC chemokine compared to another or control antibody when compared at the same concentration and under the same conditions would be considered to specifically bind to the CC chemokine. However, other comparative binding criteria may be used which establish a significant difference in the amount or affinity of binding, these would include a 2, 3, 4, 5, 10, 20, 50, 100 or 1000-fold greater amount of binding for the antikine antibody or a 2, 5, 10, 15, 20, 100, or at least 1,000-fold greater binding affinity.

The antibodies or fragments that specifically bind to two, three, four, five, or more CC chemokines need not cross-react with other non-chemokine antigens or non-CC chemokines. Antikine antibodies or fragments that specifically bind to CC chemokines or their fragments can be identified by immunoassays, BIAcore, or other techniques known to those of skill in the art. An antibody or a fragment thereof binds specifically to a CC chemokine antigen or fragment thereof with higher affinity than to any cross-reactive antigen as determined using experimental techniques, such as Western blots, radioimmunoassays (RIA) and enzyme-linked immunosorbent assays (ELISA). See, e.g., Paul, ed., *Fundamental Immunology*, Second Edition, Raven Press, New York (1989) at pages 332-336 for a discussion regarding antibody specificity.

The term "inhibitory concentration" refers to a concentration of antibody, such as an antikine antibody or its CC chemokine-binding fragments, which in comparison to a control reduce a CC chemokine activity, for example by 5%, 10%, 20%, 30%, 50%, 80%, 90%, 95%, 99% or up to 100%. CC chemokine activity may be determined in vivo or in vitro and include assays of CC chemokine activities, such as chemotaxis. Such assays include calcium flux or integrin activation. The modulatory effects of an antikine antibody or its CC-chemokine binding fragments, as well as control antibodies, such as those which do not bind to CC chemokines or those binding to a single chemokine, may also be determined in in vivo animal models, including those measuring CC chemokine activation of immune phenomena, such as inflammation and autoimmunity. Inhibiting the activity of a chemokine refers to causing a relative decrease in at least one activity of a chemokine in the presence of an inhibitory agent as compared to the activity in the absence of the agent. Inhibition may involve antagonism or neutralization of chemokine activity, for example, by antibody binding to an active site on the chemokine, or by binding that leads to effective removal, immobilization, or inactivity of the chemokine. The term "chemotaxis inhibition" refers to a decrease in the relative amount of chemotactic activity of cells in the presence of the antibody or antigen-binding fragment thereof in comparison with chemotactic activity observed in the absence of the antibody or antigen-binding fragment thereof. Well known methods of measuring chemotactic inhibition of particular types of cells, including different leukocyte cell types, are available and are incorporated by reference to *Chemokine Protocols*, Meth. in Mol. Biol. 138 (2000), Humana Press, Eds. AEI Proudfoot, TNC Wells, and CA Power.

An "isolated" or "purified" product or component is substantially free of cellular material or other contaminating proteins from the cell or tissue source from which the product or component is derived, or substantially free of chemical precursors or other chemicals when chemically synthesized. An isolated or purified component, molecule or other substance (including a peptide, polypeptide, antibody, chemokine, polynucleic acid, or cell) is one that has been removed from, or synthesized separately from, its ordinary or natural or indigenous environment. An isolated or purified product or component may also be physically or chemically removed or separated from the admixture or ingredients with which it is associated, including undesired biological contaminants, or, if synthesized, by substrates or byproducts associated with its synthesis. Purification may extend to any degree including removal of 1, 5, 10, 50, 75, 90, 95 or 100% of the other components. In the case of an antibody, isolation may constitute removal from blood or serum, or for a monoclonal antibody, from ascites or tissue culture fluid.

The terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. The nucleic acid sequences of the invention may encode portions of an antikine antibody analog or variant. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA. An "isolated" nucleic acid molecule is one which is separated from other nucleic acid molecules which are present in the natural source of the nucleic acid molecule. An "isolated" nucleic acid molecule, such as a cDNA molecule, can be substantially free of other cellular material, or culture medium when produced by recombinant techniques, or substantially free of chemical precursors or other chemicals when chemically synthesized. In a one embodiment, nucleic acid molecules encoding antibodies of the invention or fragments thereof are isolated or purified.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome. A host cell may be used to recombinantly express an antikine antibody or one of its components, e.g., a light or heavy chain or fragment thereof.

To determine the "percent identity" of two nucleic acid or amino acid sequences, the sequences are first aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions multiplied by 100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, Proc. Natl. Acad. Sci. U.S.A. 87:2264-2268 (1990), modified as in Karlin and Altschul, Proc. Natl. Acad. Sci. U.S.A. 90:5873-5877 (1993). Such an algorithm is incorporated into the NBLAST and XBLAST programs of Altschul et al., J. Mol. Biol. 215:403 (1990). BLAST nucleotide searches can be performed with the NBLAST nucleotide program parameters set, e.g., for score=100, wordlength=12 to obtain nucleotide sequences homologous to a nucleic acid molecule of the present invention. BLAST protein searches can be performed with the XBLAST program parameters set, e.g., to score=50, wordlength=3 to obtain amino acid sequences homologous to a protein molecule of the present invention. To obtain gapped alignments for comparison purposes, Gapped BLAST can be utilized as described in Altschul et al., Nucleic Acids Res. 25:3389-3402 (1997). Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used. Another preferred, non-limiting example of a mathematical algorithm utilized for the comparison of sequences is the algorithm of Myers and Miller, CABIOS 4:11-17 (1988). Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

A "conservative change" refers to alterations that are substantially conformationally or antigenically neutral; producing minimal changes in the tertiary structure of a peptide or polypeptide variant, or producing minimal changes in the antigenic determinants of the variant or analogous peptides or polypeptides, as compared to the parental or native peptide or polypeptide. In the context of chemokines, conservative changes include amino acid substitutions that do not substantially affect the specificity and/or affinity of the resulting chemokine variant or analog, for example, as determined by its ability to exhibit at least one function of the parental chemokine including such functions as induction of chemotaxis, participation in cytokine networks or otherwise inducing enzyme or cytokine production, or binding to the receptor for the parental or native chemokine. As applied to variants or analogs of the antibodies, antibody fragments, including CDR segments, a conservative change refers to an amino acid substitution that produces an antibody product that is able to bind to the same epitope or antigen as the corresponding unmodified antibody product. Prediction of which amino acid substitutions maintain the conformational and antigenic neutrality of a molecule are within the skill of the art as described by Berzofsky, Science 229:932-940 (1985) and Bowie, et al., Science 247:1306-1310 (1990). Guidance as to which substitutions will most likely maintain conformational and antigenic neutrality include (a) substitution of hydrophobic amino acids is less likely to affect antigenicity because hydrophobic residues are more likely to be located in a protein's interior, (b) substitution of physiochemically similar amino acids is less likely to affect conformation because the substituted amino acid structurally mimics the native amino acid; and (c) alteration of evolutionarily conserved sequences is likely adversely to affect conformation as such conservation suggests that the amino acid sequences may have functional importance. A "composition" or "pharmaceutical or therapeutic composition" refers to a combination of carrier, excipient, or solution containing an antikine antibody or its CC-chemokine binding fragments, or its other fragments, that directly or indirectly reduce the severity of or treat a condition, disorder or disease mediated by a CC chemokine, or at least one symptom thereof. The term "pharmaceutically acceptable carrier" includes any and all carriers and excipients such as diluents, solvents, dispersing agents, emulsions, lipid bilayers, liposomes, coatings, preservatives including antibacterial or antifungal agents, isotonic agents, pH buffers, and absorption modulating agents, and the like, compatible with the molecules of the present invention and suitable for pharmaceutical administration. The use of such carriers, disintegrants, excipients and agents for administration of pharmaceutically active substances is well known in the art, see the *Handbook of Pharmaceutical Excipients*, 3$^{rd}$ edition, Am. Pharm. Assoc. (2000) which is incorporated by reference. The pharmaceutical compositions of the invention are generally formulated for compatibility with an intended route of administration, such as for parenteral, oral, or topical administration.

The therapeutic compositions of the invention include at least one antibody or antibody fragment of the invention in a pharmaceutically acceptable carrier. A "pharmaceutically acceptable carrier" will be at least one component conventionally admixed with, and used for, the administration of an active ingredient, biological product, or drug. A carrier may contain any pharmaceutical excipient used in the art and any form of vehicle for administration. The compositions may be, for example, injectable solutions, aqueous suspensions or solutions, non-aqueous suspensions or solutions, sprays, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like. A suitable dosage form may be selected by one of skill in the art from forms such as those described by the U.S. FDA CDER Data Standards Manual C-DRG-00201, Version 08; or those listed at the FDA website http://www.fda.gov/ForIndustry/DataStandards/StructuredProductLabeling/ucm162038.htm (last accessed Aug. 9, 2010); both of which are hereby incorporated by reference.

Orally administered compositions can include a solid carrier or excipient or may be formulated as liquid or gel preparations and may include an edible or inert carrier and may be enclosed in capsules, compressed into tablets, or formulated as a troche. Orally administered compositions may be prepared in a time-release or encapsulated form to prevent degradation in the stomach and optimize uptake of a molecule.

Injectable compositions may be formulated by methods well known in the art and may encompass sterile solutions or dispersions of therapeutic molecules. Such will usually include a sterile diluent, such as water, normal saline, or other buffer compatible with the molecules of the invention. Injectable compositions may be prepared in unit dosages or in unit dose containers, such as vials, ampules, or syringes.

Conventional buffers and isotonic agents may be used and pH may be adjusted using well known agents, such as HCl or NaOH or buffers. Antimicrobial or bacteriostatic agents, chelating agents, such as EDTA or EGTA, and antioxidants and preservatives may be present.

The therapeutic compositions of the invention may be administered by any acceptable route of administration including topically, on to a mucous membrane, orally or enterically or parenterally. These routes include, but not limited to topical, transmucosal, orally (including buccal, sublingual), mucosally (conjunctiva, nasal, sinal, urethral, vaginal, intestinal, rectal), enteric, transdermal, intradermal, subcutaneous (s.c.), intramuscular, intraperitoneal, intravenous (i.v.) intracardiac, into a joint or bone, into an organ (brain, spinal chord, eye, ear, liver, spleen, kidney, gall bladder, bladder), into bone, cartilage, or joint tissue, by inhalation (e.g., intranasal, intratracheal, intrapulmonary, or intrabroncial), oral, subuccal. Routes may be selected by those of skill in the art from those listed in the U.S. FDA, CDER, Data Standards Manual "Routes of Administration", CDRG-00301, Version 004; Data Element Name. Route of Administration.
Data Element OID: 2.16.840.1.113883.3.26.1.1.1
Data Element NCI Concept ID: C38114
  Version Number. 004
  available at http://www.fda.gov/Drugs/GuidanceComplianceRegulatoryInformation/DrugRegistrationandListing/ucm084039.htm (last accessed Aug. 9, 2010); which are hereby incorporated by reference.

A "therapeutically effective amount" refers to that amount of the therapeutic agent sufficient to reduce the severity of or treat a condition, disorder or disease mediated by CC chemokines, to enhance the therapeutic efficacy of another therapy of the condition, disorder or disease, or to prevent the recurrence or an increase in severity of the condition, disorder or disease or at least one of its symptoms. A therapeutically effective amount may refer to the amount of therapeutic agent sufficient to delay or minimize the onset of disease. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease. Used in connection with an amount of an antibody of the invention, the term can encompass an amount that improves overall therapy, reduces or avoids unwanted effects, or additively enhances the therapeutic efficacy of, or synergizes with, another therapeutic agent.

The term "subject" or "patient" as used herein refers to a vertebrate that expresses CC chemokines, including avian and mammals (e.g., bovines, equines, swine, goats, sheep, canines, or felines) and preferably a human. A subject or patient may be one in need of treatment with an effective amount of an antikine antibody that modulates CC chemokine activity of the CC chemokines it recognizes.

An "inflammatory condition, disorder, or disease" refers to an evident or quantifiable physiological phenomenon, including, but not limited to edema, fever, chemotaxis or migration of leukocytes, proliferation of blood vessels, proliferation of connective tissue, redness, localized heat, exudation, and other signs as described in Robbins, *The Pathological Basis of Disease*, 6$^{th}$ edition, Cotran, et al. (eds.), W.B. Saunders, Co. (1999), especially Chapters 3, 7 and 15. In the context of antikine antibodies to CC-chemokines, this term would refer to phenomena associated with, or directly or indirectly mediated by, a CC-chemokine, such as MIP-1α,MIP-1βRANTES, MCP-1, or other chemokines.

An "immunoaffinity resin" refers to a solid substrate to which at least one immunological ligand or receptor is bound. For example, an antikine antibody may be bound to a resin via a region other than its antigen combining site, thereby allowing the antibody to bind antigenic determinants on CC chemokines. Similarly, a CC chemokine may be operatively bound to a resin permitting it to bind to an antikine antibody. Many resins useful for immobilizing immunological ligands or receptors are known in the art and are routinely used to form immunoaffinity resins. Such resins are useful in analysis of components bound by a particular ligand or receptor, in immunological assays or in purification procedures. Any such resin may be used to form the immunoaffinity resins of the invention.

The inventors pursued means for solving the prior art problems associated with administering multiple antibodies to CC chemokines. Surprisingly, they discovered antibodies which can bind to more than one type of CC chemokine: antikine antibodies. These antikine antibodies provide improvements over inhibiting a single chemokine or a single chemokine receptor in an inflammatory disease setting since only a single antibody is needed to block the functions of multiple chemokines. The antikine antibodies of the invention also avoid the drawbacks of administering two or more antibodies having different pharmacokinetic properties, such as use of inconvenient separate dosing regimens for each antibody. Antikines avoid the disadvantages of bispecific antibodies which are less effective at binding to a specific chemokine antigen and form complexes which bind more readily to Fc receptors and thus taken up by cells and degraded in lysosomes.

As demonstrated herein, the inventors provide several antikine antibodies that can simplify treatment of human inflammatory and immunological conditions, disorders and diseases mediated by multiple chemokines. These antikine antibodies will serve as structural and functional prototypes for producing even more effective and safe antikine antibodies by processes such as affinity maturation and antibody humanization.

Antikine antibodies bind to and inhibit the activities of two or more CC chemokines. By targeting CC chemokines, including MIP-1α, MIP-1β, RANTES and MCP-1, the inventors identified antibodies useful for modulating chemokines activating the same or different chemokine receptors (including CCR1, CCR2, CCR3, and CCR5). For example, since MIP-1α, MIP-1β, and RANTES each bind to chemokine receptor CCR5, an antikine antibody which recognizes these three CC chemokines can more comprehensively modulate CCR5 activity than one to a single CC chemokine. CCR5 activation targets immature myeloid dendritic cells, monocytes, Th 1, $L_{reg}$, NK and plasmacytoid dendritic cells. Similarly, MIP-1α, RANTES, MPIF-1 and HCC-1 each bind to CCR1, which activation targets monocytes, memory T cells and NK cells. An antikine antibody binding to two or more of these CCR1-binding chemokines more comprehensively modulates receptor activation. An antibody that can bind and inhibit both MIP-1α and RANTES would then effectively block two of the primary ligands of both CCR1 and CCR5. Thus, the inventors have identified antikine antibodies that inhibit the primary ligands for different chemokine receptors expressed on leukocytes including monocytes and T cells implicated in inflammatory diseases. Inhibitors of either of these combinations of chemokines provide improvements over inhibiting a single chemokine (or antibodies that block binding to a single chemokine receptor) in an inflammatory disease setting since only a single antibody is needed to block the functions of multiple chemokines on a single receptor or chemokine activity on multiple receptors.

Antikine antibodies have different specificities and functional activities depending on the chemokines to which they bind. The invention provides antikine antibodies that specifically bind to a variety of CC-chemokines, and advantageously to at least two of RANTES, MIP-1α, MIP-1β and/or MCP-1. The invention further provides antibodies that specifically bind to both RANTES and MIP-1α; RANTES and MIP-1β; RANTES and MCP-1; MIP-1α and MIP-1β; MIP-1α and MCP-1; or MIP-1β and MCP-1. Similarly, the invention provides antikine antibodies that bind to three or four of RANTES, MIP-1α, MIP-1β and/or MCP-1 as well as to other closely related CC-chemokines.

The binding of an antibody or antigen-binding antibody fragment to a chemokine occurs by contact between the amino acid residues in the antigen binding sites (ABS) of the antibody and the antigenic determinants or epitopes of the chemokine. It is well-known that epitopes may be linear peptide sequences or conformation epitopes comprising multiple antigenic determinants, even single amino acids or amino acid side groups which do not form part of a linearly contiguous amino acid sequence. For example, the residues lying on one face of an α-helix may be contacted by the ABS of an antibody, while those on the opposite face are not.

The antibodies and antigen-binding antibody fragments of the invention may bind to the N-terminal or C-terminal half of a mature CC chemokine which does not contain a signal peptide. For example, the mature form of human RANTES lacks signal peptide residues 1-23. Thus, its N-terminal portion would range from residue 1-35 and its C-terminal would range from 36-68 (SEQ ID NO: 73).

The antibodies and antigen-binding antibody fragments of the invention may block CC chemokine binding by binding to CC chemokine residues associated with binding of the chemokine to its receptor. See NCBI Conserved Domain Database CDD 29111 [uid] for proposed functional domains of CC chemokines; http://www.ncbi.nlm.nih.gov/sites/entrez (last accessed Aug. 9, 2010). Prospective binding site residues are indicated for each of the CC chemokines below:

CCL3/MIP-1α residues 11-15 (CCFSY), residues 17-24 (SRQIPQNF), residues 34-35 (QC), or residues 57-67 (EWVQKYVSDLE) of SEQ ID NO: 71;

CCL4/MIP-1β residues 11-15 (CCFSY), residues 17-24 (ARKLPHNF), residues 34-35 (LC), or residues 57-67 (SWVQEYVYDLE) of SEQ ID NO: 72;

CCL5/RANTES residues 10-14 (CCFAY), residues 16-23 (ARPLPRAH), residues 33-34 (KC), or residues 56-66 (KWVREYINSLE) of SEQ ID NO: 73.

CCL14/HCC-1 residues 8-12 (CCFTY), residues 14-21 (TYKIPRQR), residues 31-32 (QC), or residues 54-64 (KWVQDYIKDMK) of SEQ ID NO: 78.

CCL15/HCC-2 residues 8-12 (CCTSY), residues 14-21 (SQSIPCSL), residues 31-32

(EC), or residues 54-64 (PGVQDCMKKLK) of SEQ ID NO: 79.

CCL23/MPIF-1 residues 9-13 (CCISY), residues 15-22 (PRSIPCSL), residues 32-33 (EC), or residues 55-65 (KQVQVCMRMLK) of SEQ ID NO: 81.

CCL18/PARC residues 10-14 (CCLVY), residues 16-23 (SWQIPQKF), residues 33-34 (QC), or residues 56-66 (KWVQKYISDLK) of SEQ ID NO: 82.

Such an antibody or antigen binding fragment may bind to segments of at least two of MCP-1, MIP-1α, MIP-1β and RANTES, as well as other related CC-chemokines, involved in binding of said chemokine to its receptor. Antikines, such as 3C12F, may bind to the same determinants as chemokine-binding viral proteins such as vCCI, or may inhibit the binding of such viral proteins to chemokines.

Monoclonal antibodies 3C12F, 7D1G, 7D12A, 18V4F and 18P7E which bind the CC-chemokines RANTES, MIP-1α and/or MIP-1β have been produced and characterized by the inventors. These antibodies provide necessary information, including structural information from hypervariable regions and light and heavy chain CDRs, for developing humanized antibodies that can simultaneously modulate the activity of multiple CC chemokines and for the treatment of inflammatory diseases mediated by CC chemokines. The hypervariable and CDR sequences of the three MAbs above are depicted by SEQ ID NOS: 2-5 and 7-10 for 3C12F; SEQ ID NOS: 52-55 and 57-60 for humanized 3C12F; SEQ ID NOS: 12-15 and 17-20 for 7D12A; SEQ ID NOS: 22-25 and 27-30 for 7D1G SEQ ID NOS: 32-35 and 37-40 for 18V4F, SEQ ID NOS: 62-65 and 67-70 for humanized 18V4F; and SEQ ID NOS: 42-45 and 47-50 for 18P7E.

Five specific types of antikine antibodies characterized by the specific antikine antibodies 3C12F, 7D1G, 7D12A, 18V4F and 18P7E are disclosed. In addition, humanized versions of 3C12F and 18V4F are disclosed.

The first type of antibody is characterized by the binding specificity of monoclonal antibodies made by hybridoma cell line 3C12F or a subculture thereof. A typical antibody of this type of monoclonal antibody (MAb) is 3C12F. Thus this type includes MAb 3C12F, as well as its analogs and derivatives, including those antibodies produced by the process of affinity maturation or by humanization. Antibodies of the 3C12F type may contain a heavy chain variable region depicted by SEQ ID NO: 2 or 52 or a heavy chain containing at least one of CDR1 (SEQ ID NO: 3 or 53), CDR2 (SEQ ID NO: 4 or 54) and CDR3 (SEQ ID NO: 5 or 55) of the 3C12F heavy chain. Such antibodies can contain a light chain variable region comprising SEQ ID NO: 7 or 57 or containing at least one of CDR1 of SEQ ID NO: 8 or 58, CDR2 as of SEQ ID NO: 9 or 59, and CDR3 as set forth by SEQ ID NO: 10 or 60. SEQ ID NOS: 2-5 and 7-10 describe non-humanized 3C12F, while SEQ ID NOS: 52-55 and 57-60 describe humanized 3C12F. Humanized 3C12F contains a heavy chain variable region depicted by SEQ ID NO: 52 or a heavy chain containing at least one of CDR1 (SEQ ID NO: 53), CDR2 (SEQ ID NO: 54) and CDR3 (SEQ ID NO: 55) of the 3C12F heavy chain. Such antibodies can contain a light chain variable region comprising SEQ ID NO: 57 or containing at least one of CDR1 of SEQ ID NO: 58, CDR2 as of SEQ ID NO: 59, and CDR3 as set forth by SEQ ID NO: 60.

A second type of antibody is characterized by the binding specificity of monoclonal antibodies made by hybridoma cell line 7D12A or a subculture thereof. A typical antibody of this type of monoclonal antibody (MAb) is 7D12A. Thus, this type includes MAb 7D12A, as well as its analogs and derivatives, including those antibodies produced by the process of affinity maturation or by humanization. Antibodies of the 7D12A antibody type may contain a heavy chain variable region depicted by SEQ ID NO: 12 or a heavy chain containing at least one of CDR1 (SEQ ID NO: 13), CDR2 (SEQ ID NO: 14) and CDR3 (SEQ ID NO: 15) of the 7D12A heavy chain. They may also contain a light chain variable region comprising SEQ ID NO: 17 or containing at least one of CDR1 of SEQ ID NO: 18, CDR2 as of SEQ ID NO: 19, and CDR3 as set forth by SEQ ID NO: 20.

A third type of antibody is characterized by the binding specificity of monoclonal antibodies made by hybridoma cell line 7D1G or a subculture thereof. A typical antibody of this type of monoclonal antibody (MAb) is 7D1G. This type includes MAb 7D1G and its analogs and derivatives, including those antibodies produced by the process of affinity maturation or by humanization. The 7D1G type of antibody may contain heavy chain variable region depicted by SEQ ID NO: 22 or a heavy chain containing at least one of CDR1 (SEQ ID NO: 23), CDR2 (SEQ ID NO: 24) and CDR3 (SEQ ID NO: 25) of the 7D1G heavy chain. They may also contain a light chain variable region comprising SEQ ID NO: 27 or containing at least one of CDR1 of SEQ ID NO: 28, CDR2 as of SEQ ID NO: 29, and CDR3 as set forth by SEQ ID NO: 30.

A fourth type of antibody is characterized by the binding specificity of monoclonal antibodies made by hybridoma cell line 18V4F or a subculture thereof. A typical antibody of this type of monoclonal antibody (MAb) is 18V4F. This type includes MAb 18V4F and its analogs and derivatives, including those antibodies produced by the process of affinity maturation or by humanization. The 18V4F type of antibody may contain heavy chain variable region depicted by SEQ ID NO: 32 or 62 or a heavy chain containing at least one of CDR1 (SEQ ID NO: 33 or 63), CDR2 (SEQ ID NO: 34 or 64) and CDR3 (SEQ ID NO: 35 or 65) of the 18V4F heavy chain. They may also contain a light chain variable region comprising SEQ ID NO: 37 or 67 or containing at least one of CDR1 of SEQ ID NO: 38 or 68, CDR2 as of SEQ ID NO: 39 or 69, and CDR3 as set forth by SEQ ID NO: 40 or 70. SEQ ID NOS: 32-35 and 37-40 describe non-humanized 18V4F, while SEQ ID NOS: 62-65 and 67-70 describe humanized 18V4F. Humanized 18V4F contains a heavy chain variable region depicted by SEQ ID NO: 62 or a heavy chain containing at least one of CDR1 (SEQ ID NO: 63), CDR2 (SEQ ID NO: 64) and CDR3 (SEQ ID NO: 65) of the 18V4F heavy chain. Such antibodies can contain a light chain variable region comprising SEQ ID NO: 67 or containing at least one of CDR1 of SEQ ID NO: 68, CDR2 as of SEQ ID NO: 69, and CDR3 as set forth by SEQ ID NO: 70.

A fifth type of antibody is characterized by the binding specificity of monoclonal antibodies made by hybridoma cell line 18P7E or a subculture thereof. A typical antibody of this type of monoclonal antibody (MAb) is 18P7E. This type includes MAb 18P7E and its analogs and derivatives, including those antibodies produced by the process of affinity maturation or by humanization. The 18P7E type of antibody may contain heavy chain variable region depicted by SEQ ID NO: 42 or a heavy chain containing at least one of CDR1 (SEQ ID NO: 43), CDR2 (SEQ ID NO: 44) and CDR3 (SEQ ID NO:45) of the 18P7E heavy chain. They may also contain a light chain variable region comprising SEQ ID NO: 47 or containing at least one of CDR1 of SEQ ID NO: 48, CDR2 as of SEQ ID NO: 49, and CDR3 as set forth by SEQ ID NO: 50.

In addition to the specific types of antikine antibodies described above, the invention encompasses antikine antibodies that bind to three, four, five or more CC-chemokines, for example, antikine antibodies, such as MAb 3C12F and the others described above, that bind to MIP-1α, MIP-1β, RANTES and/or other related CC-chemokines. Advantageously, antikine antibodies may be produced to all the CC chemokines that bind to a particular CCR, or may be targeted to those CC chemokines involved in a particular condition, disorder or disease.

An antikine antibody will have a binding affinity sufficient to permit it to bind to a CC chemokine. Exemplary binding affinities include 1,000, 900, 800, 400, 200, 150, 100, 75, 50, 40, 30, 20, 10, 5, 1, 0.1 nM or less for the CC chemokines it binds. However, it may have different binding affinity for different CC chemokines as shown in the Figures.

Selection of an antibody having an appropriate binding affinity is within the skill of those in the art. For many therapeutic purposes an antibody with a high affinity is more desirable than one with a low affinity, for example, passively administered high affinity antibodies have been demonstrated to more efficiently remove antigen in vivo than low affinity antibodies; higher affinity antibodies produced lower levels of circulating immune complexes and resulted in less impairment of glomerular function; Steward, *Antibodies: Their Structure and Function*, Taylor and Francis (1984), see Table 4.5, to which methods for antibody affinity determination as well as the characteristics and functions of low and high affinity antibodies is incorporated by reference. On the other hand, keeping in mind that the neutralizing power of an antibody depends not only on its affinity, but also its concentration, valence and molecular configuration, as well as on the site to which it is administered, for some applications a higher concentration of a lower affinity antibody may be desirable.

Immunogens used to produce antikine antibodies may include a preparation of isolated, native CC-chemokines, recombinantly expressed CC-chemokines or chemically synthesized CC-chemokines, and optionally, an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents.

The sequences of MIP-1α, RANTES, and MCP-1 proteins and polynucleotides encoding such proteins are known and may be found, for example, in publicly available sequence databases such as GenBank or by reference to the accession numbers in Table 4. Unless otherwise specified, the pertinent versions of these sequences will be those entered into these databases immediately before the filing date of this application. In addition, the sequences of various CC-chemokines, including MIP-1α, MIP-1β, RANTES, and MCP-1, have been published, and may be found, for example, in Furutani, et al., Biochem. Biophys. Res. Commun. 159:249-255 (1989) (MCP-1), Obaru, et al., J. Biochem. 99:885-894 (1986) (MIP-1α), Lipes, et al., Proc. Natl. Acad. Sci. USA 85:9704-9708 (1988) (MIP-1β), Schall, et al., J. Immunol. 141:1018-1025 (R1988)(RANTES), the disclosure of each of which is incorporated by reference herein in its entirety. It is well known that allelic variants exist for some or all of these chemokines. SEQ ID NOS: 71-74 depict the human sequences used for immunizations and screening of antikine antibodies for MIP-1α, MIP-1β, RANTES, and MCP-1.

For the production of polyclonal antibodies, various suitable host animals (e.g., rabbit, goat, mouse or other mammal) may be immunized by injection with the native protein, or a synthetic variant thereof, or a derivative of a CC chemokine or combination of more than one CC chemokine. For example, a cocktail of MIP-1α, MIP-1β, RANTES, and MCP-1 may be used as an immunogen to induce an immune response against these CC chemokines.

If desired, the polyclonal antibody molecules directed against the CC chemokines can be isolated from the mammal (e.g., from the blood) and further purified by well-known techniques, such as protein A chromatography, to obtain the immunoglobulin fraction and immunoaffinity purification to select antikine antibodies binding to two or more CC chemokines.

For many applications it will be preferable to produce an antikine antibody as a monoclonal antibody. Any technique that provides for the production of antibody molecules by continuous cell line culture may be utilized. Such techniques include, but are not limited to, the hybridoma technique—see Köhler & Milstein, Nature 256:495-497 (1975); the trioma technique; the human B-cell hybridoma technique, see Kozbor, et al., Immunol. Today 4:72 (1983) and the EBV hybridoma technique to produce human monoclonal antibodies, see Cole et al., In: *Monoclonal Antibodies and Cancer Therapy*, Alan R. Liss, Inc., pp. 77-96 (1985). Human monoclonal antibodies may be utilized in the practice of the present invention and may be produced by using human hybridomas as described by Cote, et al., Proc. Natl. Acad. Sci. USA 80: 2026-2030 (1983) or by transforming human B-cells with Epstein Barr Virus in vitro, see Cole, et al. In: *Monoclonal Antibodies and Cancer Therapy*, Alan R. Liss, Inc., pp. 77-96 (1985). All of the documents cited in this paragraph are incorporated by reference.

Beyond these conventional ways to produce monoclonal antibodies, the inventors have discovered that sequential immunization methods surprisingly, in view of the problem of original antigenic sin (the Hoskins Effect), produce antikine antibodies recognizing more than one CC chemokine. The sequence of immunization was found to influence the specificity of the resulting antibodies. These methods were found to generate antibodies that bind to particular CC chemokines and some which block binding of vaccinia virus vCCI protein to CC chemokines (RANTES/CCL5).

Sequential immunization or a vertebrate, preferably a mouse, with different chemokines proceeds by, for example, immunizing the animal with a first chemokine in an appropriate adjuvant, boosting several weeks later with a second chemokine, and finally boosting a second time with a third chemokine. However, antikine antibodies may be produced by methods involving multiple immunizations and boosts, for example, using 2, 3, 4 or more different chemokines in different combinations. Both protein and DNA-based chemokine immunizations may be performed. DNA immunization is well-known in the art and incorporated by reference to *Antibodies: A Laboratory Manual* (Eds. E. Harlow & D. Lane, 1988). The polynucleotide sequences of chemokines are well-known in the art and also incorporated by reference to Yoshie, et al., Adv. Immunol. 78: 57-110 (2001). Immunizations may be performed using adjuvants or conjugates of chemokines and carrier proteins such as those described by *Antibodies: A Laboratory Manual*, Eds. E. Harlow & D. Lane (1988), which is incorporated by reference. Preferably, about 500 µg/kg body weight or about 10 µg of a chemokine per mouse is administered and preferred adjuvants are Complete Freund's adjuvant for initial immunizations and Incomplete Freund's adjuvant for subsequent boosts. Exemplary CC chemokines for use as immunogens include at least two of CCL2/MCP-1, CCL3/MIP-1α, CCL4/MIP-1β and CCL5/RANTES.

In one embodiment of sequential immunization, a mouse is first immunized with MIP-1α and subsequently boosted with RANTES and/or MCP-1, or any other sequence of the CC chemokines RANTES, MIP-1α, MIP-1β and/or MCP-1. Mouse serum is tested for reactivity with RANTES, MIP-1α, MIP-1β and MCP-1 by ELISA. A spleen from a mouse with appropriate serum responses is then used to proceed with hybridoma production.

The antibodies produced by the hybridoma cell lines can be tested for their ability to recognize CC chemokines by ELISA and for blocking activity in either in vitro chemotaxis assays or in vCCI/chemokine binding assays. Using this strategy several unique monoclonal antibodies which bind and inhibit multiple CC chemokines were identified. These antibodies were designated "antikines". The hybridoma-produced antibodies may also be tested in other functional assays. Hybridoma cell lines producing the antibodies with multiple CC chemokine reactivities are then cloned and expanded for antibody production and purification. Screening assays to determine antibody binding specificity are well known and routinely practiced in the art. For a comprehensive discussion of such assays, see Harlow, et al. (Eds.), *Antibodies: A Laboratory Manual*; Cold Spring Harbor Laboratory; Cold Spring Harbor, N.Y., Chapter 6 (1988). After its initial identification, an antikine antibody may undergo affinity enhancement, for example, by a process of affinity maturation or by engineering of its CDR or framework sequences; or it may be humanized. For use in human therapy, preferably, an antikine antibody will be fully human or humanized and recognize two, three, four or more CC chemokines.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of CC-chemokines is facilitated by generation of hybridomas that bind to the fragment of CC-chemokines possessing such a domain. Antibodies that are specific for one or more domains within CC-chemokines, e.g., conserved domains of CC-chemokine family proteins, or derivatives, fragments, analogs or homologs thereof, are also provided herein.

The antikine antibodies and fragments thereof of the invention may be assayed for specific binding to the CC-chemokines, particularly MIP-1α, MIP-1β, RANTES, MCP-1 and/or other chemokines, in competitive and non-competitive binding immunoassays. Well-known procedures for immunoassays are hereby incorporated by reference to Stites and Terr (Eds.) *Basic and Clinical Immunology,* 7th ed., (1991); Maggio (Ed.) *Enzyme Immunoassay*, CRC Press, Boca Raton, Fla. (1980); Tijan, *Practice and Theory of Enzyme Immunoassays, Laboratory Techniques in Biochemistry and Molecular Biology*, Elsevier Science Publishers B.V., Amsterdam (1985); Harlow and Lane (Eds.) *Antibodies, a Laboratory Manual*, Cold Spring Harbor, N.Y. (1988); Chan (Ed.), *Immunoassay: A Practice Guide*, Academic Press, Orlando, Fla. (1987); Price and Newman (Eds.) *Principles and Practice of Immunoassays*, Stockton Press, N.Y. (1991); and Ngo (Ed.) (1988) *Non-isotopic Immunoassays*, Plenum Press, N.Y. (1988).

Immunoassays to measure antibody binding can be either competitive or noncompetitive. In general in the antibody context, a competitive assay involves competition for binding of a ligand between two antibodies. For example, a labeled MCP-1 may be used to assess whether one antibody can compete with another antibody for binding the labeled MCP-1. The assay may be based on such standard assays as the enzyme linked immunosorbent assay (ELISA) or radioimmunoassay (RIA) for example.

Alternatively, the antibodies and antibody fragments of the invention may be tested in noncompetitive assays for binding to substrates. For instance, a standard ELISA may be used in which the ligand (e.g., MCP-1) is immobilized on an ELISA plate. A test antibody is incubated with the ligand and allowed to bind. The plate is washed and thereafter, an enzyme-conjugated, secondary antibody (e.g., a mouse anti-human Fc antibody) binds to the test antibody if the test antibody is bound to the ligand. After washing, a substrate for the enzyme is added and allowed to react with the enzyme. Generally a color change indicates the presence of an antibody that reacts with the ligand. The ELISA may be repeated for different CC-chemokines to determine which chemokines are recognized by the test antibody.

Immunoassays often use labeled assay components. The label can be in a variety of forms and may be coupled directly or indirectly to the desired component of the assay according to methods well known in the art. Common labels for assay components include radioactive isotopes, including $^3H$, $^{125}I$, $^{35}S$, $^{14}C$, and $^{32}P$, fluorophores, chemiluminescent agents, and enzymes. The choice of a particular label will depend on the sensitivity required, the ease of conjugation with the compound, the stability requirements, and the available instrumentation, and will be easily determined by one of ordinary skill in the art.

Assays to assess whether the antibodies of the invention inhibit CC-chemokine activity, particularly MIP-1α, MIP-1β, RANTES, MCP-1 and/or other chemokines, may be easily performed using known assays for chemotaxis, intracellular calcium increase, and the like. For example, but not by way of limitation, chemokine chemotaxis assays may be performed in 96 well plastic chambers. The wells are separated by a filter into two compartments. The filter allows the passage of cells from one compartment to the next in response to chemical gradients. Test cells are placed in one compartment of the chamber in a culture medium and a CC-chemokine, for example, is placed in culture medium in the other compartment. Cells traversing the filter are counted. In other wells, the CC-chemokine is mixed with the test antibody to determine if the antibody is able to block cell migration.

For further antibody engineering of the antikine monoclonals identified by the screening procedures above, the DNA sequences of the antibodies were determined as reported in Example 7.

The affinity of the antikine antibodies of the invention may be further improved using methods known in the art, such as those described by Raipal, et al., Proc. Natl. Acad. Sci. USA. 102:8466-8471 (2005); Lippow, et al. Nat. Biotechnol. 25:1171-1176 (2007); Wu, et al., J. Mol. Biol. 368: 652-665 (2007); Yang, et al., J. Mol. Biol. 254: 392-403 (1995); and Huse, et al., J. Immunol. 149:3903-3913 (1992) which are each incorporated by reference as teaching methods for affinity maturation or enhancement of antibodies. The antikine antibodies of the invention can have affinities of less than 200, 100 nM (e.g., the originally isolated murine antibody 3C12F has an affinity of 49 nM for MIP-1α) and can be enhanced to be less than 40, 30, 20, 10, 5, 1, 0.5 or 0.1 nM during affinity maturation procedures. Procedures useful for the affinity maturation of monoclonal antibodies are well known in the art and are incorporated by reference to *Antibody Engineer-* ing (Humana Press, 2004) and *Phage Display*, T. Clackson and H. B. Lowman, editors (Oxford University Press, 2004). Such procedures can start with the chimeric form of such an antikine antibody, which can be humanized either separately or concurrently with the affinity maturation. The variable regions of the antibody may be expressed as a Fab fragment on the surface of filamentous phage. A mutagenesis strategy may be employed to change each residue within the six CDRs to make a combinatorial library of Fab fragments expressed on phage. These can be screened for binding to chemokine antigens and analyzed for improvements in affinity. Subsequently preferred amino acid substitutions can be combined for even greater improvements in affinity. At the same time mutations within the framework regions of the variable domains can be analyzed to find sequences with improved properties.

A "variant" or "analog" antibody, as described above differs in amino acid sequence from a parent antibody amino acid sequence by virtue of addition, deletion and/or substitution of one or more amino acid residue(s) in the parent antibody sequence. In one embodiment, the variant comprises one or more amino acid substitution(s) in one or more hypervariable region(s) of the parent antibody.

An antibody analog may be engineered by replacing 1, 2, 3, 4, 5, 6, 7, 8 or more amino acid residues in a CDR, hypervariable or framework region of a heavy or light chain sequence of 3C12F, 7D1G, 7D12A, 18V4F, or 18P7E. Similarly, the isotypes of such an antibody may be changed by isotype switching techniques known in the art or by genetic engineering procedures, such as CDR grafting, chimeric antibody formation, or humanization.

Analogs may be produced by a process of affinity maturation of 3C12F, 7D1G, 7D12A, 18V4F or 18P7E type monoclonal antibodies. Analogs generally selected for a higher binding affinity or a broader chemokine binding profile which may be acquired at the same time. Analogs may be easily identified by determining whether they bind to the same chemokines to which the parent antibodies bind, for example, by ELISA or other well-known assays. An analog includes those variants in which the heavy and light chains share about 90, 95, 99 or 100% sequence identity with the corresponding heavy and light chain sequences of 3C12F, 7D1G, 7D12A, 18V4F, or 18P7E. Affinity matured variants of antibodies produced by 3C12F, 7D1G, 7D12A, 18V4F or 18P7E hybridoma cell lines or subcultures thereof can be selected to have binding affinities of 1,000, 800, 400, 200, 100, 75, 50, 40, 30, 20, 10, 5, 1 or 0.1 nM or less. Some analogs or variants will have one, two, three, four, five, six, seven, ten, or up to twenty amino acid sequence modifications, such as deletions, insertions or substitutions, an analog can have about 2 to 10 amino acid substitutions in one or more hypervariable regions or CDRs of the 3C12F, 7D1G, 7D12A, 18V4F or 18P7E antibodies.

An analog may constitute an antibody, or antigen-binding fragment thereof, which binds two or more of MIP-1α, MIP-1β, RANTES, MCP-1 which comprises at least one of the following CDR combinations: CDR1 and CDR2; CDR1 and CDR3; CDR2 and CDR3; and CDR1, CDR2, and CDR3, of the 3C12F, 7D1G, 7D12A, 18V4F or 18P7E heavy chain and/or light chain variable regions.

Chimeric antibodies in which an animal antigen-binding variable domain is coupled to a human constant domain are well known in the art and methods for making them are incorporated by reference to Cabilly et al., U.S. Pat. No. 4,816,567; Morrison, S. L. et al., Proc. Natl. Acad. Sci. USA 81:6851-6855 (1984); Boulianne, G. L. et al., Nature 312:643-646 (1984); and Neuberger, M. S. et al., Nature 314:268-270 (1985).

The isotype of the human constant domain may be selected to tailor the chimeric antibody for participation in antibody-dependent cellular cytotoxicity (ADCC) and complement-dependent cytotoxicity (see e.g., Bruggemann, M. et al., J. Exp. Med. 166:1351-1361 (1987); Riechmann, L. et al., Nature 332:323-327 (1988); Love et al., Methods in Enzymology 178:515-527 (1989); Bindon, et al., J. Exp. Med. 168:127-142 (1988), which are incorporated by reference. Chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., Science 240:1041-1043 (1988).

The antikine antibodies of the invention may be humanized by known procedures including those disclosed by Carter, U.S. Pat. No. 6,719,971, Almagro, et al., Front. Biosci. 13:1619-1633 (2008); Pini, et al., Comb. Chem. High Throughput Screen. 5:503-510 (2002); and Wu, et al., J. Mol. Biol. 294:151-162 (1999) which are incorporated by reference. Humanization produces an immunoglobulin molecule with the antibody specificity of the donor animal (murine) antibody, but with reduced immunogenicity and better effector functions in humans. This process involves embedding known antikine CDR sequences into the light and heavy chain variable region framework sequences of a human antibody. In general, humanized antibodies are produced by substituting mouse CDRs into a human variable domain framework which is most likely to result in retention of the correct spatial orientation of the CDRs if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough, et al., Protein Engineering 4:773-783 (1991); Kolbinger, et al., Protein Engineering 6:971-980 (1993) and Carter, et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90%, 95% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid: noncovalently binds antigen directly, is adjacent to a CDR region, otherwise interacts with a CDR region (e.g., is within about 3-6 Å of a CDR region as determined by computer modeling), or participates in the VL-VH interface.

Residues which "noncovalently bind antigen directly" include amino acids in positions in framework regions which have a good probability of directly interacting with amino acids on the antigen according to established chemical forces, for example, by hydrogen bonding, van der Waals forces, hydrophobic interactions, and the like.

Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kalbat—Wu & Kabat, J. Exp. Med. 132:211-250 (1970)—or a CDR as defined by Chothia—Chothia & Lesk J. Mol. Biol. 196:901-917 (1987). These amino acids are particularly likely to interact with the amino acids in the CDRs and, if chosen from the acceptor, to distort the donor CDRs and reduce affinity. Moreover, the adjacent amino acids may interact directly with the antigen, Amit, et al., Science 233:747-753 (1986), which is incorporated herein by reference, and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to affect a CDR region. Residues that "otherwise interact with a CDR region" may be identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 Å of some atom in the CDRs and must contain an atom that could interact with the CDR atoms according to established chemical forces, such as those listed above.

Amino acids that are capable of interacting with amino acids in the CDRs may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 $Å^2$ or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art; e.g., Connolly, J. Appl. Cryst. 16:548 (1983) and Lee & Richards, J. Mol. Biol. 55:379 (1971), both of which are incorporated herein by reference. Framework amino acids may also occasionally interact with the CDRs indirectly, by affecting the conformation of another framework amino acid that in turn contacts the CDRs.

Residues which "participate in the VL-VH interface" or "packing residues" include those residues at the interface between VL and VH as defined, for example, by Novotny and Haber, Proc. Natl. Acad. Sci. USA 82:4592-66 (1985) or Chothia & Lesk, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, glu; asn, gln; ser, thr; lys, arg; and phe, tyr.

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criteria help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Wu & Kabat, supra). When deciding whether an amino acid in a human acceptor sequence is "rare" or "common" among human sequences, it will often be preferable to consider only those human sequences in the same subgroup as the acceptor sequence. Additional candidates for substitution are acceptor human framework amino acids that would be identified as part of a CDR region under the alternative definition proposed by Chothia & Lesk, supra.

Other candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence that enhances activity. Unusual residues that are predicted to affect binding are retained, whereas residues predicted to be unimportant for binding can be substituted.

More candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

In some embodiments, humanized antibodies preferably exhibit a specific binding affinity for antigen similar to or higher than that of the mouse antibody from which they were constructed. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor framework regions, but no framework region substitutions). In such instances, the binding of the antibody (with substitutions) is preferably at least two- to three-fold greater, or three- to four-fold greater, than that of the unsubstituted antibody. For making comparisons, activity of the various antibodies can be determined, for example, by BIAcore® (i.e., surface plasmon resonance using unlabelled reagents) or competitive binding assays.

An engineered antibody may be designed based on the sequences of the monoclonal antibodies disclosed herein using standard affinity maturation techniques, such as those described Wu, et al., J. Mol. Biol. 350: 126-144 (2005) (incorporated by reference) in order to increase the affinity of the antibody to the originally identified chemokines and/or broaden the chemokine selectivity to other CC-chemokines which may also be involved in inflammatory diseases.

The class or isotype or subclass (e.g., IgG1, IgG2, IgG3 or IgG4) may be selected, particular for chimeric, humanized or engineered antibody products to target or adapt the antibody to a particular function well known for the selected class or subclass. For example, human IgG2 can be selected to minimize passage of the antibody product across the placenta or minimize Fc-receptor interaction with other components a subject's immune system, and subclass IgG4 to minimize the ability of the antibody product to activate complement. IgA isotype can be selected to produce a secretory antibody and a pentameric IgM antibody product to enhance binding of the antibody compared to monomeric antibodies. The functions of various classes and subclasses of antibody molecules are incorporated by reference to Kuby, *Immunology*, WH Freeman (1997).

Single-chain Fv" or "sFv" antibody fragments comprise the $V_H$ and $V_L$ domains of an antikine antibody, wherein these domains are present in a single polypeptide chain. Generally, the Fv polypeptide further comprises a polypeptide linker between the $V_H$ and $V_L$ domains which enables the sFv to form the desired structure for antigen binding; see Plückthun in *The Pharmacology of Monoclonal Antibodies*, vol. 113, Rosenburg and Moore eds., Springer-Verlag, New York, pp. 269-315 (1994) which is incorporated by reference. Single-chain antibodies specific to CC chemokines may be produced by known methods such as those disclosed by U.S. Pat. No. 4,946,778 which is incorporated by reference.

"Diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. The antikine antibodies of the invention may be formulated as diabodies which can be made by procedures incorporated by reference to EP 404,097; WO 93/11161; and Hollinger et al., Proc. Natl. Acad. Sci. USA 90:6444-6448 (1993).

"Linear antibodies" refers to the antibodies described in Zapata et al. Protein Eng. 8(10): 1057-1062 (1995). Briefly, these antibodies comprise a pair of tandem Fd segments ($V_H$-$C_H1$-$V_H$-$C_H1$) which form a pair of antigen binding regions. Linear antibodies can be bispecific or monospecific. The antikine antibodies of the invention may be produced according to the procedures described by Zapata, et al., which are hereby incorporated by reference.

Fab expression libraries may be constructed by other conventional methods such as those disclosed by and incorporated by reference to Huse et al., Science 246:1275-1281 (1989) to allow rapid and effective identification of monoclonal Fab fragments with the desired specificity for CC chemokines or derivatives, fragments, analogs or homologs thereof.

Unique portions of the antibodies exemplified below, such as their CDR sequences and sequences containing a portion of a CDR, may be used to produce anti-idiotype antibodies. These antibodies recognize one or more idiotypes on a variable segment of an antikine antibody and can be used to identify or purify an antikine antibody or modulate its activity. Such anti-idiotype antibodies can be produced by procedures known in the art, such as by conjugation of a variable peptide sequence of an antibody to an immunogenic carrier and repeated immunization. Such methods are also incorporated by reference to Cavenaugh, et al., Pharm. Res. 21:1480-1488 (2004).

An anti-idiotypic antibody is an antibody that recognizes determinants of another antibody (a target antibody). Generally, the anti-idiotypic antibody recognizes determinants of the antigen-binding site of the target antibody. Typically, the target antibody is a monoclonal antibody. An anti-idiotypic antibody is generally prepared by immunizing an animal (particularly, mice) of the same species and genetic type as the source of the target monoclonal antibody, with the target monoclonal antibody. The immunized animal mounts an immune response to the idiotypic determinants of the target monoclonal antibody and produces antibodies against the idiotypic determinants of the target monoclonal antibody. Antibody-producing cells, such as splenic cells, of the immunized animal may be used to generate anti-idiotypic monoclonal antibodies. Furthermore, an anti-idiotypic antibody may also be used to immunize animals to produce anti-anti-idiotypic antibodies. These immunized animals may be used to generate anti-anti-idiotypic monoclonal antibodies using standard techniques. The anti-anti-idiotypic antibodies may bind to the same epitope as the original, target monoclonal antibody used to prepare the anti-idiotypic antibody. The anti-anti-idiotypic antibodies represent other monoclonal antibodies with the same antigen specificity as the original target monoclonal antibody.

If the binding of the anti-idiotypic antibody with the target antibody is inhibited by the relevant antigen of the target antibody, and if the anti-idiotypic antibody induces an antibody response with the same specificity as the target antibody, it mimics the antigen of the target antibody. Such an anti-idiotypic antibody is an "internal image anti-idiotype" and is capable of inducing an antibody response as if it were the original antigen, see Bona and Kohler, *Anti-idiotypic Antibodies and Internal Image in Monoclonal and Anti-idiotypic Antibodies: Probes for Receptor Structure and Function*, Venter J. C., Frasser, C. M., Lindstrom, J. (Eds.), Alan R. Liss, N.Y., pp 141-149 (1984). Vaccines incorporating internal image anti-idiotype antibodies have been shown to induce protective responses against viruses, bacteria, and parasites; Kennedy, et al. Science 232:220-223 (1986); McNamara, et al., Science 226:1325-1326 (1985). Internal image anti-idiotypic antibodies have also been shown to induce immunity to tumor related antigens; Raychauhuri, et al., J. Immunol. 137: 1743-1749 (1986); Raychauhuri et al., J. Immunol. 139: 3902-3910 (1987); Bhattacharya-Chatterjee et al., J. Immunol. 139:1354-1360 (1987); Bhattacharya-Chatterjee, et al., J. Immunol. 141:1398-1403 (1988). The teachings of the documents cited in this paragraph are incorporated by reference.

Anti-idiotypic antibodies for CC chemokines may be prepared, for example, by immunizing an animal, such as a mouse, with a immunogenic amount of a composition comprising CC-chemokines or immunogenic portions thereof, containing at least one antigenic epitope of CC-chemokines. The composition may also contain a suitable adjuvant, and any carrier necessary to provide immunogenicity. Monoclonal antibodies recognizing CC-chemokines may be prepared from the cells of the immunized animal as described above. A monoclonal antibody recognizing a common epitope of CC chemokines is then selected and used to prepare a composition comprising an immunogenic amount of the anti-CC-chemokine monoclonal antibody. Typically, a 25 to 200 µg dose of purified CC-chemokine monoclonal would be sufficient in a suitable adjuvant. Animals may be immunized 2-6 times at 14 to 30 day intervals between doses. Typically, animals are immunized by any suitable route of administration, such as intraperitoneal, subcutaneous, intravenous or a combination of these. Anti-idiotypic antibody production may be monitored during the immunization period using standard immunoassay methods. Animals with suitable titers of antibodies reactive with the target monoclonal antibodies may be re-immunized with the monoclonal antibody used as the immunogen three days before harvesting the antibody producing cells. Preferably, spleen cells are used, although other antibody producing cells may be selected. Antibody-producing cells are harvested and fused with myeloma cells to produce hybridomas, as described above, and suitable anti-idiotypic antibody-producing cells are selected.

Anti-anti-idiotypic antibodies are produced by another round of immunization and hybridoma production by using the anti-idiotypic monoclonal antibody as the immunogen.

As described above, the variable segments of antikine antibodies, such as CDR segments, or peptide fragments of variable segments, including fragments having 3, 4, 5, 6, 7, 8, 9, 10, 11, 12 or more contiguous amino acid residues, especially those that have binding activity for chemokines, may be used for a number of applications in addition to therapeutic treatment of autoimmune diseases, including as peptide-based pharmaceutical agents, vaccines, production of anti-idiotype antibodies, or as immunogens. Another aspect of the present invention is directed to methods of inducing an immune response in a mammal against a polypeptide of the invention by administering to the mammal an amount of the polypeptide preparation sufficient to induce an immune response. The amount will be dependent on the animal species, size of the animal, and the like but can be determined by those skilled in the art.

The invention also includes antibodies or antibody fragments derived from chimeric or humanized antikine antibodies through the process of affinity maturation. Amino acid substitutions within the CDRs may be identified which significantly improve the affinity of the antibody for CC-chemokines and are therefore included herein. Methods for affinity maturation are described for example in Wu et al., Proc. Natl. Acad. Sci. USA 95:6037-6042 (1998) and by Clackson and Loman, *Phage Display*, Oxford University Press (2004) each of which is also incorporated by reference.

Anti-CC chemokine antikine antibodies may be used in methods known within the art relating to the localization and/or quantification of a CC-chemokines (e.g., for use in measuring levels of CC-chemokines within appropriate physiological samples, for use in diagnostic methods, for use in imaging the protein, and the like). In a given embodiment, antibodies for CC-chemokines, or derivatives, fragments, analogs or homologs thereof, that contain the antibody derived binding domain, are utilized as pharmacologically-active compounds, drugs or therapeutic compounds.

An anti-CC-chemokine antikine antibody (e.g., monoclonal antibody) can be used to isolate CC-chemokines by standard techniques, such as affinity chromatography or immunoprecipitation. An anti-CC-chemokine antibody can facilitate the purification of natural CC-chemokines from cells and of recombinantly produced CC-chemokines expressed in host cells. Moreover, an anti-CC-chemokine pan-antibody can be used to detect CC-chemokines (e.g., in a cellular lysate or cell supernatant) in order to evaluate the abundance and pattern of expression of the CC-chemokines. Anti-CC-chemokine antikine antibodies can be used diagnostically to monitor protein levels in tissue as part of a clinical testing procedure in order to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, and $^{3}$H.

In addition, the antibodies of the present invention may be conjugated to toxins such as radioisotopes, protein toxins and chemical toxins which may be conjugated to antibodies. Such toxins include, but are not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, Boron-10, Actinide, ricin, adriamycin, calicheamicins, 5-fluorouracil, auristatins, and maytansinoids.

Chimeric, humanized, and human antibodies as well as antigen-binding fragments thereof are typically produced by recombinant expression. Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences, see, e.g., Itakura, et al., U.S. Pat. No. 4,704,362, which is incorporated by reference. *E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding immunoglobulins or fragments thereof). See Winnacker, *From Genes to Clones*, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer, Queen et al., Immunol. Rev. 89:49-68 (1986), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co, et al., J. Immunol. 148:1149-1154 (1982), each of the above documents is incorporated by reference.

Alternatively, antibody-coding sequences can be incorporated in transgenes for introduction into the genome of a transgenic animal and subsequent expression in the milk of the transgenic animal, as described for example by Deboer, et al., U.S. Pat. No. 5,741,957, Rosen, U.S. Pat. No. 5,304,489, and Meade, et al., U.S. Pat. No. 5,849,992, each of which is incorporated by reference. Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences or fragments thereof and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see generally, Sambrook, et al., supra). For production of transgenic animals, transgenes can be microinjected into fertilized oocytes, or can be incorporated into the genome of embryonic stem cells, and the nuclei of such cells transferred into enucleated oocytes. All of these methods are incorporated by reference to Sambrook, et al., *Molecular Cloning: A Laboratory Manual* (Cold Spring Harbor Press, 2nd ed. (1989).

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms may be purified according to standard procedures of the art, including by use of ammonium sulfate precipitation, affinity columns, column chromatography, HPLC purification, gel electrophoresis and other similar procedures including those disclosed by Scopes, *Protein Purification*, Springer-Verlag, N.Y. (1982) which is incorporated by reference. For pharmaceutical use, it is desirable to employ substantially pure immunoglobulins having a degree or purity and/or homegeneity of at least 90 to 95%, or even 98 to 99%.

Fragments of, or truncated, antikine antibodies, such as Fab fragment, Fab' fragment, a F(ab')$_2$ fragment, and F$_v$ fragment, as well as single antibody chains comprising individual light and/or heavy chain CDRs involved in chemokine binding may be used to bind to or neutralize one or more CC chemokines.

Antikine antibodies may be chemically modified or derivatized to provide a desired effect.

An antibody conjugate or conjugated antibody may be made using antikine antibody or its fragment joined via peptide bonds to a heterologous protein. In such embodiments, the antigen-binding portion of the antibody binds MIP-1α, MIP-1β, RANTES, MCP-1, and/or other related CC-chemokines. Antikine antibodies may also be conjugated to enzymes, toxins or a cytokine as effector moieties. They may also contain or be further conjugated or covalently linked to accessory moieties such as chemical or radiological tags, toxins, biologically active or targeting moieties, or other substances which increase their biological half lives or biological availability, such as by conjugation to polyethylene glycol or albumin. An antikine antibody of the invention may contain or be conjugated to an accessory moiety, such as those disclosed by Carter and Senter, Cancer J. 14: 154-169 (2008) which is incorporated by reference. The antibodies and antibody products of the invention can be immobilized to a solid substrate or immunoaffinity resin such as those described by *Antibodies: A Laboratory Manual*; Eds. E. Harlow & D. Lane, (1988) which is incorporated by reference.

Pegylation of antibodies and antibody fragments of the invention may be carried out by any of the pegylation reactions known in the art, as described, for example, in the following references: Focus on Growth Factors 3:4-10 (1992); EP 0 154 316; and EP 0 401 384, each of which is incorporated by reference herein in its entirety. Preferably, the pegylation is carried out via an acylation reaction or an alkylation reaction with a reactive polyethylene glycol (PEG) molecule (or an analogous reactive water-soluble polymer). A preferred water-soluble polymer for pegylation of the antibodies and antibody fragments of the invention is PEG. As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with PEG, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat conditions that may be alleviated or modulated by administration of the antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In other embodiments of the invention the antibodies or antigen-binding fragments thereof are conjugated to albumin using techniques recognized in the art.

In another embodiment of the invention, antibodies, or fragments thereof, are modified to reduce or eliminate potential glycosylation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis (see http://www.cbs.dtu.dk/services/NetNGlyc/ for predicting N-linked glycoslyation sites and http://www.cbs.dtu.dk/services/NetOGlyc/ for predicting O-linked glycoslyation sites). Additional methods for altering glycosylation sites of antibodies are described in U.S. Pat. Nos. 6,350,861 and 5,714,350 which are incorporated by reference.

In yet another embodiment of the invention, antibodies or fragments thereof can be altered by modifying the constant region of the antibody to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions, see e.g., Canfield, S. M. and S. L. Morrison, J. Exp. Med. 173:1483-1491 (1991); and Lund, J. et al., J. Immunol. 147:2657-266 (1991) all of which are incorporated by reference. Reduction in FcR binding ability of the antibody may also reduce other effector functions which rely on FcR interactions, such as opsonization and phagocytosis and antigen-dependent cellular cytotoxicity. Constant region derivatives to enhance or reduce antibody effector functions and to reduce or extend serum persistence are described by Carter, P. J., Nat. Rev. Immunol. 6:343-357 (2006) which is incorporated by reference.

The antikine antibodies of the invention may be incorporated into pharmaceutical compositions such as those described above or in compositions used to store, preserve or administer the antibodies to subjects in need of treatment.

Kits for use in the therapeutic or diagnostic applications above, may contain one more antikine antibodies, positive or negative control antibodies, CC chemokines bound by antikine antibodies, control chemokines not bound by the antikine antibody, as well as other pharmacological or diagnostic components and written instructions regarding the use of the kit.

Antibodies or antigen-binding fragments of the invention are useful for, e.g., therapeutic purposes (by modulating activity of CC-chemokines), diagnostic purposes to detect or quantify CC-chemokines, and purification of CC-chemokines. Therefore, kits comprising an antibody of the invention for any of the purposes described herein are also within the scope of the invention.

The CC chemokines, particularly MIP-1α, MIP-1β, RANTES, and/or MCP-1 have been shown to play a role in pathological conditions associated with inflammation. MIP-1α, MIP-1β, RANTES, and/or MCP-1 have all been shown to have potent chemotactic activity for leukocytes, especially monocytes and T lymphocytes. These pathological conditions include those described by Johnson et al., Trends Immunol. 26:268-274 (2005) which is hereby incorporated by reference.

MIP-1α, MIP-1β, RANTES, and/or MCP-1 are molecules with potent chemotactic activity for monocytes and T lymphocytes. Given their overlapping activities and the increased expression of all four of these chemokines in human disease, blockade of two, three or four CC chemokine molecules is expected to have a greater beneficial effect than just inhibition of a single CC chemokine alone. Accordingly, the antibodies and antibody fragments of the invention are useful to modulate the activity of these chemokines and affect the pathology of disorders associated with these chemokines. As such, these antibodies and fragments are useful in therapeutic compositions for the treatment of inflammatory conditions and pathological conditions associated with expression of CC-chemokine molecules. In these embodiments, a patient is identified as having one of the diseases to be treated, such as by exhibiting at least one sign or symptom of the disease or disorder. At least one antibody or antigen-binding fragment thereof of the invention or compositions comprising at least one antibody or antigen-binding fragment thereof of the invention is administered in a sufficient amount to alleviate at least one symptom of the disease or disorder, or to reduce the activity of at least one of MIP-1α, MIP-1β, RANTES, and/or MCP-1.

Disorders Amenable to Prevention or Treatment. As used herein, the terms "a disorder in which CC chemokine activity is detrimental" and "a CC-chemokine-associated disorder" are intended to include diseases and other disorders in which the presence of a CC-chemokine, including MIP-1α, MIP-1β, RANTES, MCP-1 and other CC-chemokines, in a subject suffering from the disorder has been shown to be or is suspected of being either responsible for the pathophysiology of the disorder or a factor that contributes to the disorder. Accordingly, a disorder in which CC-chemokine activity is detrimental is a disorder in which inhibition of CC-chemokine activity is expected to prevent or alleviate the symptoms and/or progression of the disorder. Such disorders may be evidenced, for example, by an increase in the concentration of CC-chemokines in a biological fluid of a subject suffering from the disorder, e.g., an increase in the concentration of RANTES in serum, plasma, synovial fluid, urine, etc. of the subject, which can be detected, for example, using an anti-RANTES antibody. There are numerous examples of disorders in which CC-chemokine activity is detrimental. The use of the antibodies and antibody portions of the invention in the prevention or treatment of specific disorders is discussed further below.

Rheumatoid arthritis (RA) is characterized by an influx of leukocytes, including T and B lymphocytes, macrophages, and neutrophils, into the synovial lining of joints; see the review by Koch, Arthritis Rheum. 52: 710-721 (2005). MIP-1α is found in high levels in synovial fluid of RA patients and the increased levels correlate with severity of disease. Similarly in rodent murine models of RA high levels of murine MIP-1α are found in arthritic joints. Neutralizing antibodies decrease arthritic scores in a collagen-induced arthritis model by approximately 50%; Kasama, et al., J. Clin. Invest. 95: 2868-2876 (1995).

The levels of RANTES are also increased in joints in a rodent adjuvant-induced model of arthritis. Antibodies to RANTES reduced symptoms in this model; Barnes et al., J. Clin. Invest. 101: 2910-2919 (1998).

MCP-1 has also been shown to be produced by synovial cells and infiltrating leukocytes in RA patients. Neutralizing antibodies to MCP-1 also reduced the clinical score in a rodent model of arthritis; Ogata, et al., J. Pathol. 182: 106-114 (1997).

Multiple sclerosis (MS) is characterized by a breakdown of the myelin sheath around the nerves and by an influx of leukocytes into the nervous tissue. High levels of chemokines including MIP-1α, RANTES, and MCP-1 are found in brain lesions of MS patients; Sorensen, et al., J. Clin. Invest. 103: 807-815 (1999).

Experimental autoimmune encephalitis (EAE) is a disease model that closely mimics human MS. MIP-1α and MCP-1 have both been implicated in the induction of disease symptoms and in development of relapses, as shown with neutralizing antibodies; Kennedy, et al., J. Neuroimmunol. 92: 98-108 (1998).

Fibrotic disease includes any condition marked by an increase of interstitial fibrous tissue. CC-chemokines are known to be associated with fibrotic conditions. For example levels of MCP-1, MIP-1α and MIP-1β are all elevated in patients with systemic sclerosis and high levels of CC-chemokines correlated with development of lung fibrosis in these patients; Hasegawa et al., Clin. Exp. Immunol. 117: 159-165 (1999).

Atherosclerosis is characterized by vascular lipid deposits with high infiltration of macrophages. MCP-1 knockout mice show a marked decrease in macrophages and lipid deposition in a murine model of atherosclerosis; Gu, et al., Mol. Cell. 2: 275-281 (1998).

Asthma patients have marked infiltration of leukocytes and increased levels of CC-chemokines in the lungs leading to airway hyper responsiveness. In rodent models of asthma neutralizing antibodies to MIP-1α, MCP-1 or RANTES decreased the inflammation and/or the airway hyper reactivity typical of this disease; Lukacs, et al., J. Immunol. 158: 4398-4404 (1997).

The animal models described in the documents above may be used to evaluate the efficacy of antikine antibodies in treating the associated condition, disorder or disease and these models and methods of their use are incorporated by reference to the documents above.

Besides the diseases highlighted above, numerous other conditions, disorders and diseases have been associated with the activity of one or more chemokines, these include but are not limited to: oncogenic diseases, inflammatory bowel diseases, atopic dermatitis, psoriasis, stroke, organ transplantation, COPD, glomerulonephritis, lupus nephritis, scleroderma, cirrhosis, Alzheimer's disease, CHF-ischemia, coronary restenosis, diabetic nephropathy/neuropathy/retinopathy, osteoarthritis, periodontitis, yeast and viral infections, and dysregulation of pregnancy. When CC chemokines play a role in these pathologies, an antikine antibody may be administered to reduce the severity of these conditions.

Such methods generally involve administering an amount of an antikine antibody usually in a pharmaceutically acceptable carrier to a subject, such as an animal or human, in need thereof. The amount of antikine antibody or a truncated version or fragment thereof is selected so as to inhibit the activity of one or more chemokines in the subject. Similar methods may be performed ex vivo on biological materials (e.g., blood, bone marrow, organic tissue) removed from a subject or on biological materials maintained in vitro.

Antikine antibodies may be used to block chemotaxis. Such methods comprise admixing or contacting an antikine antibody with a medium containing CC chemokines to which the antikine antibody binds or a medium containing cells producing these CC chemokines.

Diagnostic assays can usefully employ the antikine antibodies of the invention. Such assays involve contacting an antikine antibody having known specificities for CC chemokines with a biological sample suspected of containing at least one chemokine to which the antikine antibody binds and determining the amount of binding, for example, by measurement of complex formation. The antikine antibodies may be used in free or substrate bound form. The invention further provides in vitro immunoassays for detecting CC-chemokines in samples.

The antibodies and antibody fragments of the invention may be used to detect CC-chemokines in samples using a variety of well-known immunological assays. The antibodies may be used, for example, in ELISAs, Western blots, radioimmunoassays, immunoprecipitaton, immunoaffinity chromatography, immunostaining of tissue sections, immunogold detection in tissue samples with electron microscopy, and the like. The protocols for these and other assays are well-known in the art and are well within the purview of the skilled artisan.

The immunoassays using the antibodies and antibody fragments of the invention may be used to detect the presence and relative amounts of CC-chemokines in a sample. Samples may include, but are not limited to, homogenized tissue or cells, histological tissue sections for light and electron microscopy, protein extracts of tissue or cells, csf, joint fluid, blood, plasma, serum, mucosal secretions, semen, vaginal fluids, tears, saliva, sweat, urine, feces and the like. The presence of increased amounts of a CC-chemokine(s) relative to normal samples, for example, may indicate the presence of a disease state, and treatment with a therapeutic of the invention may be indicated. In some instances, there may be a decreased amount of CC-chemokine(s) relative to normal samples, and treatment with appropriate CC-chemokine(s) or internal image antibodies that mimic CC-chemokine(s) may be used to stimulate immune function.

In some embodiments, an immunoassay may be used to aid in the purification of CC-chemokines. For example, an immunoaffinity resin may be used in which the antibodies or antibody fragments of the invention are immobilized on a substrate. A sample containing the CC-chemokine(s) is added to the immunoaffinity resin and the antibodies become bound to the resin, while other components of the sample remain in solution. The resin is washed and the CC-chemokines are subsequently eluted from the resin, substantially purified and isolated. Preferably, the antibodies used in the immunoassay will have high binding affinity, as defined herein.

EXAMPLES

This invention is further illustrated by the following examples which should not be construed as limiting. The contents of all references, patents and published patent applications cited throughout this application, as well as the figures and the Sequence Listing, are incorporated herein by reference.

Example 1

Production of Hybridomas Producing Antikine Antibodies

Mice were immunized sequentially with three CC-chemokines, in random order, from the set that initially included MIP-1α, RANTES and MCP-1 (PeproTech). For hybridoma fusion 3, which produced MAb 3C12F, the mouse was initially immunized with MIP-1α, followed by boosts with RANTES, then MCP-1, then MCP-1 again. For hybridoma fusion 7, which produced MAbs 7D12A and 7D1G, the mouse was initially immunized with MIP-1α, followed by boosts with MCP-1, then RANTES, then a combination of MIP-1α and RANTES. For hybridoma fusion 18, which produced MAbs 18V4F and 18P7E, mice were immunized initially with MIP-1β, followed by boosts with MIP-1α, then RANTES, then another boost with RANTES.

For each immunization 10 μg protein was used, following standard immunization protocols, see Current Protocols in Immunology, Eds. JE Coligan, et al. (2006), section 2.1. The initial immunizations were done in Complete Freund's Adjuvant, followed by 3 week interval boosts of two different chemokines in Incomplete Freund's Adjuvant.

Ten days after the final boost serum was collected and tested for reactivity with CC-chemokines MIP-1α, RANTES, MCP-1 and MIP-1β by ELISA as described by Current Protocols in Immunology, 2006, Eds. JE Coligan et al., section 2.4, which is incorporated by reference. For MIP-1α, the chemokine was coated on a 96-well ELISA plate (at 1 μg/mL) and incubated with serum at a range of dilutions from 1:50 to 1:6400. For RANTES, MCP-1 and MIP-1β, biotinylated chemokines (0.5 μg/mL) were added to streptavidin-coated plates (Pierce) and then incubated with diluted sera. Antibody bound to coated chemokines was detected using an anti-mouse Fc secondary antibody conjugated to HRP.

Biotinylation of chemokines for ELISA assays was performed using sulfo-NHS-LC-biotin (Pierce). Chemokine in PBS was mixed with approximately 2-fold molar excess of sulfo-NHS-LC-biotin and incubated at room temperature for 30 min. Free biotin reagent was removed by dialysis in PBS overnight using Slide-a-lyzer mini dialysis units with 3,500 MW cutoff (Pierce).

Results of ELISAs on serum from the initial set of immunizations using MIP-1α, RANTES and MCP-1 showed a variety of responses (see Table 1), including some responses to MIP-1β even though it was not used as a direct immunogen. Several mice had responses to 3 and even 4 chemokines. These were candidates for hybridoma fusions to look for single antibodies that reacted with multiple chemokines. As shown in Table 1 below, immunized mice produced polyclonal sera which reacted with multiple CC chemokines.

TABLE 1

Serum reactivities of immunized mice

| Mouse | MCP-1 | RANTES | MIP-1α | MIP-1β | Immunization sequence |
|---|---|---|---|---|---|
| A1 |  |  | + |  | MIP-1α → |
| A2 |  | + |  |  | RANTES → |
| A3 | + |  | + |  | MCP-1 |
| A4 | + | + | + |  |  |
| A5 | + | + | + | + |  |
| B1 | + | + | + | + | MIP-1α → |
| B2 | + | +/− |  |  | MCP-1 → |
| B3 | + | +/− | + | +/− | RANTES |
| B4 | + |  | + |  |  |
| B5 |  | + | + |  |  |
| C1 | + | + | + | +/− | RANTES → |
| C2 | +/− | + | + |  | MIP-1α → |
| C3 |  | + | +/− |  | MCP-1 |
| C4 |  | + | +/− |  |  |
| C5 | + | + |  |  |  |
| D1 |  | + |  |  | RANTES → |
| D2 |  | + |  |  | MCP-1 → |
| D3 | + | + | + |  | MIP-1α |
| D4 | + | + |  |  |  |
| D5 |  | + |  |  |  |
| E1 | + |  | + |  | MCP-1 → |
| E2 | + | + | + | +/− | MIP-1α → |
| E3 | + |  | + |  | RANTES |
| E4 | + | +/− | +/− |  |  |
| E5 | + | + | + |  |  |
| F1 | + | + | + |  | MCP-1 → |
| F2 |  | +/− |  |  | RANTES → |
| F3 |  |  |  |  | MIP-1α |
| F4 | + |  | +/− |  |  |
| F5 | + |  |  |  |  |

Mice showing significant serum reactivity with at least 3 target chemokines were selected for hybridoma fusions; see Antibodies: A Laboratory Manual, Eds. E. Harlow & D. Lane (1988), chapter 6.

A chosen mouse was boosted with a mixture of chemokines (20 μg each) in PBS at days −4 and −3 before harvesting the spleen for fusion with NS1 cells to create hybridomas. A single cell suspension was made from the spleen by pressing between the frosted ends of two slides and collecting the cells in 10 mL RPMI. Cells were passed through a 70 μm nylon strainer, rinsed with 10 mL additional RPMI, and pelleted at 300×g for 5 min. Cells were washed and centrifuged 2 more times and then counted. Spleen cells were combined with NS1 cells (ATCC) at a ratio of 5:1 spleen:NS1 and then pelleted. One mL 50% PEG was added dropwise to the pelleted cells over 1 min with swirling, then the mixture was swirled an additional 1 min. An additional 1 mL RPMI was added over 1 min with swirling, then another 3 mL RPMI was added over 1 min with swirling, then another 16 mL RPMI was added over 2 min with swirling. Cells were pelleted at 300×g for 10 min and resuspended in 800 mL hybridoma selection medium. The cells were rested for 2 hours and then distributed over 40 96-well plates at 200 μL/well. Plates were placed in 37° C. incubator and fed every 2-3 days over the next 8-10 days by removing and replacing half the volume of medium. Alternatively, fused cells were suspended in methylcellulose-based semi-solid medium CloneMatrix (Genetix) containing CloneDetect (Genetix) plus Alexa488-tagged MIP-1α at 4 μg/mL and plated in single-well 10 cm plates (Genetix).

Example 2

Identification of Antikine Antibodies

Antibodies in the hybridoma supernatant obtained in Example 1 were tested for their ability to recognize MIP-1α, RANTES, MCP-1 and MIP-1β by ELISA (similar to serum tests described above). ELISA results for initial hybridoma supernatants are shown in Table 2 below. Cells from fusion wells that showed reactivity of at least 4-fold over background with more than one chemokine were expanded into 24-well plates for further testing. Cells from wells that reacted with at least 3 chemokines were cloned by limiting dilution or by serial dilution at least two times. Clone plate supernatants were again tested by ELISA to identify individual clones that produced antibody reactive against multiple chemokines. Positive wells were confirmed to be clonal by visual inspection.

Alternatively, hybridomas grown as colonies in semi-solid media were analyzed after 16 days for growth and fluorescent chemokine binding using ClonePixFL (Genetix), and the best colonies were picked into 96-well plates. Antibody-containing supernatants from the hybridoma clones were analyzed after 4 days for reactivity by ELISA with MIP-1α (both directly coated and biotinylated), RANTES and MIP-1β as described above for serum analysis. Clones 18V4F and 18P7E showed significant reactivity with all 3 CC-chemokines. These were re-cloned by serial dilution to confirm clonality and again tested by ELISA to confirm production of antikine antibodies exhibiting multi-chemokine reactivity.

TABLE 2

ELISA signals from original hybridoma fusion wells for antikine monoclonal antibodies.

a) ELISA signals for 3C12F, 7D1G, and 7D12A antibodies

|  | 3C12F | 7D1G | 7D12A | Background (approx.) |
|---|---|---|---|---|
| MIP-1α | 1.84 | 1.70 | 1.47 | 0.150 |
| Biotin-RANTES | 2.61 | 0.145 | 0.178 | 0.150 |
| Biotin-MCP1 | 0.189 | 0.220 | 0.246 | 0.150 |
| Biotin-MIP-1β | 1.92 | 2.57 | 2.68 | 0.150 | b) ELISA signals for 18V4F and 18P7E antibodies

|  | 18V4F | 18P7E | Background |
|---|---|---|---|
| Biotin-MIP-1α | 1.674 | 1.001 | 0.040 |
| Biotin-RANTES | 0.909 | 0.462 | 0.030 |
| Biotin-MIP-1β | 1.699 | 1.603 | 0.075 |

Example 3

Characterization of Chemokine Binding Specificities of Antikine Antibodies

A more complete analysis of the chemokine binding specificities for the isolated antikine antibodies was performed using an MSD (Meso Scale Discovery) assay. This is very similar to the ELISA assays done during antibody screening, however it uses electrochemiluminescence detection of SULFO-TAG reagents. In this case, a selection of chemokines is coated at 1 μg/mL on an MSD 96-well multiarray plate (MA2400). Antikine antibodies are added either at 3 μg/mL (purified antibodies 3C12F, 7D 12A, 7D 1 G, 18V4F) or as unquantitated hybridoma antibody-containing supernatant (18P7E) and are detected with a SULFO-TAG anti-murine antibody used at 1 μg/mL. Plates are read on an MSD sector imager 2400. Background levels shown as dotted lines in the Figures are based on binding to a non-reactive protein, bovine serum albumin (BSA).

Example 4

Examination of the Functional Activities of Antikine Antibodies

Supernatants from expanded fusion wells obtained in Example 2 were tested for ability to block chemotaxis mediated by a target chemokine. This was tested in vitro using CCR2 transfectants (receptor for MCP-1) or CCR5 transfectants (receptor for MIP-1α, RANTES and MIP-1β) in 96-well transwell plates (Millipore). In the lower well of each transwell chamber, 75 μL of chemokine solution (10 ng/mL in RPMI with 2% FBS) was mixed with 75 μL hybridoma supernatant. In the upper well of each chamber $4 \times 10^5$ cells were added in 75 μL RPMI with 2% FBS. Cell migration was allowed to occur for 2 hours at 37° C., then the number of cells in the lower chamber was quantitated by cell counting using the FACScalibur. Cells from hybridoma wells that showed inhibition of at least 2 chemokines were then also cloned by serial dilution. Purified antibodies were tested similarly for inhibition of chemotaxis at a range of concentrations.

Chemokine receptor transfectants used in chemotaxis assays were generated using Ba/F3 cells (obtained from the German Collection of Microorganisms and Cell Cultures—DSMZ). The open reading frames of human CCR2 and CCR5 were amplified by PCR (see *Molecular Cloning: A Laboratory Manual*, Eds. Sambrook et al.) from cDNA clones purchased from Origene. The PCR primers were designed from published sequences. The 5' primer overlapped the initiating Met codon and contained an XhoI cloning site. The 3' primer overlapped the termination codon and contained an XbaI cloning site. The amplified fragment was digested with XhoI and XbaI and inserted into the equivalent sites in the expression plasmid pNEF38 (Running Deer & Allison, Biotechnol Prog 20, 880-889, 2004). Ba/F3 cells were transfected with the expression plasmids by electroporation (Amaxa) and selected in G418. Cells expressing functional receptor were selected through chemotaxis to the cognate chemokine ligands, and migrating cells were cloned by limiting dilution to obtain a stable cell clone.

Example 5

Identification and Characterization of Antikine Antibodies

Five unique monoclonal antibodies that recognized multiple CC chemokines were identified and designated 3C12F, 7D1G, 7D12A, 18V4F and 18P7E. The isotypes of the antibodies were determined using IsoStrips (Roche). The 3C12F heavy chain was determined to be a member of murine subgroup IgG1, while the 3C12F light chain was determined to be a member of murine κ group. The 7D1G heavy chain was determined to be a member of murine subgroup IgG1, while the 7D1G light chain was determined to be a member of murine κ group. The 7D12A heavy chain was determined to be a member of murine subgroup IgG1, while the 7D12A light chain was determined to be a member of murine κ group. The 18V4F heavy chain was determined to be a member of murine subgroup IgG2a, while the 18V4F light chain was determined to be a member of murine λ. The 18P7E heavy chain was determined to be IgG1 and its light chain was also found to be murine λ.

Figure 2:
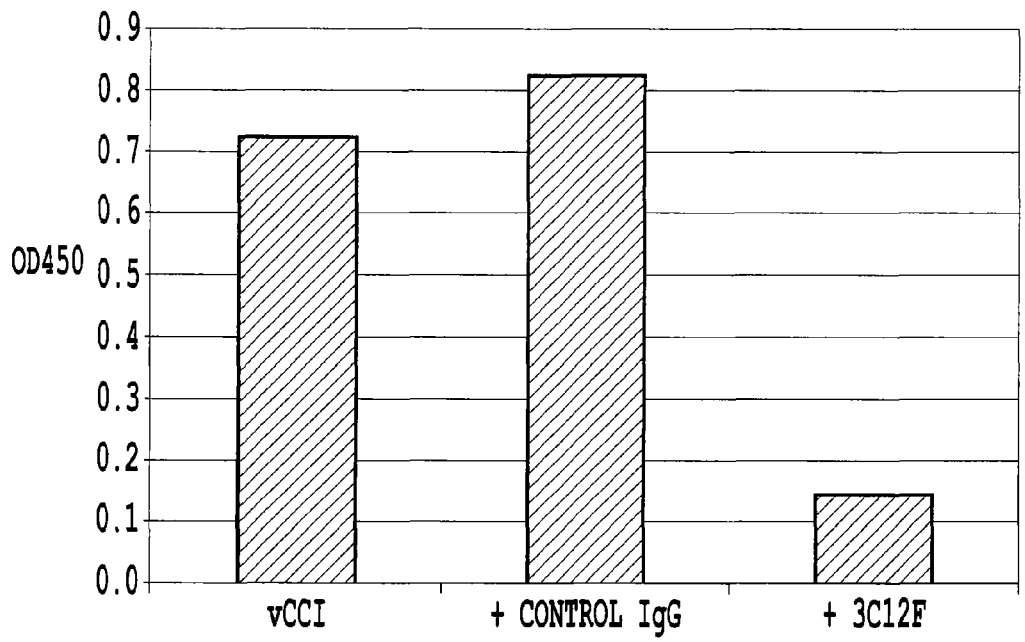
FIG. 2 shows that 3C12F blocks vCCI binding to RANTES/CCL5.
Figure 3:
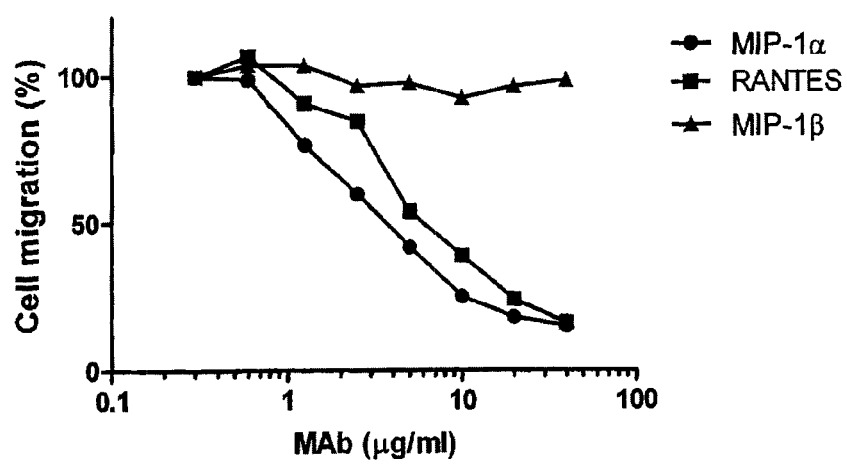
FIG. 3 shows titration of inhibitory activity of purified 3C12F in chemotaxis assays

MAb 3C12F recognized MIP-1α, RANTES and MIP-1β as shown using purified antibody in FIG. 1 and as originally assayed by ELISA (see Table 2a) and blocked the binding of the viral vCCI molecule to RANTES (FIG. 2). In chemotaxis assays 3C12F inhibited the function of MIP-1α and RANTES, with $IC_{50}$ values of 3-5 μg/mL when using 5 ng/mL chemokine to induce chemotaxis (FIG. 3). By BIAcore®, the affinity of 3C12F for MIP-1α is 49 nM.

Figure 4:
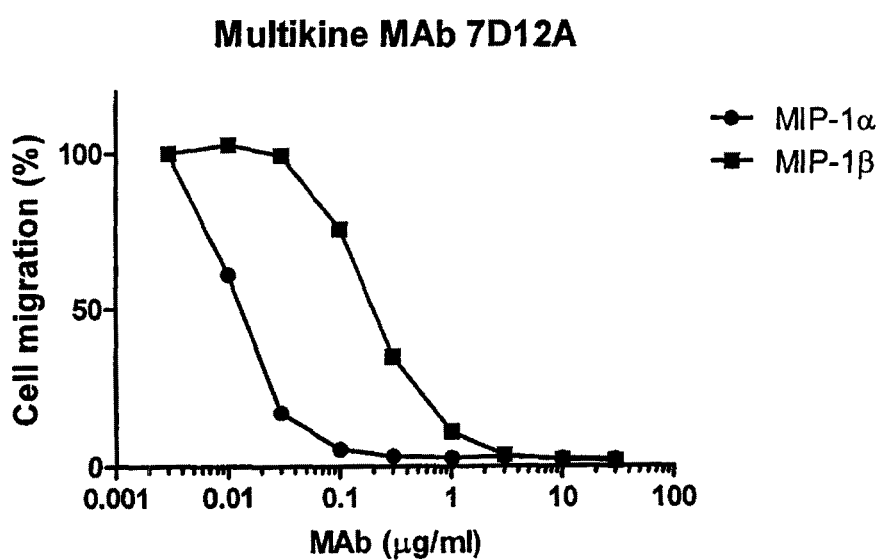
FIG. 4 shows titration of inhibitory activity of purified 7D12A in chemotaxis assays.
Figure 5:
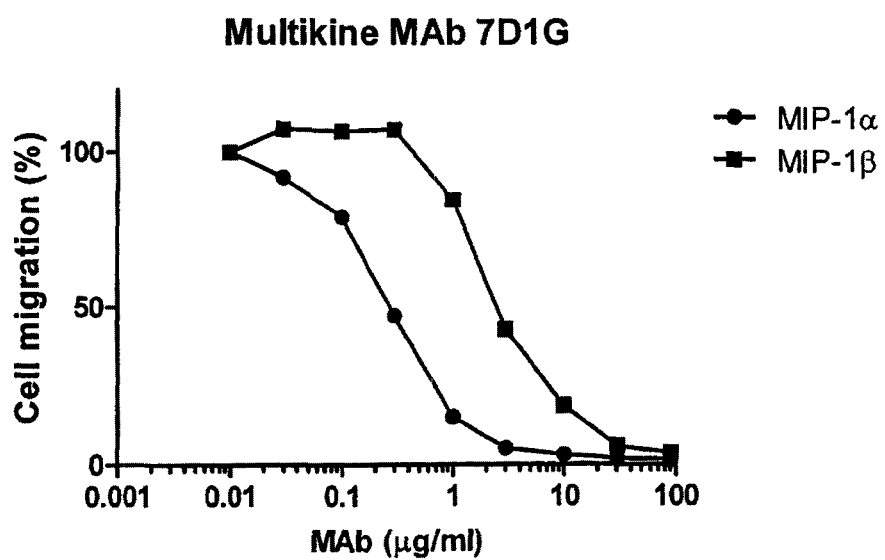
FIG. 5 shows titration of inhibitory activity of purified 7D1G in chemotaxis assays.

Antibodies 7D1G and 7D12A both recognized MIP-1α and MIP-1β when the hybridoma supernatants were assayed by ELISA (Table 2a). These same antibodies also blocked the functions of both chemokines in chemotaxis assays as shown by FIG. 4 and FIG. 5.

Figure 6:
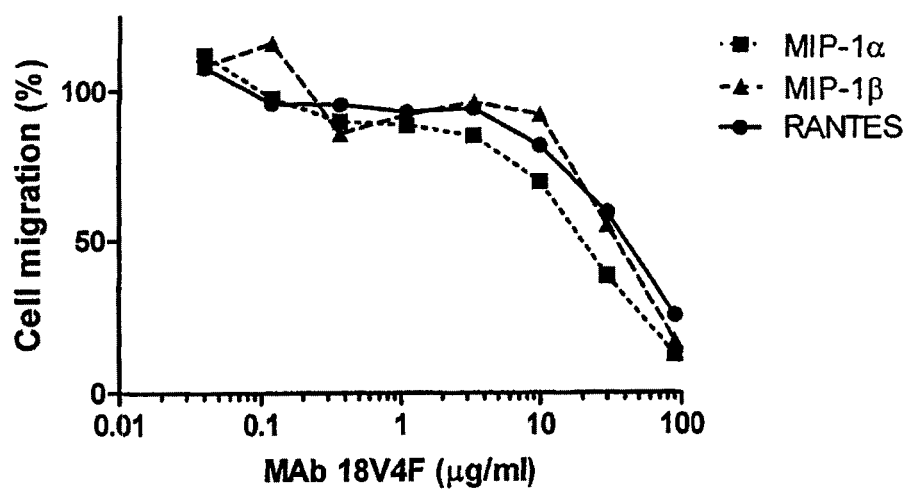
FIG. 6 shows titration of inhibitory activity of purified 18V4F in chemotaxis assays.
Figure 7:
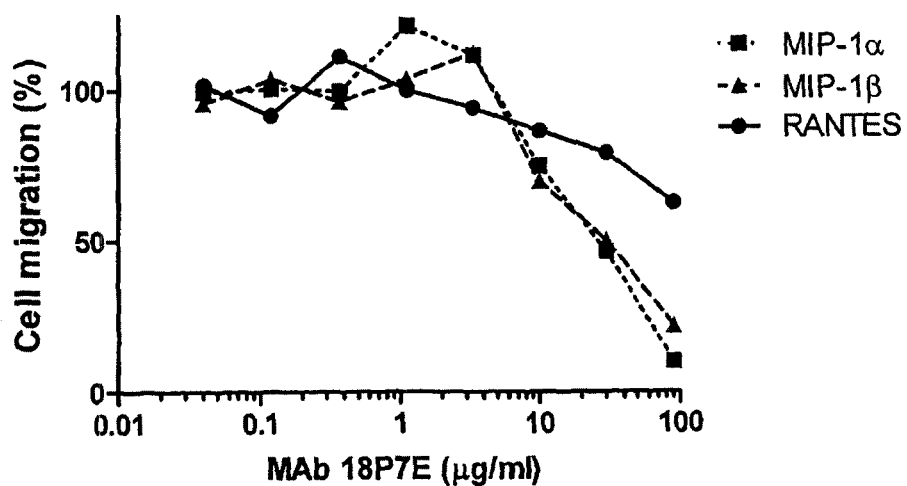
FIG. 7 shows titration of inhibitory activity of purified 18P7E in chemotaxis assays.

Antibodies 18V4F and 18P7E both recognized MIP-1α, MIP-1β, and RANTES when the hybridoma supernatants were assayed by ELISA (Table 2b). The same antibodies also blocked the functions (at least partially) of chemokines MIP-1α, RANTES, and MIP-1β in chemotaxis assays as shown by FIG. 6 and FIG. 7.

Figure 8:
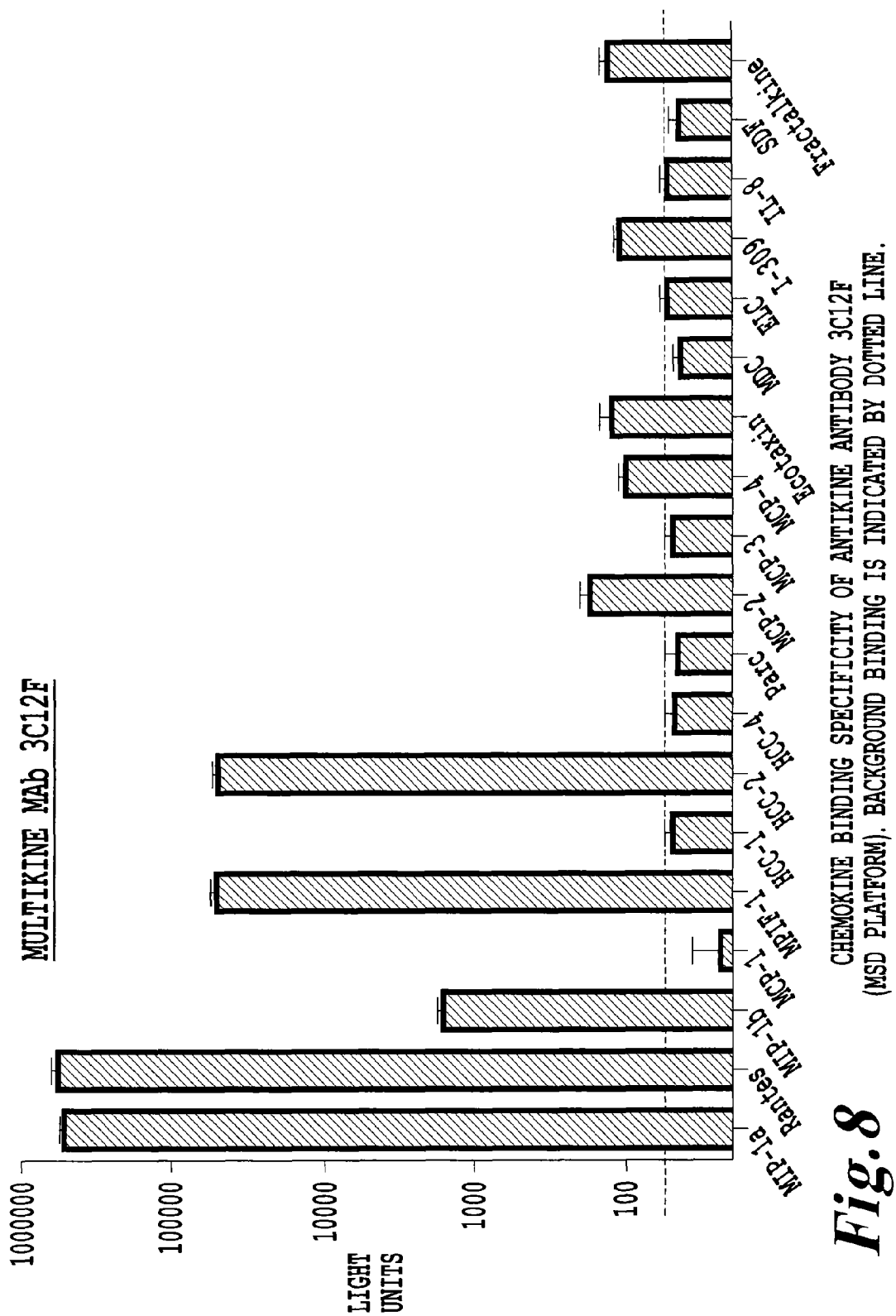
FIG. 8 depicts the chemokine binding specificity of 3C12F using the MSD platform.
Figure 9:
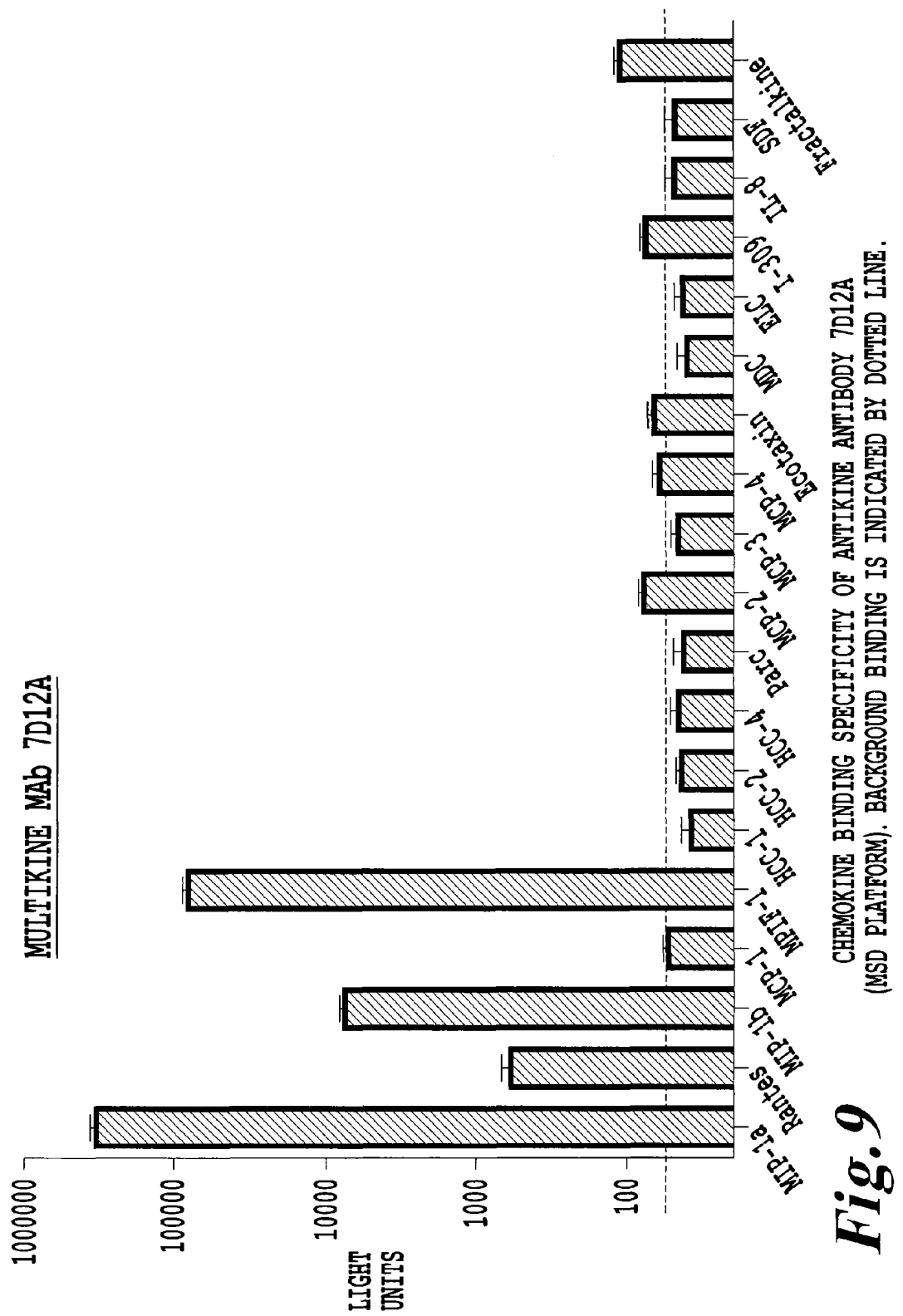
FIG. 9 depicts the chemokine binding specificity of 7D12A using the MSD platform.
Figure 10:
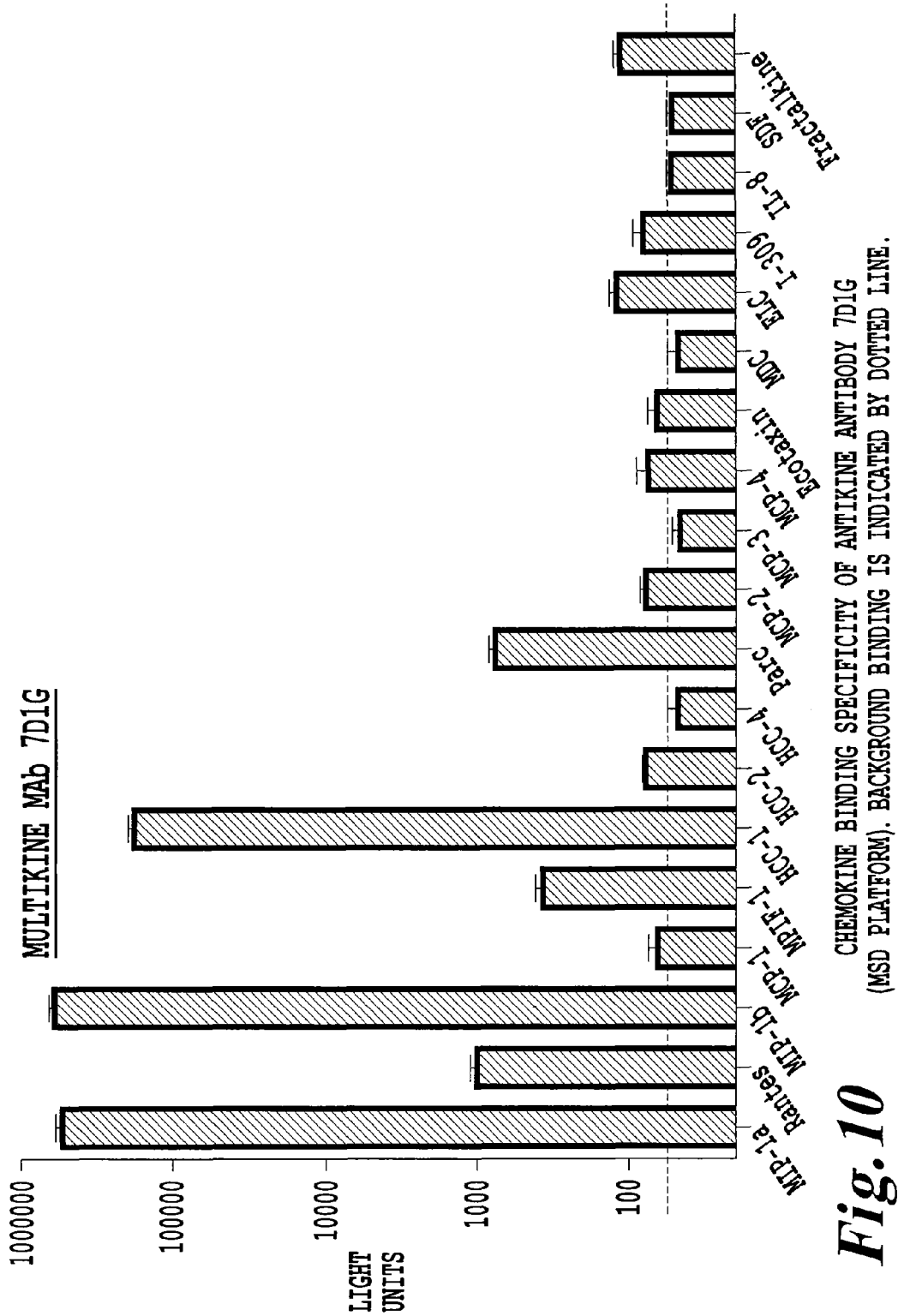
FIG. 10 depicts the chemokine binding specificity of 7D1G using the MSD platform.
Figure 12:
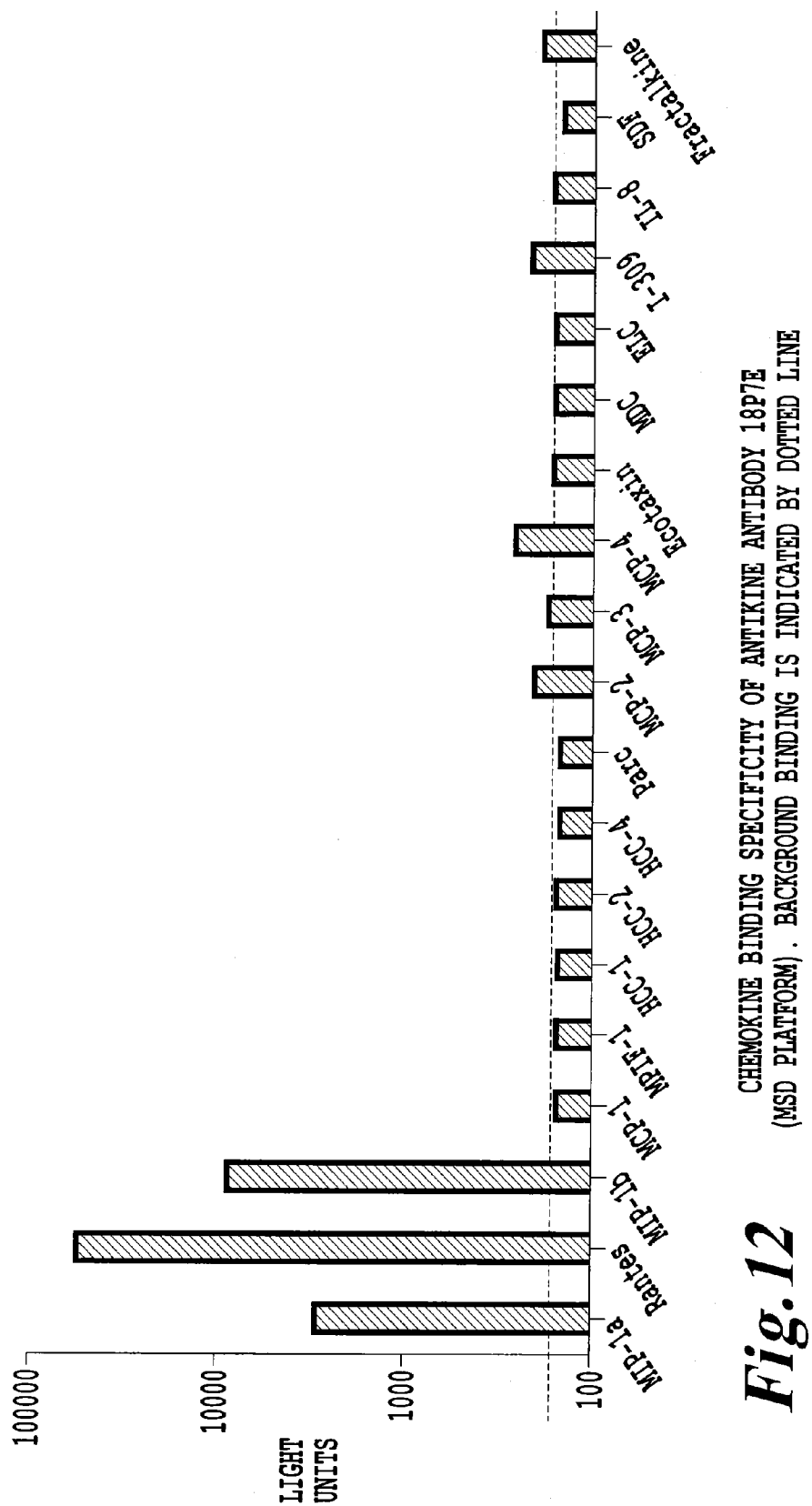
FIG. 12 depicts the chemokine binding specificity of 18P7E using the MSD platform.

Using the MSD platform to analyze the reactivity of purified antikine antibodies (or antibody supernatants from clonal hybridomas, in the case of 18P7E) with an array of chemokines, it was found that the antikine antibody 3C12F bound MIP-1α, RANTES, MIP-1β, MPIF-1 and HCC-2 at least four-fold over background (FIG. 8). Similarly antikine antibody 7D12A bound MIP-1α, RANTES, MIP-1β and MPIF-1 (FIG. 9), and antikine antibody 7D1G bound MIP-1α, RANTES, MIP-1β, HCC-1, MPIF-1 and PARC (FIG. 10). Antikine antibodies 18V4F and 18P7E both bound MIP-1α, RANTES, and MIP-1β (FIG. 11 and FIG. 12).

Table 3 below summarizes the binding specificities of these five antikine monoclonal antibodies.

TABLE 3

Specificities and functional activities of MAbs 3C12F, 7D1G, 7D12A, 18V4F and 18P7E.

|  | 3C12F | 7D1G | 7D12A | 18V4F | 18P7E |
|---|---|---|---|---|---|
| Binding (MSD) | | | | | |
| MIP-1α/CCL3 | Yes | Yes | Yes | Yes | Yes |
| MIP-1β/CCL4 | Yes | Yes | Yes | Yes | Yes |
| RANTES/CCL5 | Yes | Yes | Yes | Yes | Yes |
| MCP-1/CCL2 | No | No | No | No | No |
| Other CC Chemokines | Yes (MPIF-1, HCC-2) | Yes (HCC-1, MPIF-1, PARC) | Yes (MPIF-1) | No | No |
| muMIP-1α | No | Yes | No | No | No |
| muMIP-1β | No | Yes | No | No | No |
| muRANTES | No | No | No | No | No |
| Chemotaxis Inhibition | | | | | |
| MIP-1α/CCL3 | Inhibits | Inhibits | Inhibits | Inhibits | Inhibits |
| MIP-1β/CCL4 | — | Inhibits | Inhibits | Inhibits | Inhibits |
| RANTES/CCL5 | Inhibits | — | — | Inhibits | Inhibits |
| MCP-1/CCL2 | — | — | — | — | — |
| Other CC Chemokines | — | — | — | — | — |
| vCCI binding inhibition to a CC-chemokine | Yes (to RANTES) | ND | ND | ND | ND |

ND = Not determined

Example 6

Analysis of Structures Common to CC Chemokines Bound by Antikine Antibodies

The amino acid sequences of the CC-chemokines bound by monoclonal antibodies 7D1G, 7D12A, 3C12F, 18V4F and 18P7E were aligned. As shown in FIG. 13, several areas of homology or having a high degree of structural similarity were identified to which the antikine monoclonal antibodies of the invention bind. The identification of these common or conserved segments of CC chemokines characterizes antibody binding and serves as core structures for production or screening of new antikine antibodies.

FIGS. 13 a-d show the alignments of the CC chemokines bound by each antikine antibody 3C12F (FIG. 13a), 7D12A (FIG. 13b), 7D1G (FIG. 13c), 18V4F (FIGS. 13d) and 18P7E (FIG. 13d). Identical amino acid residues shared by the CC chemokines bound by a particular antikine antibody are shaded. Similar amino acid residues were designated according to Table 5, for example, the amino acid residue alanine (A) is similar to glycine, serine or threonine.

The shared identical or similar residues were further characterized as not solvent exposed, partially solvent exposed or fully solvent exposed based on FIGS. 1 and 2 of Fernandez, id. and Czaplewski et al., J. Biol. Chem. 274:16077-84 (1999), both of which are incorporated by reference.

Further analysis correlated the shared, solvent exposed residues of the aligned identical or identical+similar residues with CC chemokine residues associated with binding of the CC chemokine receptor. The structural information regarding chemokine receptor binding sites and other structural, chemical, or functional information is incorporated by reference to the entries for the chemokines or other biological molecules described herein to the NCBI Conserved Domain Database CDD 29111 [uid] and to the web addresses shown below each last accessed Aug. 9, 2010.

Putative receptor binding site residues and other structural features for MIP-1α/CCL3 (SEQ ID NO: 71) are described at http://www.ncbi.nlm.nih.gov/Structure/cdd/wrpsb.cgi?INPUT_TYPE=live&SEQUENCE=NP_002974.1.

Putative receptor binding site residues and other structural features for MIP-1β/CCL4 (SEQ ID NO: 72) are described at http://www.ncbi.nlm.nih.gov/Structure/cdd/wrpsb.cgi?INPUT_TYPE=live&SEQUENCE=AAH 70310.1.

Putative receptor binding site residues and other structural features for RANTES/CCL5 (SEQ ID NO:73) are described at http://www.ncbi.nlm.nih.gov/Structure/cdd/wrpsb.cgi?INPUT_TYPE=live&SEQUENCE=P13501.3.

Putative receptor binding site residues and other structural features for MPIF-1/CCL23 (SEQ ID NO:81) are described at http://www.ncbi.nlm.nih.gov/Structure/cdd/wrpsb.cgi?INPUT_TYPE=live&SEQUENCE=P55773.2.

Putative receptor binding site residues and other structural features for HCC-1/CCL14 (SEQ ID NO: 78) are described at http://www.ncbi.nlm.nih.gov/Structure/cdd/wrpsb.cgi?INPUT_TYPE=live&SEQUENCE=NP_004157.1.

Putative receptor binding site residues and other structural features for HCC-2/CCL15 (SEQ ID NO: 79) are described at http://www.ncbi.nlm.nih.gov/Structure/cdd/wrpsb.cgi?INPUT_TYPE=live&SEQUENCE=Q16663.2.

Putative receptor binding site residues and other structural features for PARC/CCL18 (SEQ ID NO:82) are described at http://www.nebi.nlm nih.gov/Structure/cdd/wrpsb.cgi?INPUT_TYPE=live&SEQUENCE=P55774.1.

MAb 3C12F recognizes CC chemokines that share identical amino acid residues C, C, Y, P, Y, T, C, S, P, V, F, T, C, A, P, V and L at relative positions 11, 12, 15, 21, 28, 31, 35, 36, 38, 40, 42, 44, 51, 52, 54, 59 and 66 in FIG. 13a. Of these residues, residues 11, 12, 15, 21, 28, 31, 35, 36, 38, 54 and 66 are partially or fully solvent exposed based on FIGS. 1 and 2 of Fernandez, id and Czaplewski, id.

In addition, the CC chemokines recognized by MAb 3C12F share chemically similar amino acid residues at positions 9, 14, 20, 25, 29, 33, 39, 41, 45, 46, 48 and 63 in FIG. 13a. Of these residues, those at 14, 20, 29, 33, 39, 45, 46, and 48 are partially of fully exposed to solvent (compare FIG. 13a and FIGS. 1 and 2 of Fernandez, et al.).

Based on this structural analysis, identical and similar residues 11, 12, 14, 15, 20, 21, 28, 29, 31, 33, 35, 36, 38, 39, 45, 46, 48, 54 and 66 form shared portions of the CC chemokine molecules bound by MAb 3C12F available as determinants for binding between this antibody and the CC chemokines it recognizes.

Of these shared, solvent-exposed residues, residues 14, 15, 20, 21 and 66 have been characterized as chemokine receptor contact residues according to NCBI Conserved Domain Database CDD 29111. Blocking or binding of an antikine antibody to contact residues for a CC chemokine receptor would affect or modulate the ability of a CC chemokine to bind to its receptors.

The shared, solvent-accessible residues of CC chemokines bound by MAb 3C12F have been further correlated with CC chemokine structure and appear in the N-loop between the initial CC residues of the CC chemokines and the β1 strand, as well as in the 30's loop of the CC chemokines between the β1 and β2 strands.

MAb 7D12A recognizes CC chemokines with amino acid residues C, C, Y, R, P, Y, T, C, S, P, V, F, T, C, A, P, V and L at relative positions 11, 12, 15, 18, 21, 28, 31, 35, 36, 38, 40, 42, 44, 51, 52, 54, 59 and 66 in FIG. 13b. Of these residues, residues 11, 12, 15, 18, 21, 28, 31, 35, 36, 38, 54 and 66 are partially or fully solvent exposed based on FIGS. 1 and 2 of Fernandez, id and Czaplewski, id.

In addition, the CC chemokines recognized by MAb 7D12A share similar amino acid residues at positions 9, 14, 20, 25, 29, 33, 39, 41, 45, 46, 48 and 63 in FIG. 13b. Of these residues, those at 14, 20, 29, 33, 39, 45, 46 and 48 are partially or fully exposed to solvent (compare FIG. 13b and FIGS. 1 and 2 of Fernandez, et al.).

Based on this structural analysis, identical and similar residues 14, 15, 18, 20, 21, 28, 29, 31, 33, 35, 36, 38, 39, 45, 46, 48, 54 and 66 form shared portions of the CC chemokine molecules bound by MAb 7D12A available as determinants for binding between this antibody and the CC chemokines it recognizes.

Of these residues, residues 14, 15, 18, 20, 21 and 66 have been characterized as chemokine receptor contact residues according to NCBI Conserved Domain Database CDD 29111. Competitive antibody binding encompassing these residues would affect the ability of a CC chemokine to bind to its receptors. For CC chemokines recognized by MAb 7D12A several shared solvent accessible residues appear in the N-loop between the initial CC residues of the CC chemokines and the β1 strand, in the 30's loop of the CC chemokines between the β1 and β2 strands, as well as in the 40's loop between the β2 and β3 strands.

MAb 7D1G recognizes CC chemokines with identical amino acid residues C, C, Y, P, Y, T, C, P, T, C, P, and V at relative positions 11, 12, 15, 21, 28, 31, 35, 38, 44, 51, 54 and 59 in FIG. 13c. Of these residues, residues 11, 12, 15, 21, 28, 31, 35, 38 and 54 are partially or fully solvent exposed based on FIGS. 1 and 2 of Fernandez, id and Czaplewski, id.

In addition, the CC chemokines recognized by MAb 7D1G share similar amino acid residues at positions 20, 25, 39-41, 45, 46, 63 and 66 in FIG. 13c. Of these residues, those at 20, 39, 45, 46 and 66 are partially or fully exposed to solvent (compare FIG. 13c and FIGS. 1 and 2 of Fernandez, et al.).

Based on this structural analysis, identical and similar residues 11, 12, 15, 20, 21, 28, 31, 35, 38, 39, 45, 46, 54, and 66 form shared portions of the CC chemokine molecules bound by MAb 7D1G available as determinants for binding between this antibody and the CC chemokines it recognizes.

Of these shared residues, residues 15, 20, 21, 24 and 66 have been characterized as chemokine receptor contact residues according to NCBI Conserved Domain Database CDD 29111. Competitive antibody binding encompassing these residues would affect the ability of a CC chemokine to bind to its receptors. For CC chemokines recognized by MAb 7D1G several shared solvent accessible residues appear in the N-loop between the initial CC residues of the CC chemokines and the β1 strand, as well as in the 40's loop between the β2 and β3 strands.

MAb 18V4F and MAb 18P7E recognize CC chemokines with amino acid residues C, C, Y, R, P, Y, T, C, S, P, V, F, T, C, A, P, V and L at relative positions 11, 12, 15, 18, 21, 28, 31, 35, 36, 38, 40, 42, 44, 51, 52, 54, 59 and 66 in FIG. 13d. Of these residues, residues 11, 12, 15, 18, 21, 28, 31, 35, 36, 38, 54 and 66 are partially or fully solvent exposed based on FIGS. 1 and 2 of Fernandez, id and Czaplewski, id.

In addition, the CC chemokines recognized by MAb 18V4F and 18P7E share similar amino acid residues at positions 9, 14, 20, 25, 29, 33, 39, 41, 45, 46, 48 and 63 in FIG. 13d. Of these residues, those at 14, 20, 29, 33, 39, 45, 46 and 48 are partially or fully exposed to solvent (compare FIG. 13d and FIGS. 1 and 2 of Fernandez, et al.).

Based on this structural analysis, identical and similar residues 14, 15, 18, 20, 21, 28, 29, 31, 33, 35, 36, 38, 39, 45, 46, 48, 54 and 66 form shared portions of the CC chemokine molecules bound by MAb 18V4F and 18P7E available as determinants for binding between these antibodies and the CC chemokines they recognize.

Of these residues, residues 14, 15, 18, 20, 21 and 66 have been characterized as chemokine receptor contact residues according to NCBI Conserved Domain Database CDD 29111. Competitive antibody binding encompassing these residues would affect the ability of a CC chemokine to bind to its receptors. For CC chemokines recognized by MAb 18V4F and 18P7E several shared solvent accessible residues appear in the N-loop between the initial CC residues of the CC chemokines and the β1 strand, in the 30's loop of the CC chemokines between the β1 and β2 strands, as well as in the 40's loop between the β2 and β3 strands.

Example 7

Polynucleotide Sequences of Antikine Antibodies

The sequences of the variable domains of the antibodies were determined after PCR amplification of these regions using primers within the constant regions. RNA was extracted from $10^7$ hybridoma cells using RNeasy (Qiagen), then reverse transcribed using the SuperScript III Reverse Transcription kit from Invitrogen. The CDR regions were amplified by PCR using a set of primers for either the light chain or the heavy chain (Jones & Bendig, Biotechnology 9, 88-89, 1991). The resulting fragments were inserted into the pCR11 plasmid using the Zero Blunt TOPO PCR cloning kit from Invitrogen and sequenced using M13 and M13rev primers. Polynucleotide sequences encoding light and heavy chain segments, such as CDRs, of monoclonal antibodies 3C12F, 7D1G, 7D12A, 18V4F and 18P7E are described below. The DNA coding sequence of the 3C12F heavy chain variable region is set forth as SEQ ID NO: 1 and the amino acid sequence of the 3C12F heavy chain variable region is set forth as SEQ ID NO: 2. The DNA coding sequence of the 3C12F light chain variable region is set forth as SEQ ID NO: 6 and the amino acid sequence of the light chain variable region of 3C12F is set forth as SEQ ID NO: 7. Furthermore, the CDRs of antibody 3C12F are described as SEQ ID NOs: 3-5 (heavy chain variable region) and SEQ ID NOs: 8-10 (light chain variable region).

The DNA coding sequence of the 7D12A heavy chain variable region is set forth as SEQ ID NO: 11 and the amino acid sequence of the 7D12A heavy chain variable region is set forth as SEQ ID NO: 12. The DNA coding sequence of the 7D12A light chain variable region is set forth as SEQ ID NO: 16 and the amino acid sequence of light chain variable region of 7D12A is set forth as SEQ ID NO: 17. Furthermore, the CDRs of antibody 7D12A are described as SEQ ID NOs: 13-15 (heavy chain variable region) and SEQ ID NOs: 18-20 (light chain variable region).

The DNA coding sequence of the 7D1G heavy chain variable region is set forth as SEQ ID NO: 21 and the amino acid sequence of the 7D1G heavy chain variable region is set forth as SEQ ID NO: 22. The DNA coding sequence of the 7D1G light chain variable region is set forth as SEQ ID NO: 26 and the amino acid sequence of light chain variable region of 7D1G is set forth as SEQ ID NO: 27. Furthermore, the CDRs of antibody 7D1G are described as SEQ ID NOs: 23-25 (heavy chain variable region) and SEQ ID NOs: 28-30 (light chain variable region).

The DNA coding sequence of the 18V4F heavy chain variable region is set forth as SEQ ID NO: 31 and the amino acid sequence of the 18V4F heavy chain variable region is set forth as SEQ ID NO: 32. The DNA coding sequence of the 18V4F light chain variable region is set forth as SEQ ID NO: 36 and the amino acid sequence of the light chain variable region of 18V4F is set forth as SEQ ID NO: 37. Furthermore, the CDRs, as defined by Chothia and Lesk, of antibody 18V4F are described as SEQ ID NOs: 33-35 (heavy chain variable region) and SEQ ID NOs: 38-40 (light chain variable region).

The DNA coding sequence of the 18P7E heavy chain variable region is set forth as SEQ ID NO: 41 and the amino acid sequence of the 18P7E heavy chain variable region is set forth as SEQ ID NO: 42. The DNA coding sequence of the 18P7E light chain variable region is set forth as SEQ ID NO: 46 and the amino acid sequence of the light chain variable region of 18P7E is set forth as SEQ ID NO: 47. Furthermore, the CDRs, as defined by Chothia and Lesk, of antibody 18P7E are described as SEQ ID NOs: 43-45 (heavy chain variable region) and SEQ ID NOs: 48-50 (light chain variable region).

Example 8

Humanization of Monoclonal Antibody 3C12F

Antibody humanization methods are designed to produce a molecule with reduced human immunogenicity. Methods of antibody humanization are well known to those of ordinary skill in the art and include those described by Almagro and Frannson, Frontiers Bioscience 13:1619-1633 (2008). The CDR grafting method (Jones et al., Nature 321:522-525, 1986; Riechmann, et al., Nature 332:323-327, 1988) was used to embed the CDR sequences of 3C12F into heavy and light chain IgG variable region framework sequences from similar human germline genes. In this case, the rodent CDR sequences have been embedded into heavy and light chain IgG variable region framework sequences from chosen human germline genes that have the highest identity to the respective rodent heavy and light chain variable sequences. See Jones et al., Nature 321:522-525 (1986); Riechmann, et al., Nature 332:323-327 (1988), which are incorporated herein in their entirety, for suitable methods.

In humanizing 3C12F, the human germline sequences for the variable heavy and light chains that shared the greatest similarity with murine 3C12F sequence were used as the human framework sequences. In addition to sharing high sequence similarity with the murine antibody, the chosen germline sequences were also found to be abundant in a sampling of rearranged antibody sequences. The murine residues that reside in the complementary determining regions (CDRs) as defined by Kabat were grafted into the human framework sequences with additional residues being reverted to the murine amino acid when evidence indicated that they may be essential for binding. The polynucleotide sequences encoding the heavy and light chains of the humanized 3C12F MAb are given by SEQ ID NOS: 51 and 56. The corresponding amino acid sequences and CDRs are identified by SEQ ID NOS: 52-55 and 57-60.

Example 9

Humanization of Monoclonal Antibody 18V4F

In humanizing 18V4F, a different strategy was employed than that used in humanizing 3C12F. Instead of grafting the CDRs of the murine 18V4F antibody into the most similar human germline sequence, the CDRs were grafted into a consensus sequence compiled from the most populated variable heavy chain family, VHIII, and the most populated variable lambda light chain family, VLλIII. Next, only those residues in the CDR that have been defined by Chothia and Lesk to be structurally relevant for binding were initially grafted into the consensus frameworks. Additional CDR positions defined more broadly by Kabat, as well as framework residues, were reverted back the murine amino acid when evidence indicated they may be important to retain binding. The polynucleotide sequences encoding the heavy and light chains of the humanized 18V4F MAb are given by SEQ ID NOS: 61 and 66. The corresponding amino acid sequences and CDRs are identified by SEQ ID NOS: 62-65 and 67-70.

Example 10

Affinity Maturation of Humanized MAb 3C12F and Mab 18V4F

The binding affinities of the antikine monoclonal antibodies of the invention may be further enhanced, if desired, by affinity maturation as described for example by Wu et al. (1998), Proc. Natl. Acad. Sci. USA 95: 6037-6042, which is hereby incorporated by reference.

To improve the binding characteristics of humanized MAb 3C12F and humanized MAb 18V4F to various chemokines (e.g., RANTES/CCL5, MIP-1α/CCL3 and MIP-1β/CCL4) and to generate more potent agents, a site-directed mutagenesis strategy in conjunction with phage display was employed. The Fab fragment of humanized 3C12F or humanized 18V4F was first displayed on the surface of filamentous phage M13 as a heavy chain fusion with the M13 gene III protein with co-expression of the humanized 3C12F or humanized 18V4F light chain, respectively. Next, every position of all six CDRs of humanized Mab 3C12F or humanized 18V4F was methodically mutated, 4-6 contiguous CDR residues at a time, using the protocol of Sidhu and Weiss (Phage Display, A Practical Approach, Clackson, T. and Lowman, H. B., ed., Oxford University Press, 2004, Chapter 4). In some cases, the amino acids surrounding the defined CDRs were also mutated in case they were involved in antigen binding. A total of 15 libraries were constructed for each antibody.

Phage displaying mutant humanized 3C12F or humanized 18V4F Fab fragments were prepared for each library for binding selections. Up to six rounds of phage selection for higher affinity variants of humanized 3C12F or humanized 18V4F were conducted using the affinity maturation protocols of Nielsen and Marks (Clackson and Lowman, ibid, Chapter 14). Briefly, binding selections are undertaken using biotinylated chemokines and captured using streptavidin-coated magnetic beads to identify higher variants of humanized 3C12F Fab or humanized 18V4F Fab. Higher affinity variants are first identified using methods well known in the art (see Clackson and Lowman and references cited therein) and then combined to achieve greater affinity improvements.

The affinity of antibodies for their targets also can be increased using other various methods known in the art. Affinity can be increased by direct mutation, phage display, or chain shuffling within the nucleic acids encoding the antibody molecules. Individual or multiple residues can be randomized so that in a population of otherwise identical antigen antibody sites, all twenty amino acids or a subset of these are found at particular positions within or adjacent to the CDRs. Useful methods for this purpose are incorporated by reference to Yang et al., J. Mol. Biol. 254, 392-403 (1995); Hawkins et al., J. Mol. Biol. 226, 889-896 (1992); or Low et al., J. Mol. Biol. 250, 359-368 (1996). Marks et al., Bio/Technology, 10:779-783 (1992) describes affinity maturation by VH and VL domain shuffling; random mutagenesis of CDR and/or framework residues is described by Barbas et al., Proc. Nat. Acad. Sci., USA 91:3809-3813 (1994); Schier et al., Gene, 169:147-155, 1995, Yelton et al., J. Immunol., 155:1994-2004 (1995); Jackson et al., J. Immunol. 154(7):3310-3319 (1995); and Hawkins et al., J. Mol. Biol., 226:889-896 (1992) each of which is also incorporated by reference.

Affinity maturation is sometimes carried out using random mutagenesis. Amino acid substitutions made at particular positions can be random, or made using simplistic rules. For example, all residues could be mutated to alanine, which is referred to as alanine scanning, see e.g., WO 9523813. Sequence-based methods of affinity maturation may also be used to increase the binding affinities of antibodies, see U.S. 2003/022240 A1 and U.S. 2002/177170 A1 both of which are incorporated by reference. Other methods include oligonucleotide-based mutagenesis of amino acids within some or all positions with some or all CDRs, followed by screening for higher affinity, as described by Wu et al., Proc. Natl. Acad. Sci. U.S.A., 95, 6037-6042 (1998) or by selection for higher affinity using phage display, as described by Rajpal, et al., Proc. Natl. Acad. Sci. U.S.A., 102:8466-8471 (1996). Selection of affinity matured antibodies can also be done by displaying the antibody or a fragment thereof on the surface yeast cells, as described by Siegal, Methods Mol. Biol., 504: 351-83 (2009), or on the surface of mammalian cells, as described by Ho, et al., Proc. Natl. Acad. Sci. U.S.A., 103: 9637-9642 (2006). The methods described in the documents above which may be used in the process of affinity maturation are each incorporated by reference to the documents cited in this Example.

Identification of CC Chemokine and Cowpox Virus Sequences

The identities of the chemokines and other products disclosed herein are incorporated by reference to the accession numbers in Table 4.

TABLE 4

Accession Numbers for CC Chemokines and Other Molecules

| Chemokine | SEQ ID | Catalog # | NCBI Accession # | Amino Acid Sequence |
|---|---|---|---|---|
| HUMAN | | | | |
| MIP-1α/ CCL3 | 71 | Pepro Tech 300-08 | P10147.1; NP_002974.1 | ASLAADTPTACCFSYTSRQIPQNFI ADYFETSSQCSKPGVIFLTKRSRQV CADPSEEWVQKYVSDLELSA |
| MIP-1β/ CCL4 | 72 | Pepro Tech 300-09 | GenBank AAH70310.1 | APMGSDPPTACCFSYTARKLPHNFVV DYYETSSLCSQPAVVFQTKRGKQVCA DPSESWVQEYVYDLELN |
| RANTES/ CCL5 | 73 | Pepro Tech 300-06 | P13501.3 | SPYSSDTTPCCFAYIARPLPRAHIKEYF YTSGKCSNPAVVFVTRKNRQVCANPE KKWVREYINSLEMS |
| MCP-1/ CCL2 | 74 | Pepro Tech 300-04 | P13500.1 | QPDAINAPVTCCYNFTNRKISVQRLAS YRRITSSKCPKEAVIFKTIVAKEICADP KQKWVQDSMDHLDKQTQTPKT |
| MCP-2/ CCL8 | 75 | R & D Systems 281-CP | P80075.2 | QPDSVSIPITCCFNVINRKIPIQRLESYT RITNIQCPKEAVIFKTKRGKEVCADPK ERWVRDSMKHLDQIFQNLKP |
| MCP-3/ CCL7 | 76 | R & D Systems 282-P3 | P80098.3 | QPVGINTSTTCCYRFINKKIPKQRLESY RRTTSSHCPREAVIFKTKLDKEICADP TQKWVQDFMKHLDKKTQTPKL |
| MCP-4/ CCL13 | 77 | R & D Systems 327-P4 | Q99616.1 | QPDALNVPSTCCFTFSSKKISLQRLKS YVITTSRCPQKAVIFRTKLGKEICADP KEKWVQNYMKHLGRKAHTLKT |
| HCC-1/ CCL14/ CCL14a | 78 | R & D Systems 1578-HC | NP_004157.1 | GPYHPSECCFTYTTYKIPRQRIMDYYE TNSQCSKPGIVFITKRGHSVCTNPSDK WVQDYIKDMKEN |
| HCC-2/ MIP-1δ/ CCL15 | 79 | R & D Systems 628-LK | Q16663.2 | SFHFAADCCTSYISQSIPCSLMKSYFET SSECSKPGVIFLTKKGRQVCAKPSGPG VQDCMKKLKPYSI |
| HCC-4/ CCL16 | 80 | R & D Systems 802-HC | O15467.1 | QPKVPEWVNTPSTCCLKYYEKVLPR RLVVGYRKALNCHLPAIIFVTKRNR EVCTNPNDDWVQEYIKDPNLPLLPT RNLSTVKIITAKNGQPQLLNSQ |
| MPIF-1/ CCL23 | 81 | R & D Systems 131-M1 | P55773.2 | RFHATSADCCISYTPRSIPCSLLESYF ETNSECSKPGVIFLTKKGRRFCANPS DKQVQVCMRMLKLDTRIKTRKN |
| PARC/ CCL18 | 82 | R & D Systems 394-PA | P55774.1 | AQVGTNKELCCLVYTSWQIPQKFIV DYSETSPQCPKPGVILLTKRGRQICA DPNKKWVQKYISDLKLNA |
| Eotaxin/ CCL11 | 83 | R & D Systems 320-EO | P51671.1; Q6I9T4 | GPASVPTTCCFNLANRKIPLQRLESY RRITSGKCPQKAVIFKTKLAKDICAD PKKKWVQDSMKYLDQKSPTPKP |
| Eotaxin-2/ CCL24 | 84 | R & D Systems 343-E2 | GenBank AAB51135.1 | VVIPSPCCMFFVSKRIPENRVVSYQL SSRSTCLKGGVIFTTKKGQQFCGDP KQEWVQRYMKNLDAKQKKASPRA RAVAVKGPVQRYPGNQTTC |
| Eotaxin3/ CCL26 | 85 | R & D Systems 346-E3 | Q9Y258.1 | TRGSDISKTCCFQYSHKPLPWTWV RSYEFTSNSCSQRAVIFTTKRGKKV CTHPRKKWVQKYISLLKTPKQL |
| MDC/ CCL22 | 86 | R & D Systems 336-MD | O00626.1 | GPYGANMEDSVCCRDYVRYRLPL RVVKHFYWTSDSCPRPGVVLLTFR DKEICADPRVPWVKMILNKLSQ |
| TARC/ CCL17 | 87 | R & D Systems 364-DN | Q92583.1 | ARGTNVGRECCLEYFKGAIPLRKL KTWYQTSEDCSRDAIVFVTVQGR AICSDPNNKRVKNAVKYLQSLERS |
| LARC/ MIP-3α/ CCL20 | 88 | R & D Systems 360-MP | P78556.1 | ASNFDCCLGYTDRILHPKFIVGFTR QLANEGCDINAIIFHTKKKLSVCAN PKQTWVKYIVRLLSKKVKNM |

TABLE 4 -continued

Accession Numbers for CC Chemokines and Other Molecules

| Chemokine | SEQ ID | Catalog # | NCBI Accession # | Amino Acid Sequence |
|---|---|---|---|---|
| ELC/ MIP-3β/ CCL19 | 89 | R & D Systems 361-MI | Q99731.1 | GTNDAEDCCLSVTQKPIPGYIVRNF HYLLIKDGCRVPAVVFTTLRGRQL CAPPDQPWVERIIQRLQRTSAKMK RRSS |
| SLC/6Ckine/ CCL21 | 90 | R & D Systems 366-6C | O00585.1; Q6ICR7 | SDGGAQDCCLKYSQRKIPAKVVRS YRKQEPSLGCSIPAILFLPRKRSQAE LCADPKELWVQQLMQHLDKTPSPQ KPAQGCRKDRGASKTGKKGKGSK GCKRTERSQTPKGP |
| I-309/ CCL1 | 91 | R & D Systems 272-I | P22362.1 | KSMQVPFSRCCFSFAEQEIPLRAILC YRNTSSICSNEGLIFKLKRGKEACAL DTVGWVQRHRKMLRHCPSKRK |
| TECK/ CCL25 | 92 | R & D Systems 334-TK | GenBank AAB69981.1 | QGVFEDCCLAYHYPIGWAVLRRAW TYRIQEVSGSCNLPAAIFYLPKRHRK VCGNPKSREVQRAMKLLDARNKVF AKLHHNMQTFQAGPHAVKKLSSGN SKLSSSKFSNPISSSKRNVSLLISANS GL |
| CTACK/ CCL27 | 93 | R & D Systems 376-CT | Q9Y4X3.1 | FLLPPSTACCTQLYRKPLSDKLLRKV IQVELQEADGDCHLQAFVLHLAQRS ICIHPQNPSLSQWFEHQERKLHGTLP KLNFGMLRKMG |
| CCL28 | 94 | R & D Systems 717-VC | Q9NRJ3.1 | ILPIASSCCTEVSHHISRRLLERVNMC RIQRADGDCDLAAVILHVKRRRICVS PHNHTVKQWMKVQAAKKNGKGNV CHRKKHHGKRNSNRAHQGKHETYG HKTPY |
| XCL1 | 95 | R & D Systems 695-LT | P47992.1 | MVGSEVSDKRTCVSLTTQRLPVSRI KTYTITEGSLRAVIFITKRGLKVCAD PQATWVRDVVRSMDRKSNTRNNM IQTKPTGTQQSTNTAVTLTG |
| Fractalkine/ CX3CL1 | 96 | R & D Systems 365-FR | GenBank AAB49679.1 | MAPISLSWLLRLATFCHLTVLLAGQ HHGVTKCNITCSKMTSKIPVALLIH YQQNQASCGKRAIILETRQHRLFCA DPKEQWVKDAMQHLDRQAAALTR NGGTFEKQIGEVKPRTTPAAGGMD ESVVLEPEATGESSSLEPTPSSQEAQ RALGTSPELPTGVTGSSGTRLPPTPK AQDGGPVGTELFRVPPVSTAATWQ SSAPHQPGPSLWAEAKTSEAPSTQD PSTQASTASSPAPEENAPSEGQRVW GQGQSPRPENSLEREEMGPVPAHTD AFQDWGPGSMAHVSVVPVSSEGTP SREPVASGSWTPKAEEPIHATMDPQ RLGVLITPVPDAQAATR |
| IL-8/ CXCL8 | 97 | R & D Systems 208-IL | P10145.1 | SAKELRCQCIKTYSKPFHPKFIKELR VIESGPHCANTEIIVKLSDGRELCLD PKENWVQRVVEKFLKRAENS |
| Gro-α/ CXCL1 | 98 | R & D Systems 275-GR | P09341.1 | ASVATELRCQCLQTLQGIHPKNIQS VNVKSPGPHCAQTEVIATLKNGRK ACLNPASPIVKKIIEKMLNSDKSN |
| Gro-β/ CXCL2 | 99 | R & D Systems 276-GB | P19875.1 | APLATELRCQCLQTLQGIHLKNIQS VKVKSPGPHCAQTEVIATLKNGQK ACLNPASPMVKKIIEKMLKNGKSN |
| Gro-γ/ CXCL3 | 100 | R & D Systems 277-GG | P19876.1 | ASVVTELRCQCLQTLQGIHLKNIQS VNVRSPGPHCAQTEVIATLKNGKK ACLNPASPMVQKIIEKILNKGSTN |
| ENA-78/ CXCL5 | 101 | R & D Systems 254-X | P42830.1 | AGPAAAVLRELRCVCLQTTQGVHP KMISNLQVFAIGPQCSKVEVVASLK NGKEICLDPEAPFLKKVIQKILDGG NKEN |

TABLE 4 -continued

Accession Numbers for CC Chemokines and Other Molecules

| Chemokine | SEQ ID | Catalog # | NCBI Accession # | Amino Acid Sequence |
|---|---|---|---|---|
| GCP-2/ CXCL6 | 102 | R & D Systems 333-GC | P80162.4 | VSAVLTELRCTCLRVTLRVNPKTIG KLQVFPAGPQCSKVEVVASLKNGK QVCLDPEAPFLKKVIQKILDSGNK KN |
| NAP-2/ CXCL7 | 103 | R & D Systems 393-NP | P02775.3 | AELRCMCIKTTSGIHPKNIQSLEVIG KGTHCNQVEVIATLKDGRKICLDP DAPRIKKIVQKKLAGDESAD |
| PF4/ CXCL4 | 104 | R & D Systems 795-P4 | P02776.2 | EAEEDGDLQCLCVKTTSQVRPRHI TSLEVIKAGPHCPTAQLIATLKNGR KICLDLQAPLYKKIIKKLLES |
| IP-10/ CXCL10 | 105 | R & D Systems 266-IP | P02778.2 | MVPLSRTVRCTCISISNQPVNPRSL EKLEIIPASQFCPRVEIIATMKKKG EKRCLNPESKAIKNLLKAVSKERSK RSP |
| MIG/ CXCL9 | 106 | R & D Systems 392-MG | Q07325.1 | TPVVRKGRCSCISTNQGTIHLQSLK DLKQFAPSPSCEKIEIIATLKNGVQT CLNPDSADVKELIKKTEKQVSQKK KQNGKKHQKKKVLKVRKSQRSR QKKTT |
| I-TAC/ CXCL11 | 107 | R & D Systems 672-IT | O14625.1 | FPMFKRGRCLCIGPGVKAVKVADIE KASIMYPSNNCDKIEVIITLKENKG QRCLNPKSKQARLIIKKVERKNF |
| SDF-1/ CXCL12 | 108 | R & D Systems 350-NS | P48061.1; Q9H554 | KPVSLSYRCPCRFFESHVARANVK HLKILNTPNCALQIVARLKNNNRQ VCIDPKLKWIQEYLEKALNK |
| BCA-1/ BLC/ CXCL13 | 109 | R & D Systems 801-CX | O43927.1; Q53X90 | VLEVYYTSLRCRCVQESSVFIPRRF IDRIQILPRGNGCPRKEIIVWKKNK SIVCVDPQAEWIQRMMEVLRKRS SSTLPVPVFKRKIP |
| CXCL16 | 110 | R & D Systems 976-CX | Q9H2A7.4 | NEGSVTGSCYCGKRISSDSPPSVQ FMNRLRKHLRAYHRCLYYTRFQL LSWSVCGGNKDPWVQELMSCLD LKECGHAYSGIVAHQKHLLP |
| BRAK/ CXCL14 | 111 | R & D Systems 866-CX | O95715.1 | SKCKCSRKGPKIRYSDVKKLEMK PKYPHCEEKMVIITTKSVSRYRGQ EHCLHPKLQSTKRFIKWYNAWN EKRRVYEE |
| MOUSE | | | | |
| MIP-1α/ CCL3 | 112 | R & D Systems 450-MA | P10855.2 | APYGADTPTACCFSYSRKIPRQFI VDYFETSSLCSQPGVIFLTKRNRQ ICADSKETWVQEYITDLELNA |
| MIP-β/ CCL4 | 113 | R & D Systems 451-MA | P14097.3 | APMGSDPPTSCCFSYTSRQLHRSF VMDYYETSSLCSKPAVVFLTKRG RQICANPSEPWVTEYMSDLELN |
| RANTES/ CCL5 | 114 | R & D Systems 478-MR | P30882.2 | SPYGSDTTPCCFAYLSLALPRAHV KEYFYTSSKCSNLAVVFVTRRNR QVCANPEKKWVQEYINYLEMS |
| MCP-1/ CCL2 | 115 | R & D Systems 479-JE | 81870303; Q5SVU3 | QPDAVNAPLTCCYSFTSKMIPM SRLESYKRITSSRCPKEAVVFVT KLKREVCADPKKEWVQTYIKN LDRNQMRSEPTTLFKTASALRS SAPLNVKLTRKSEANASTTFST TTSSTSVGVTSVTVN |
| MCP-5/ CCL12 | 116 | R & D Systems 428-P5 | Q62401.1 | GPDAVSTPVTCCYNVVKQKIH VRKLKSYRRITSSQCPREAVIFR TILDKEICADPKEKWVKNSINH LDKTSQTFILEPSCLG |

TABLE 4 -continued

Accession Numbers for CC Chemokines and Other Molecules

| Chemokine | SEQ ID | Catalog # | NCBI Accession # | Amino Acid Sequence |
|---|---|---|---|---|
| COXPOX VIRUS | | | | |
| vCCI | 117 | N/A | NP_620006.1 | MKQIVLACICLAAVAI

| | | | | | | | | | | | | | | | | |
|---|---|---|---|---|---|---|---|---|---|---|---|---|---|---|---|---|
| tca | gtc | aag | ttg | tcc | tgc | aca | gct | tct | ggc | ttc | aac | att | aaa | gac | acc | 96 |
| Ser | Val | Lys | Leu | Ser | Cys | Thr | Ala | Ser | Gly | Phe | Asn | Ile | Lys | Asp | Thr | |
| | | | 20 | | | | 25 | | | | | 30 | | | | |
| tat | ata | cac | tgg | gtg | aag | cag | agg | cct | gaa | cag | ggc | ctg | gag | tgg | att | 144 |
| Tyr | Ile | His | Trp | Val | Lys | Gln | Arg | Pro | Glu | Gln | Gly | Leu | Glu | Trp | Ile | |
| | | 35 | | | | | 40 | | | | | 45 | | | | |
| gga | agg | att | gat | cct | gcg | aat | ggt | aat | act | caa | tat | gac | ccg | aag | ttc | 192 |
| Gly | Arg | Ile | Asp | Pro | Ala | Asn | Gly | Asn | Thr | Gln | Tyr | Asp | Pro | Lys | Phe | |
| | 50 | | | | | 55 | | | | | 60 | | | | | |
| cag | ggc | aag | gcc | act | ata | aca | gca | gac | aca | tcc | tcc | aac | aca | gcc | tac | 240 |
| Gln | Gly | Lys | Ala | Thr | Ile | Thr | Ala | Asp | Thr | Ser | Ser | Asn | Thr | Ala | Tyr | |
| 65 | | | | | 70 | | | | | 75 | | | | | 80 | |
| ctg | cag | ctc | acc | agc | ctg | aca | tct | gag | gac | act | gcc | gtc | tat | tac | tgt | 288 |
| Leu | Gln | Leu | Thr | Ser | Leu | Thr | Ser | Glu | Asp | Thr | Ala | Val | Tyr | Tyr | Cys | |
| | | | | 85 | | | | | 90 | | | | | 95 | | |
| gct | aga | agg | tgg | gat | tac | gac | tat | gct | atg | gac | tac | tgg | ggt | caa | gga | 336 |
| Ala | Arg | Arg | Trp | Asp | Tyr | Asp | Tyr | Ala | Met | Asp | Tyr | Trp | Gly | Gln | Gly | |
| | | | 100 | | | | | 105 | | | | | 110 | | | |
| acc | tca | gtc | acc | gtc | tcc | tca | | | | | | | | | | 357 |
| Thr | Ser | Val | Thr | Val | Ser | Ser | | | | | | | | | | |
| | | | 115 | | | | | | | | | | | | | |

```
<210> SEQ ID NO 2
<211> LENGTH: 119
<212> TYPE: PRT
<213> ORGANISM: Mus musculus

<400> SEQUENCE: 2
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Gln Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Arg Arg Trp Asp Tyr Asp Tyr Ala Met Asp Tyr Trp Gly Gln Gly
            100                 105                 110

Thr Ser Val Thr Val Ser Ser
        115

```
<210> SEQ ID NO 3
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: VH CDR1 of 3C12F

<400> SEQUENCE: 3
```

Asp Thr Tyr Ile His
1               5

```
<210> SEQ ID NO 4
<211> LENGTH: 17
<212> TYPE: PRT
```

```
<213> ORGANISM: Mus musculus
<220> FEATURE:
<221> NAME/KEY: MISC_FEATURE
<222> LOCATION: (1)..(17)
<223> OTHER INFORMATION: VH CDR2 of 3C12F

<400> SEQUENCE: 4

Arg Ile Asp Pro Ala Asn Gly Asn Thr Gln Tyr Asp Pro Lys Phe Gln
1               5                   10                  15
Gly

<210> SEQ ID NO 5
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: VH CDR3 of 3C12F

<400> SEQUENCE: 5

Arg Trp Asp Tyr Asp Tyr Ala Met Asp Tyr
1               5                   10

<210> SEQ ID NO 6
<211> LENGTH: 321
<212> TYPE: DNA
<213> ORGANISM: Mus musculus
<220> FEATURE:
<221> NAME/KEY: CDS
<222> LOCATION: (1)..(321)
<223> OTHER INFORMATION: Coding sequence for 3C12F VL

<400> SEQUENCE: 6 gac atc cag atg act cag tct cca gcc tcc cta tct gca tct gtg gga      48
Asp Ile Gln Met Thr Gln Ser Pro Ala Ser Leu Ser Ala Ser Val Gly
1               5                   10                  15 gaa act gtc acc atc aca tgt cga gga agt ggg aat att cac aat tat      96
Glu Thr Val Thr Ile Thr Cys Arg Gly Ser Gly Asn Ile His Asn Tyr
            20                  25                  30 tta gca tgg tat cag cag aaa cag gga aaa tct cct cag ctc ctg gtc     144
Leu Ala Trp Tyr Gln Gln Lys Gln Gly Lys Ser Pro Gln Leu Leu Val
        35                  40                  45 tat aat gca aaa acc tta gca gat ggt gtg cca tca agg ttc agt ggc     192
Tyr Asn Ala Lys Thr Leu Ala Asp Gly Val Pro Ser Arg Phe Ser Gly
    50                  55                  60 agt gga tca gga aca caa tat tct ctc aag atc aac agc ctg cag cct     240
Ser Gly Ser Gly Thr Gln Tyr Ser Leu Lys Ile Asn Ser Leu Gln Pro
65                  70                  75                  80 gaa gat ttt ggg agt tat tac tgt caa cat ttt tgg agt act ccg tac     288
Glu Asp Phe Gly Ser Tyr Tyr Cys Gln His Phe Trp Ser Thr Pro Tyr
                85                  90                  95 acg ttc gga ggg ggg acc aag ctg gaa ata aaa                         321
Thr Phe Gly Gly Gly Thr Lys Leu Glu Ile Lys
                100                 105

<210> SEQ ID NO 7
<211> LENGTH: 107
<212> TYPE: PRT
<213> ORGANISM: Mus musculus

<400> SEQUENCE: 7

Asp Ile Gln Met Thr Gln Ser Pro Ala Ser Leu Ser Ala Ser Val Gly
1               5                   10                  15
```

-continued

```
Glu Thr Val Thr Ile Thr Cys Arg Gly Ser Gly Asn Ile His Asn Tyr
             20                  25                  30

Leu Ala Trp Tyr Gln Gln Lys Gln Gly Lys Ser Pro Gln Leu Leu Val
         35                  40                  45

Tyr Asn Ala Lys Thr Leu Ala Asp Gly Val Pro Ser Arg Phe Ser Gly
     50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Tyr
                 85                  90                  95

Thr Phe Gly Gly Gly Thr Lys Leu Glu Ile Lys
            100                 105
```

<210> SEQ ID NO 8
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: VL CDR1 of 3C12F

<400> SEQUENCE: 8

```
Arg Gly Ser Gly Asn Ile His Asn Tyr Leu Ala
1               5                   10
```

<210> SEQ ID NO 9
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: VL CDR2 of 3C12F

<400> SEQUENCE: 9

```
Asn Ala Lys Thr Leu Ala Asp
1               5
```

<210> SEQ ID NO 10
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: VL CDR3 of 3C12F

<400> SEQUENCE: 10

```
Gln His Phe Trp Ser Thr Pro Tyr Thr
1               5
```

<210> SEQ ID NO 11
<211> LENGTH: 354
<212> TYPE: DNA
<213> ORGANISM: Mus musculus
<220> FEATURE:
<221> NAME/KEY: CDS
<222> LOCATION: (1)..(354)
<223> OTHER INFORMATION: Coding sequence for 7D12A VH

<400> SEQUENCE: 11

```
gag gtg cat ctt cag gag tca gga cct agc ctc gtg aaa cct tct cag     48
Glu Val His Leu Gln Glu Ser Gly Pro Ser Leu Val Lys Pro Ser Gln
1               5                   10                  15
```

```
act ctg tcc ctc acc tgt tct gtc act ggc gac tcc atc acc aat ggt        96
Thr Leu Ser Leu Thr Cys Ser Val Thr Gly Asp Ser Ile Thr Asn Gly
         20                  25                  30 tac tgg aac tgg atc cgg aaa ttc cca ggg aat aaa ctt gac tac atg       144
Tyr Trp Asn Trp Ile Arg Lys Phe Pro Gly Asn Lys Leu Asp Tyr Met
         35                  40                  45 gga tac ata agc tac gat ggt aac act tac tac aat cca tct ctc aaa       192
Gly Tyr Ile Ser Tyr Asp Gly Asn Thr Tyr Tyr Asn Pro Ser Leu Lys
 50                  55                  60 agt cga ttc tcc atc act cga gac aca tcc aag aac cag tac tac ctg       240
Ser Arg Phe Ser Ile Thr Arg Asp Thr Ser Lys Asn Gln Tyr Tyr Leu
 65                  70                  75                  80 cag ttg aat tct gtg act act gaa gac aca gcc aca tat tac tgt tca       288
Gln Leu Asn Ser Val Thr Thr Glu Asp Thr Ala Thr Tyr Tyr Cys Ser
             85                  90                  95 aga gga gac tac gga acc tat gtt atg gac tac tgg ggt caa gga acc       336
Arg Gly Asp Tyr Gly Thr Tyr Val Met Asp Tyr Trp Gly Gln Gly Thr
                100                 105                 110 tca gtc acc gtc tcc tca                                                354
Ser Val Thr Val Ser Ser
        115

<210> SEQ ID NO 12
<211> LENGTH: 118
<212> TYPE: PRT
<213> ORGANISM: Mus musculus

<400> SEQUENCE: 12

Glu Val His Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Asn Gly
         20                  25                  30

Tyr Trp Asn Trp Ile Arg Lys Phe Pro Gly Asn Lys Leu Asp Tyr Met
         35                  40                  45

Gly Tyr Ile Ser Tyr Asp Gly Asn Thr Tyr Tyr Asn Pro Ser Leu Lys
 50                  55                  60

Ser Arg Phe Ser Ile Thr Arg Asp Thr Ser Lys Asn Gln Tyr Tyr Leu
 65                  70                  75                  80

Gln Leu Asn Ser Val Thr Thr Glu Asp Thr Ala Thr Tyr Tyr Cys Ser
             85                  90                  95

Arg Gly Asp Tyr Gly Thr Tyr Val Met Asp Tyr Trp Gly Gln Gly Thr
                100                 105                 110

Ser Val Thr Val Ser Ser
        115

<210> SEQ ID NO 13
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: VH CDR1 of 7D12A

<400> SEQUENCE: 13

Asn Gly Tyr Trp Asn
 1               5

<210> SEQ ID NO 14
<211> LENGTH: 16
<212> TYPE: PRT
```

<213> ORGANISM: Mus musculus
<220> FEATURE:
<221> NAME/KEY: MISC_FEATURE
<222> LOCATION: (1)..(16)
<223> OTHER INFORMATION: VH CDR2 of 7D12A

<400> SEQUENCE: 14

Tyr Ile Ser Tyr Asp Gly Asn Thr Tyr Tyr Asn Pro Ser Leu Lys Ser
1               5                   10                  15

<210> SEQ ID NO 15
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: VH CDR3 of 7D12A

<400> SEQUENCE: 15

Gly Asp Tyr Gly Thr Tyr Val Met Asp Tyr
1               5                   10

<210> SEQ ID NO 16
<211> LENGTH: 333
<212> TYPE: DNA
<213> ORGANISM: Mus musculus
<220> FEATURE:
<221> NAME/KEY: CDS
<222> LOCATION: (1)..(333)
<223> OTHER INFORMATION: Coding sequence for 7D12A VL

<400> SEQUENCE: 16

```
aac att gtg ctg acc caa tct cca gtt tct ttg gct gtg tct cta ggg    48
Asn Ile Val Leu Thr Gln Ser Pro Val Ser Leu Ala Val Ser Leu Gly
1               5                   10                  15 cag agg gcc acc att tcc tgc aga gcc agt gaa agt gtt gat agt cat    96
Gln Arg Ala Thr Ile Ser Cys Arg Ala Ser Glu Ser Val Asp Ser His
            20                  25                  30 ggc aat agt ttt atg cac tgg tac cag cag aaa ccg gga cag cca ccc   144
Gly Asn Ser Phe Met His Trp Tyr Gln Gln Lys Pro Gly Gln Pro Pro
        35                  40                  45 aaa ctc ctc atc tat ctt gca tcc aac cta gag tct ggg gtc cct gcc   192
Lys Leu Leu Ile Tyr Leu Ala Ser Asn Leu Glu Ser Gly Val Pro Ala
    50                  55                  60 agg ttc act ggc ggt ggg tct ggg tca gac ttc acc ctg acc att gac   240
Arg Phe Thr Gly Gly Gly Ser Gly Ser Asp Phe Thr Leu Thr Ile Asp
65                  70                  75                  80 cct gtg gag gct gat gat gtt gga aca tat tac tgt cag caa aat aat   288
Pro Val Glu Ala Asp Asp Val Gly Thr Tyr Tyr Cys Gln Gln Asn Asn
                85                  90                  95 gag gat ccg tac acg ttc gga ggg ggg acc aag ctg gaa ata aaa       333
Glu Asp Pro Tyr Thr Phe Gly Gly Gly Thr Lys Leu Glu Ile Lys
            100                 105                 110
```

<210> SEQ ID NO 17
<211> LENGTH: 111
<212> TYPE: PRT
<213> ORGANISM: Mus musculus

<400> SEQUENCE: 17

Asn Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Ser His
            20                  25                  30

Gly Asn Ser Phe Met His Trp Tyr Gln Gln Lys Pro Gly Gln Pro
            35                  40                  45

Lys Leu Leu Ile Tyr Leu Ala Ser Asn Leu Glu Ser Gly Val Pro Ala
    50                  55                  60

Arg Phe Thr Gly Gly Ser Gly Ser Asp Phe Thr Leu Thr Ile Asp
65                  70                  75                  80

Pro Val Glu Ala Asp Asp Val Gly Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 18
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: VL CDR1 of 7D12A

<400> SEQUENCE: 18

Arg Ala Ser Glu Ser Val Asp Ser His Gly Asn Ser Phe Met His
1               5                   10                  15

<210> SEQ ID NO 19
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: VL CDR2 of 7D12A

<400> SEQUENCE: 19

Leu Ala Ser Asn Leu Glu Ser
1               5

<210> SEQ ID NO 20
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: VL CDR3 of 7D12A

<400> SEQUENCE: 20

Gln Gln Asn Asn Glu Asp Pro Tyr Thr
1               5

<210> SEQ ID NO 21
<211> LENGTH: 345
<212> TYPE: DNA
<213> ORGANISM: Mus musculus
<220> FEATURE:
<221> NAME/KEY: CDS
<222> LOCATION: (1)..(345)
<223> OTHER INFORMATION: Coding sequence for 7D1G VH

<400> SEQUENCE: 21 cag gtg cag ctg cag cag cct ggg gct gag ctg gtg aag cct ggg gcc      48
Gln Val Gln Leu Gln Gln Pro Gly Ala Glu Leu Val Lys Pro Gly Ala
1               5                   10                  15 tca gtg aag atg tcc tgc aag gct tct ggc tac aca ttt acc agt tac      96
Ser Val Lys Met Ser Cys Lys Ala Ser Gly Tyr Thr Phe Thr Ser Tyr

```
              20                  25                  30
aat ata cac tgg gta aag cag aca cct gga cag ggc ctg gaa tgg att      144
Asn Ile His Trp Val Lys Gln Thr Pro Gly Gln Gly Leu Glu Trp Ile
         35                  40                  45 gga gct gtt tct cca cga aat ggt gat act tcc tac aat cag agg ttc      192
Gly Ala Val Ser Pro Arg Asn Gly Asp Thr Ser Tyr Asn Gln Arg Phe
 50                  55                  60 aaa ggc aag gcc aca ttg act gca gac att tcc tcc agc aca gcc tac      240
Lys Gly Lys Ala Thr Leu Thr Ala Asp Ile Ser Ser Ser Thr Ala Tyr
 65                  70                  75                  80 atg cag ctc agc agc ctg aca tct gag gac tct gcg gtc tat tac tgt      288
Met Gln Leu Ser Ser Leu Thr Ser Glu Asp Ser Ala Val Tyr Tyr Cys
                 85                  90                  95 gca aga ggg tat ggt tac gac tac tgg ggc caa ggc acc act ctc aca      336
Ala Arg Gly Tyr Gly Tyr Asp Tyr Trp Gly Gln Gly Thr Thr Leu Thr
             100                 105                 110 gtc tcc tca                                                          345
Val Ser Ser
    115
```

<210> SEQ ID NO 22
<211> LENGTH: 115
<212> TYPE: PRT
<213> ORGANISM: Mus musculus

<400> SEQUENCE: 22

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
             20                  25                  30

Asn Ile His Trp Val Lys Gln Thr Pro Gly Gln Gly Leu Glu Trp Ile
         35                  40                  45

Gly Ala Val Ser Pro Arg Asn Gly Asp Thr Ser Tyr Asn Gln Arg Phe
 50                  55                  60

Lys Gly Lys Ala Thr Leu Thr Ala Asp Ile Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Tyr Gly Tyr Asp Tyr Trp Gly Gln Gly Thr Thr Leu Thr
             100                 105                 110

Val Ser Ser
    115

<210> SEQ ID NO 23
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: VH CDR1 of 7D1G

<400> SEQUENCE: 23

Ser Tyr Asn Ile His
1               5

<210> SEQ ID NO 24
<211> LENGTH: 17
<212> TYPE: PRT
<213> ORGANISM: Mus musculus
<220> FEATURE:

<221> NAME/KEY: MISC_FEATURE
<222> LOCATION: (1)..(17)
<223> OTHER INFORMATION: VH CDR2 of 7D1G

<400> SEQUENCE: 24

Ala Val Ser Pro Arg Asn Gly Asp Thr Ser Tyr Asn Gln Arg Phe Lys
1               5                   10                  15

Gly

<210> SEQ ID NO 25
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: VH CDR3 of 7D1G

<400> SEQUENCE: 25

Gly Tyr Gly Tyr Asp Tyr
1               5

<210> SEQ ID NO 26
<211> LENGTH: 321
<212> TYPE: DNA
<213> ORGANISM: Mus musculus
<220> FEATURE:
<221> NAME/KEY: CDS
<222> LOCATION: (1)..(321)
<223> OTHER INFORMATION: Coding sequence for 7D1G VL

<400> SEQUENCE: 26 gat gtt gtg cta act cag tct cca gcc acc ctg tct gtg act cca gga      48
Asp Val Val Leu Thr Gln Ser Pro Ala Thr Leu Ser Val Thr Pro Gly
1               5                   10                  15 gat aga gtc agt ctt tcc tgc agg gcc agt caa agt gtt agc aag tac      96
Asp Arg Val Ser Leu Ser Cys Arg Ala Ser Gln Ser Val Ser Lys Tyr
                20                  25                  30 cta cac tgg tat caa caa aaa tca cat gag tct cca agg ctt ctc atc     144
Leu His Trp Tyr Gln Gln Lys Ser His Glu Ser Pro Arg Leu Leu Ile
            35                  40                  45 aag tat gtt tcc cag tcc atc tct ggg atc ccc tcc agg ttc agt ggc     192
Lys Tyr Val Ser Gln Ser Ile Ser Gly Ile Pro Ser Arg Phe Ser Gly
        50                  55                  60 agt gga tca ggg aca gat ttc act ctc agt atc aac agt gtg gag act     240
Ser Gly Ser Gly Thr Asp Phe Thr Leu Ser Ile Asn Ser Val Glu Thr
65                  70                  75                  80 gaa gat ttg gga atg tat ttc tgt caa cag agt aac agc tgg cct cac     288
Glu Asp Leu Gly Met Tyr Phe Cys Gln Gln Ser Asn Ser Trp Pro His
                85                  90                  95 acg ttc ggt gct ggg acc aag ctg gag ctg aaa                         321
Thr Phe Gly Ala Gly Thr Lys Leu Glu Leu Lys
                100                 105

<210> SEQ ID NO 27
<211> LENGTH: 107
<212> TYPE: PRT
<213> ORGANISM: Mus musculus

<400> SEQUENCE: 27

Asp Val Val Leu Thr Gln Ser Pro Ala Thr Leu Ser Val Thr Pro Gly
1               5                   10                  15

Asp Arg Val Ser Leu Ser Cys Arg Ala Ser Gln Ser Val Ser Lys Tyr
                20                  25                  30

Leu His Trp Tyr Gln Gln Lys Ser His Glu Ser Pro Arg Leu Leu Ile
         35                  40                  45

Lys Tyr Val Ser Gln Ser Ile Ser Gly Ile Pro Ser Arg Phe Ser Gly
     50                  55                  60

Ser Gly Ser Gly Thr Asp Phe Thr Leu Ser Ile Asn Ser Val Glu Thr
65                  70                  75                  80

Glu Asp Leu Gly Met Tyr Phe Cys Gln Gln Ser Asn Ser Trp Pro His
                 85                  90                  95

Thr Phe Gly Ala Gly Thr Lys Leu Glu Leu Lys
            100                 105

<210> SEQ ID NO 28
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: VL CDR1 of 7D1G

<400> SEQUENCE: 28

Arg Ala Ser Gln Ser Val Ser Lys Tyr Leu His
1               5                   10

<210> SEQ ID NO 29
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: VL CDR2 of 7D1G

<400> SEQUENCE: 29

Tyr Val Ser Gln Ser Ile Ser
1               5

<210> SEQ ID NO 30
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: VL CDR3 of 7D1G

<400> SEQUENCE: 30

Gln Gln Ser Asn Ser Trp Pro His Thr
1               5

<210> SEQ ID NO 31
<211> LENGTH: 360
<212> TYPE: DNA
<213> ORGANISM: Mus musculus
<220> FEATURE:
<221> NAME/KEY: CDS
<222> LOCATION: (1)..(360)
<223> OTHER INFORMATION: Coding sequence for MAb 18V4F VH

<400> SEQUENCE: 31 cag gtg cag ctg aag gag tca gga cct ggc ctg gtg gcg ccc tca cag      48
Gln Val Gln Leu Lys Glu Ser Gly Pro Gly Leu Val Ala Pro Ser Gln
1               5                   10                  15 agc ctg tcc atc act tgc act gtc tct ggg ttt tca tta acc ggc tat      96
Ser Leu Ser Ile Thr Cys Thr Val Ser Gly Phe Ser Leu Thr Gly Tyr

```
                   20                  25                  30
ggt ata cac tgg gtt cgc cag cct cca gga aag ggt ctg gag tgg ctg      144
Gly Ile His Trp Val Arg Gln Pro Pro Gly Lys Gly Leu Glu Trp Leu
        35                  40                  45 gga gta ata tgg cct ggt gga ggc aca aat tat aat tcg gct ctc atg      192
Gly Val Ile Trp Pro Gly Gly Gly Thr Asn Tyr Asn Ser Ala Leu Met
    50                  55                  60 tcc aga ctg agc atc agc aaa gac aac tcc aag agc caa gtt ttc tta      240
Ser Arg Leu Ser Ile Ser Lys Asp Asn Ser Lys Ser Gln Val Phe Leu
65                  70                  75                  80 aaa atg aac agt ctg caa act gat gac aca gcc atg tac tac tgt gcc      288
Lys Met Asn Ser Leu Gln Thr Asp Asp Thr Ala Met Tyr Tyr Cys Ala
                85                  90                  95 aga ggt ccc ctt att act acg gaa gtt tct atg gac tac tgg ggt caa      336
Arg Gly Pro Leu Ile Thr Thr Glu Val Ser Met Asp Tyr Trp Gly Gln
            100                 105                 110 gga acc tcg gtc acc gtc tcc tca                                      360
Gly Thr Ser Val Thr Val Ser Ser
        115                 120

<210> SEQ ID NO 32
<211> LENGTH: 120
<212> TYPE: PRT
<213> ORGANISM: Mus musculus

<400> SEQUENCE: 32

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Ile His Trp Val Arg Gln Pro Pro Gly Lys Gly Leu Glu Trp Leu
        35                  40                  45

Gly Val Ile Trp Pro Gly Gly Gly Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Gly Pro Leu Ile Thr Thr Glu Val Ser Met Asp Tyr Trp Gly Gln
            100                 105                 110

Gly Thr Ser Val Thr Val Ser Ser
        115                 120

<210> SEQ ID NO 33
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: MAb 18V4F VH CDR1

<400> SEQUENCE: 33

Gly Phe Ser Leu Thr Gly Tyr
1               5

<210> SEQ ID NO 34
<211> LENGTH: 14
<212> TYPE: PRT
<213> ORGANISM: Mus musculus
<220> FEATURE:
```

```
<221> NAME/KEY: MISC_FEATURE
<222> LOCATION: (1)..(14)
<223> OTHER INFORMATION: MAb 18V4F VH CDR 2

<400> SEQUENCE: 34

Trp Pro Gly Gly Gly Thr Asn Tyr Asn Ser Ala Leu Met Ser
1               5                  10

<210> SEQ ID NO 35
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: MAb 18V4F VH CDR 3

<400> SEQUENCE: 35

Gly Pro Leu Ile Thr Thr Glu Val Ser Met Asp Tyr
1               5                  10

<210> SEQ ID NO 36
<211> LENGTH: 330
<212> TYPE: DNA
<213> ORGANISM: Mus musculus
<220> FEATURE:
<221> NAME/KEY: CDS
<222> LOCATION: (1)..(330)
<220> FEATURE:
<221> NAME/KEY: misc_feature
<222> LOCATION: (1)..(330)
<223> OTHER INFORMATION: Coding sequence for 18V4F VL

<400> SEQUENCE: 36 cag gct gtt gtg act cag gaa tct gca ctc acc aca tca cct ggt gaa      48
Gln Ala Val Val Thr Gln Glu Ser Ala Leu Thr Thr Ser Pro Gly Glu
1               5                  10                  15 aca gtc aca ctc act tgt cgc tca aat act ggg gct gtt aca act agt      96
Thr Val Thr Leu Thr Cys Arg Ser Asn Thr Gly Ala Val Thr Thr Ser
            20                  25                  30 aac tat gcc aac tgg gtc caa gaa aaa cca gat cat tta ttc act ggt     144
Asn Tyr Ala Asn Trp Val Gln Glu Lys Pro Asp His Leu Phe Thr Gly
        35                  40                  45 cta ata ggt ggt acc aac aac cga gct cca ggt gtt cct gcc aga ttc     192
Leu Ile Gly Gly Thr Asn Asn Arg Ala Pro Gly Val Pro Ala Arg Phe
    50                  55                  60 tca ggc tcc ctg att gga gac aag gct gcc ctc acc atc aca ggg gca     240
Ser Gly Ser Leu Ile Gly Asp Lys Ala Ala Leu Thr Ile Thr Gly Ala
65                  70                  75                  80 cag act gag gat gag gca ata tat ttc tgt gct cta tgg tac agc aac     288
Gln Thr Glu Asp Glu Ala Ile Tyr Phe Cys Ala Leu Trp Tyr Ser Asn
                85                  90                  95 cat tgg gtg ttc ggt gga gga acc aaa ctg act gtc cta ggc             330
His Trp Val Phe Gly Gly Gly Thr Lys Leu Thr Val Leu Gly
            100                 105                 110

<210> SEQ ID NO 37
<211> LENGTH: 110
<212> TYPE: PRT
<213> ORGANISM: Mus musculus

<400> SEQUENCE: 37

Gln Ala Val Val Thr Gln Glu Ser Ala Leu Thr Thr Ser Pro Gly Glu
1               5                  10                  15

Thr Val Thr Leu Thr Cys Arg Ser Asn Thr Gly Ala Val Thr Thr Ser
```

```
                    20                  25                  30
Asn Tyr Ala Asn Trp Val Gln Glu Lys Pro Asp His Leu Phe Thr Gly
             35                  40                  45

Leu Ile Gly Gly Thr Asn Asn Arg Ala Pro Gly Val Pro Ala Arg Phe
         50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu Gly
                100                 105                 110
```

<210> SEQ ID NO 38
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: MAb 18V4F VL CDR 1

<400> SEQUENCE: 38

```
Ser Asn Thr Gly Ala Val Thr Thr Ser Asn Tyr
 1               5                  10
```

<210> SEQ ID NO 39
<211> LENGTH: 3
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: MAb 18V4F VL CDR 2
<220> FEATURE:
<221> NAME/KEY: MISC_FEATURE

<400> SEQUENCE: 39

```
Gly Thr Asn
 1
```

<210> SEQ ID NO 40
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: MAb 18V4F VL CDR3

<400> SEQUENCE: 40

```
Trp Tyr Ser Asn His Trp
 1               5
```

<210> SEQ ID NO 41
<211> LENGTH: 360
<212> TYPE: DNA
<213> ORGANISM: Mus musculus
<220> FEATURE:
<221> NAME/KEY: CDS
<222> LOCATION: (1)..(360)
<223> OTHER INFORMATION: MAb 18P7E VH coding region

<400> SEQUENCE: 41

```
cag gtg cag ctg aag gag tca gga cct ggc ctg gtg gcg ccc tca cag    48
Gln Val Gln Leu Lys Glu Ser Gly Pro Gly Leu Val Ala Pro Ser Gln
 1               5                  10                  15
```

```
agc ctg tcc atc act tgc act gtc tct ggg ttt tca tta acc ggc tat    96
Ser Leu Ser Ile Thr Cys Thr Val Ser Gly Phe Ser Leu Thr Gly Tyr
         20                  25                  30 ggt ata cac tgg gtt cgc cag cct cca gga aag ggt ctg gag tgg ctg    144
Gly Ile His Trp Val Arg Gln Pro Pro Gly Lys Gly Leu Glu Trp Leu
     35                  40                  45 gga gta ata tgg cct ggt gga ggc aca aat tat aat tcg gct ctc atg    192
Gly Val Ile Trp Pro Gly Gly Gly Thr Asn Tyr Asn Ser Ala Leu Met
 50                  55                  60 tcc aga ctg aac atc agc aaa gac aac tcc aag agc caa gtt ttc tta    240
Ser Arg Leu Asn Ile Ser Lys Asp Asn Ser Lys Ser Gln Val Phe Leu
65                  70                  75                  80 aaa atg aac agt ctg caa act gat gac aca gcc atg tac tac tgt gcc    288
Lys Met Asn Ser Leu Gln Thr Asp Asp Thr Ala Met Tyr Tyr Cys Ala
                 85                  90                  95 aga ggt ccc ctt att act acg gaa gtt tct atg gac tac tgg ggt caa    336
Arg Gly Pro Leu Ile Thr Thr Glu Val Ser Met Asp Tyr Trp Gly Gln
             100                 105                 110 gga acc tcg gtc acc gtc tcc tca                                    360
Gly Thr Ser Val Thr Val Ser Ser
         115                 120

<210> SEQ ID NO 42
<211> LENGTH: 120
<212> TYPE: PRT
<213> ORGANISM: Mus musculus

<400> SEQUENCE: 42

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Ile His Trp Val Arg Gln Pro Pro Gly Lys Gly Leu Glu Trp Leu
        35                  40                  45

Gly Val Ile Trp Pro Gly Gly Gly Thr Asn Tyr Asn Ser Ala Leu Met
    50                  55                  60

Ser Arg Leu Asn Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Gly Pro Leu Ile Thr Thr Glu Val Ser Met Asp Tyr Trp Gly Gln
            100                 105                 110

Gly Thr Ser Val Thr Val Ser Ser
        115                 120

<210> SEQ ID NO 43
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: MAb 18P7E VH CDR1

<400> SEQUENCE: 43

Gly Phe Ser Leu Thr Gly Tyr
1               5

<210> SEQ ID NO 44
<211> LENGTH: 14
```

```
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: MAb 18P7E VH CDR2

<400> SEQUENCE: 44

Trp Pro Gly Gly Gly Thr Asn Tyr Asn Ser Ala Leu Met Ser
1               5                   10

<210> SEQ ID NO 45
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: MAb 18P7E VH CDR3

<400> SEQUENCE: 45

Gly Pro Leu Ile Thr Thr Glu Val Ser Met Asp Tyr
1               5                   10

<210> SEQ ID NO 46
<211> LENGTH: 330
<212> TYPE: DNA
<213> ORGANISM: Mus musculus
<220> FEATURE:
<221> NAME/KEY: CDS
<222> LOCATION: (1)..(330)
<223> OTHER INFORMATION: MAb 18P7E VL coding sequence

<400> SEQUENCE: 46 cag gct gtt gtg act cag gaa tct gca ctc acc aca tca cct ggt gaa      48
Gln Ala Val Val Thr Gln Glu Ser Ala Leu Thr Thr Ser Pro Gly Glu
1               5                   10                  15 aca gtc aca ctc act tgt cgc tca aat act ggg gct gtt aca act agt      96
Thr Val Thr Leu Thr Cys Arg Ser Asn Thr Gly Ala Val Thr Thr Ser
            20                  25                  30 aac tat gcc aac tgg gtc caa gaa aaa cca gat cat tta ttc act ggt     144
Asn Tyr Ala Asn Trp Val Gln Glu Lys Pro Asp His Leu Phe Thr Gly
        35                  40                  45 cta ata ggt ggt acc aac aac cga gct cca ggt gtt cct gcc aga ttc     192
Leu Ile Gly Gly Thr Asn Asn Arg Ala Pro Gly Val Pro Ala Arg Phe
    50                  55                  60 tca ggc tcc ctg att gga gac aag gct gcc ctc acc atc aca ggg gca     240
Ser Gly Ser Leu Ile Gly Asp Lys Ala Ala Leu Thr Ile Thr Gly Ala
65                  70                  75                  80 cag act gag gat gag gca ata tat ttc tgt gct cta tgg tac agc aac     288
Gln Thr Glu Asp Glu Ala Ile Tyr Phe Cys Ala Leu Trp Tyr Ser Asn
                85                  90                  95 cat tgg gtg ttc ggt gga gga acc aaa ctg act gtc cta ggc                 330
His Trp Val Phe Gly Gly Gly Thr Lys Leu Thr Val Leu Gly
            100                 105                 110

<210> SEQ ID NO 47
<211> LENGTH: 110
<212> TYPE: PRT
<213> ORGANISM: Mus musculus

<400> SEQUENCE: 47

Gln Ala Val Val Thr Gln Glu Ser Ala Leu Thr Thr Ser Pro Gly Glu
1               5                   10                  15

Thr Val Thr Leu Thr Cys Arg Ser Asn Thr Gly Ala Val Thr Thr Ser
```

```
                   20                  25                  30
Asn Tyr Ala Asn Trp Val Gln Glu Lys Pro Asp His Leu Phe Thr Gly
             35                  40                  45

Leu Ile Gly Gly Thr Asn Asn Arg Ala Pro Gly Val Pro Ala Arg Phe
         50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Gly Gly Thr Lys Leu Thr Val Leu Gly
            100                 105                 110

<210> SEQ ID NO 48
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: MAb 18P7E VL CDR1

<400> SEQUENCE: 48

Ser Asn Thr Gly Ala Val Thr Thr Ser Asn Tyr
1               5                   10

<210> SEQ ID NO 49
<211> LENGTH: 3
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: MAb 18P7E VL CDR2
<220> FEATURE:

<400> SEQUENCE: 49

Gly Thr Asn
1

<210> SEQ ID NO 50
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: MAb 18P7E VL CDR3

<400> SEQUENCE: 50

Trp Tyr Ser Asn His Trp
1               5

<210> SEQ ID NO 51
<211> LENGTH: 357
<212> TYPE: DNA
<213> ORGANISM: Artificial Sequence
<220> FEATURE:
<223> OTHER INFORMATION: Humanized version of MAb 3C12F
<220> FEATURE:
<221> NAME/KEY: CDS
<222> LOCATION: (1)..(357)
<223> OTHER INFORMATION: Humanized MAb 3C12F VH coding sequence

<400> SEQUENCE: 51 gag gtg cag ctg gtg cag tct gga gca gag gtg aaa aag ccc ggg gag      48
Glu Val Gln Leu Val Gln Ser Gly Ala Glu Val Lys Lys Pro Gly Glu
```

```
                1               5                   10                  15
tct ctg aag atc tcc tgt aag ggt tct gga ttc aac att aaa gac acc        96
Ser Leu Lys Ile Ser Cys Lys Gly Ser Gly Phe Asn Ile Lys Asp Thr
            20                  25                  30 tat ata cac tgg gtg cgc cag atg ccc ggg aaa ggc ctg gag tgg att       144
Tyr Ile His Trp Val Arg Gln Met Pro Gly Lys Gly Leu Glu Trp Ile
        35                  40                  45 ggg agg att gat cct gcg aat ggt aat act caa tat gac ccg aag ttc       192
Gly Arg Ile Asp Pro Ala Asn Gly Asn Thr Gln Tyr Asp Pro Lys Phe
    50                  55                  60 cag ggc aag gcc acc atc tca gcc gac aca tcc atc agc acc gcc tac       240
Gln Gly Lys Ala Thr Ile Ser Ala Asp Thr Ser Ile Ser Thr Ala Tyr
65                  70                  75                  80 ctg cag tgg agc agc ctg aag gcc tcg gac acc gcc atg tat tac tgt       288
Leu Gln Trp Ser Ser Leu Lys Ala Ser Asp Thr Ala Met Tyr Tyr Cys
                85                  90                  95 gcg aga agg tgg gat tac gac tat gct atg gac tac tgg ggg caa ggg       336
Ala Arg Arg Trp Asp Tyr Asp Tyr Ala Met Asp Tyr Trp Gly Gln Gly
            100                 105                 110 acc acg gtc acc gtc tcc tca                                           357
Thr Thr Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Gln Ser Gly Ala Glu Val Lys Lys Pro Gly Glu
1               5                   10                  15

Ser Leu Lys Ile Ser Cys Lys Gly Ser Gly Phe Asn Ile Lys Asp Thr
            20                  25                  30

Tyr Ile His Trp Val Arg Gln Met Pro Gly Lys Gly Leu Glu Trp Ile
        35                  40                  45

Gly Arg Ile Asp Pro Ala Asn Gly Asn Thr Gln Tyr Asp Pro Lys Phe
    50                  55                  60

Gln Gly Lys Ala Thr Ile Ser Ala Asp Thr Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Trp Asp Tyr Asp Tyr Ala Met Asp Tyr Trp Gly Gln Gly
            100                 105                 110

Thr Thr Val Thr Val Ser Ser
        115

<210> SEQ ID NO 53
<211> LENGTH: 5
<212> TYPE: PRT
<213> ORGANISM: artificial sequence
<220> FEATURE:
<223> OTHER INFORMATION: Humanized MAb 3C12F VH CDR1

<400> SEQUENCE: 53

Asp Thr Tyr Ile His
1               5

<210> SEQ ID NO 54
```

<211> LENGTH: 17
<212> TYPE: PRT
<213> ORGANISM: Artificial Sequence
<220> FEATURE:
<223> OTHER INFORMATION: Humanized MAb 3C12F VH CDR2

<400> SEQUENCE: 54

Arg Ile Asp Pro Ala Asn Gly Asn Thr Gln Tyr Asp Pro Lys Phe Gln
1               5                   10                  15
Gly

<210> SEQ ID NO 55
<211> LENGTH: 10
<212> TYPE: PRT
<213> ORGANISM: Artificial Sequence
<220> FEATURE:
<223> OTHER INFORMATION: Humanized MAb 3C12F VH CDR3

<400> SEQUENCE: 55

Arg Trp Asp Tyr Asp Tyr Ala Met Asp Tyr
1               5                   10

<210> SEQ ID NO 56
<211> LENGTH: 321
<212> TYPE: DNA
<213> ORGANISM: Artificial Sequence
<220> FEATURE:
<223> OTHER INFORMATION: Humanized MAb 3C12F VL coding sequence
<220> FEATURE:
<221> NAME/KEY: CDS
<222> LOCATION: (1)..(321)

<400> SEQUENCE: 56 gac atc cag atg acc cag tct cca tcc tcc ctg tct gca tct gta gga        48
Asp Ile Gln Met Thr Gln Ser Pro Ser Ser Leu Ser Ala Ser Val Gly
1               5                   10                  15 gac aga gtc acc atc act tgc cga ggt agt ggg aat att cac aat tat        96
Asp Arg Val Thr Ile Thr Cys Arg Gly Ser Gly Asn Ile His Asn Tyr
                20                  25                  30 tta gca tgg tat cag cag aaa cca ggg aaa gcc cct aag ctc ctg gtc       144
Leu Ala Trp Tyr Gln Gln Lys Pro Gly Lys Ala Pro Lys Leu Leu Val
        35                  40                  45 tat aat gca aaa acc tta gca gat ggg gtc cca tca agg ttc agt ggc       192
Tyr Asn Ala Lys Thr Leu Ala Asp Gly Val Pro Ser Arg Phe Ser Gly
    50                  55                  60 agt gga tct ggg aca gat tac act ctc acc atc agc agt ctg caa cct       240
Ser Gly Ser Gly Thr Asp Tyr Thr Leu Thr Ile Ser Ser Leu Gln Pro
65                  70                  75                  80 gaa gat ttt gca act tac tac tgt caa cat ttt tgg agt act ccg tac       288
Glu Asp Phe Ala Thr Tyr Tyr Cys Gln His Phe Trp Ser Thr Pro Tyr
                85                  90                  95 acg ttc ggc gga ggg acc aag gtg gag atc aaa                           321
Thr Phe Gly Gly Gly Thr Lys Val Glu Ile Lys
                100                 105

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
1               5                   10                  15

```
Asp Arg Val Thr Ile Thr Cys Arg Gly Ser Gly Asn Ile His Asn Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Thr Pro Tyr
                85                  90                  95

Thr Phe Gly Gly Gly Thr Lys Val Glu Ile Lys
            100                 105

<210> SEQ ID NO 58
<211> LENGTH: 11
<212> TYPE: PRT
<213> ORGANISM: Artificial Sequence
<220> FEATURE:
<223> OTHER INFORMATION: Humanized MAb 3C12F VL CDR1

<400> SEQUENCE: 58

Arg Gly Ser Gly Asn Ile His Asn Tyr Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Humanized MAb 3C12F VL CDR2

<400> SEQUENCE: 59

Asn Ala Lys Thr Leu Ala Asp
1               5

<210> SEQ ID NO 60
<211> LENGTH: 9
<212> TYPE: PRT
<213> ORGANISM: Artificial Sequence
<220> FEATURE:
<223> OTHER INFORMATION: Humanized MAb 3C12F VL CDR3

<400> SEQUENCE: 60

Gln His Phe Trp Ser Thr Pro Tyr Thr
1               5

<210> SEQ ID NO 61
<211> LENGTH: 360
<212> TYPE: DNA
<213> ORGANISM: Artificial Sequence
<220> FEATURE:
<223> OTHER INFORMATION: Humanized MAb 18V4F VH coding sequence
<220> FEATURE:
<221> NAME/KEY: CDS
<222> LOCATION: (1)..(360)

<400> SEQUENCE: 61 gaa gtt cag ctg gtg gaa tct ggt ggt ggt ctg gtt caa cct ggc ggc      48
Glu Val Gln Leu Val Glu Ser Gly Gly Gly Leu Val Gln Pro Gly Gly
1               5                   10                  15 tct ctg cgt ctg tcc tgc gct gcc tcc ggt ttc tct ctg acc ggc tac      96
Ser Leu Arg Leu Ser Cys Ala Ala Ser Gly Phe Ser Leu Thr Gly Tyr
            20                  25                  30
```

```
gca atg cac tgg gtt cgc cag gcc ccg ggt aaa ggc ctg gaa tgg gtt     144
Ala Met His Trp Val Arg Gln Ala Pro Gly Lys Gly Leu Glu Trp Val
        35                  40                  45 ggt gtt atc tgg ccg ggt ggc ggt act aat tac aac tcc gcg ctg atg     192
Gly Val Ile Trp Pro Gly Gly Gly Thr Asn Tyr Asn Ser Ala Leu Met
 50                  55                  60 agc cgt ttt acc atc tcc aag gac aat tcc aaa aac acc gtt tac ctg     240
Ser Arg Phe Thr Ile Ser Lys Asp Asn Ser Lys Asn Thr Val Tyr Leu
 65                  70                  75                  80 cag atg aac tcc ctg cgt gct gaa gat act gct gtg tac tac tgt gct     288
Gln Met Asn Ser Leu Arg Ala Glu Asp Thr Ala Val Tyr Tyr Cys Ala
                 85                  90                  95 cgt ggt cca ctg atc acc acc gaa gtg agc atg gac tat tgg ggc caa     336
Arg Gly Pro Leu Ile Thr Thr Glu Val Ser Met Asp Tyr Trp Gly Gln
            100                 105                 110 ggt acg ctg gtc acc gtt agc tct                                      360
Gly Thr Leu Val Thr Val Ser Ser
        115                 120

<210> SEQ ID NO 62
<211> LENGTH: 120
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Gly Tyr
            20                  25                  30

Ala Met His Trp Val Arg Gln Ala Pro Gly Lys Gly Leu Glu Trp Val
        35                  40                  45

Gly Val Ile Trp Pro Gly Gly Gly Thr Asn Tyr Asn Ser Ala Leu Met
 50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Gly Pro Leu Ile Thr Thr Glu Val Ser Met Asp Tyr Trp Gly Gln
            100                 105                 110

Gly Thr Leu Val Thr Val Ser Ser
        115                 120

<210> SEQ ID NO 63
<211> LENGTH: 7
<212> TYPE: PRT
<213> ORGANISM: Artificial Sequence
<220> FEATURE:
<223> OTHER INFORMATION: Humanized MAb 18V4F VH CDR1

<400> SEQUENCE: 63

Gly Phe Ser Leu Thr Gly Tyr
 1               5

<210> SEQ ID NO 64
<211> LENGTH: 14
<212> TYPE: PRT
<213> ORGANISM: Artificial Sequence
<220> FEATURE:
<223> OTHER INFORMATION: Humanized MAb 18V4F VH CDR2
```

<400> SEQUENCE: 64

Trp Pro Gly Gly Gly Thr Asn Tyr Asn Ser Ala Leu Met Ser
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Humanized MAb 18V4F VH CDR3

<400> SEQUENCE: 65

Gly Pro Leu Ile Thr Thr Glu Val Ser Met Asp Tyr
1               5                   10

<210> SEQ ID NO 66
<211> LENGTH: 330
<212> TYPE: DNA
<213> ORGANISM: Artificial Sequence
<220> FEATURE:
<223> OTHER INFORMATION: Humanized MAb 18V4F VL coding sequence
<220> FEATURE:
<221> NAME/KEY: CDS
<222> LOCATION: (1)..(330)
<223> OTHER INFORMATION: Humanized MAb 18V4F VL coding sequence

<400> SEQUENCE: 66

```
tct gcg gaa gtt acc cag cct ccg tct gtg agc gta tct ccg ggt cag        48
Ser Ala Glu Val Thr Gln Pro Pro Ser Val Ser Val Ser Pro Gly Gln
1               5                   10                  15 acc gcg cgc atc acg tgt tcc tct aac acg ggc gca gtt acg act agc        96
Thr Ala Arg Ile Thr Cys Ser Ser Asn Thr Gly Ala Val Thr Thr Ser
            20                  25                  30 aac tat gct aac tgg gtt caa cag aag ccg ggc cag gct ccg gtg ggt       144
Asn Tyr Ala Asn Trp Val Gln Gln Lys Pro Gly Gln Ala Pro Val Gly
        35                  40                  45 ctg att ggt ggc acg aac gag cgt ccg agc ggc att cca gaa cgt ttt       192
Leu Ile Gly Gly Thr Asn Glu Arg Pro Ser Gly Ile Pro Glu Arg Phe
    50                  55                  60 tct ggc agc tct tct ggt aac act gcg acc ctg acc atc tct ggc gct       240
Ser Gly Ser Ser Ser Gly Asn Thr Ala Thr Leu Thr Ile Ser Gly Ala
65                  70                  75                  80 cag gct gaa gac gaa gcg gat tac tac tgc gcg ctg tgg tac agc aac       288
Gln Ala Glu Asp Glu Ala Asp Tyr Tyr Cys Ala Leu Trp Tyr Ser Asn
                85                  90                  95 cac tgg gta ttc ggc ggt ggt acc aaa ctg act gtg ctg ggc                330
His Trp Val Phe Gly Gly Gly Thr Lys Leu Thr Val Leu Gly
            100                 105                 110
```

<210> SEQ ID NO 67
<211> LENGTH: 110
<212> TYPE: PRT
<213> ORGANISM: Artificial Sequence
<220> FEATURE:
<223> OTHER INFORMATION: Synthetic Construct

<400> SEQUENCE: 67

Ser Ala Glu Val Thr Gln Pro Pro Ser Val Ser Val Ser Pro Gly Gln
1               5                   10                  15

Thr Ala Arg Ile Thr Cys Ser Ser Asn Thr Gly Ala Val Thr Thr Ser
            20                  25                  30

Asn Tyr Ala Asn Trp Val Gln Gln Lys Pro Gly Gln Ala Pro Val Gly
        35                  40                  45

```
Leu Ile Gly Gly Thr Asn Glu Arg Pro Ser Gly Ile Pro Glu Arg Phe
 50                  55                  60
Ser Gly Ser Ser Ser Gly Asn Thr Ala Thr Leu Thr Ile Ser Gly Ala
 65                  70                  75                  80
Gln Ala Glu Asp Glu Ala Asp Tyr Tyr Cys Ala Leu Trp Tyr Ser Asn
                 85                  90                  95
His Trp Val Phe Gly Gly Gly Thr Lys Leu Thr Val Leu Gly
            100                 105                 110

<210> SEQ ID NO 68
<211> LENGTH: 11
<212> TYPE: PRT
<213> ORGANISM: Artificial Sequence
<220> FEATURE:
<223> OTHER INFORMATION: Humanized MAb 18V4F VL CDR1

<400> SEQUENCE: 68

Ser Asn Thr Gly Ala Val Thr Thr Ser Asn Tyr
1               5                   10

<210> SEQ ID NO 69
<211> LENGTH: 3
<212> TYPE: PRT
<213> ORGANISM: Artificial Sequence
<220> FEATURE:
<223> OTHER INFORMATION: Humanized MAb 18V4F VL CDR2

<400> SEQUENCE: 69

Gly Thr Asn
1

<210> SEQ ID NO 70
<211> LENGTH: 8
<212> TYPE: PRT
<213> ORGANISM: Artificial Sequence
<220> FEATURE:
<223> OTHER INFORMATION: Humanized MAb 18V4F VL CDR3

<400> SEQUENCE: 70

Ala Leu Trp Tyr Ser Asn His Trp
1               5

<210> SEQ ID NO 71
<211> LENGTH: 70
<212> TYPE: PRT
<213> ORGANISM: Homo sapiens
<220> FEATURE:
<221> NAME/KEY: MISC_FEATURE
<222> LOCATION: (1)..(70)
<223> OTHER INFORMATION: Human MIP1-alpha, CCL3

<400> SEQUENCE: 71

Ala Ser Leu Ala Ala Asp Thr Pro Thr Ala Cys Cys Phe Ser Tyr Thr
1               5                   10                  15

Ser Arg Gln Ile Pro Gln Asn Phe Ile Ala Asp Tyr Phe Glu Thr Ser
                20                  25                  30

Ser Gln Cys Ser Lys Pro Gly Val Ile Phe Leu Thr Lys Arg Ser Arg
            35                  40                  45

Gln Val Cys Ala Asp Pro Ser Glu Glu Trp Val Gln Lys Tyr Val Ser
        50                  55                  60

Asp Leu Glu Leu Ser Ala
 65                 70
```

```
<210> SEQ ID NO 72
<211> LENGTH: 69
<212> TYPE: PRT
<213> ORGANISM: Homo sapiens
<220> FEATURE:
<221> NAME/KEY: MISC_FEATURE
<222> LOCATION: (1)..(69)
<223> OTHER INFORMATION: Human MIP1-beta, CCL4

<400> SEQUENCE: 72

Ala Pro Met Gly Ser Asp Pro Pro Thr Ala Cys Cys Phe Ser Tyr Thr
1               5                   10                  15

Ala Arg Lys Leu Pro His Asn Phe Val Val Asp Tyr Tyr Glu Thr Ser
            20                  25                  30

Ser Leu Cys Ser Gln Pro Ala Val Val Phe Gln Thr Lys Arg Gly Lys
        35                  40                  45

Gln Val Cys Ala Asp Pro Ser Glu Ser Trp Val Gln Glu Tyr Val Tyr
    50                  55                  60

Asp Leu Glu Leu Asn
65

<210> SEQ ID NO 73
<211> LENGTH: 68
<212> TYPE: PRT
<213> ORGANISM: Homo sapiens
<220> FEATURE:
<221> NAME/KEY: MISC_FEATURE
<222> LOCATION: (1)..(68)
<223> OTHER INFORMATION: Human RANTES, CCL5

<400> SEQUENCE: 73

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 74
<211> LENGTH: 76
<212> TYPE: PRT
<213> ORGANISM: Homo sapiens
<220> FEATURE:
<221> NAME/KEY: MISC_FEATURE
<222> LOCATION: (1)..(76)
<223> OTHER INFORMATION: Human MCP-1, CCL2

<400> SEQUENCE: 74

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75
```

<210> SEQ ID NO 75
<211> LENGTH: 76
<212> TYPE: PRT
<213> ORGANISM: Homo sapiens
<220> FEATURE:
<221> NAME/KEY: MISC_FEATURE
<222> LOCATION: (1)..(76)
<223> OTHER INFORMATION: Human MCP-2, CCL8

<400> SEQUENCE: 75

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75

<210> SEQ ID NO 76
<211> LENGTH: 76
<212> TYPE: PRT
<213> ORGANISM: Homo sapiens
<220> FEATURE:
<221> NAME/KEY: MISC_FEATURE
<222> LOCATION: (1)..(76)
<223> OTHER INFORMATION: Human MCP-3, CCL7

<400> SEQUENCE: 76

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 77
<211> LENGTH: 75
<212> TYPE: PRT
<213> ORGANISM: Homo sapiens
<220> FEATURE:
<221> NAME/KEY: MISC_FEATURE
<222> LOCATION: (1)..(75)
<223> OTHER INFORMATION: Human MCP-4, CCL13

<400> SEQUENCE: 77

Gln Pro Asp Ala Leu Asn Val Pro Ser Thr Cys Cys Phe Thr Phe Ser
1               5                   10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
    50                  55                  60

```
His Leu Gly Arg Lys Ala His Thr Leu Lys Thr
 65                  70                  75

<210> SEQ ID NO 78
<211> LENGTH: 66
<212> TYPE: PRT
<213> ORGANISM: Homo sapiens
<220> FEATURE:
<221> NAME/KEY: MISC_FEATURE
<222> LOCATION: (1)..(66)
<223> OTHER INFORMATION: Human HCC-1/CCL14a

<400> SEQUENCE: 78

Gly Pro Tyr His Pro Ser Glu Cys Cys Phe Thr Tyr Thr Thr Tyr Lys
 1               5                  10                  15

Ile Pro Arg Gln Arg Ile Met Asp Tyr Tyr Glu Thr Asn Ser Gln Cys
             20                  25                  30

Ser Lys Pro Gly Ile Val Phe Ile Thr Lys Arg Gly His Ser Val Cys
         35                  40                  45

Thr Asn Pro Ser Asp Lys Trp Val Gln Asp Tyr Ile Lys Asp Met Lys
     50                  55                  60

Glu Asn
 65

<210> SEQ ID NO 79
<211> LENGTH: 68
<212> TYPE: PRT
<213> ORGANISM: Homo sapiens
<220> FEATURE:
<221> NAME/KEY: MISC_FEATURE
<222> LOCATION: (1)..(68)
<223> OTHER INFORMATION: Human HCC-2/MIP1-delta/CCL15

<400> SEQUENCE: 79

Ser Phe His Phe Ala Ala Asp Cys Cys Thr Ser Tyr Ile Ser Gln Ser
 1               5                  10                  15

Ile Pro Cys Ser Leu Met Lys Ser Tyr Phe Glu Thr Ser Ser Glu Cys
             20                  25                  30

Ser Lys Pro Gly Val Ile Phe Leu Thr Lys Lys Gly Arg Gln Val Cys
         35                  40                  45

Ala Lys Pro Ser Gly Pro Gly Val Gln Asp Cys Met Lys Lys Leu Lys
     50                  55                  60

Pro Tyr Ser Ile
 65

<210> SEQ ID NO 80
<211> LENGTH: 97
<212> TYPE: PRT
<213> ORGANISM: Homo sapiens
<220> FEATURE:
<221> NAME/KEY: MISC_FEATURE
<222> LOCATION: (1)..(97)
<223> OTHER INFORMATION: Human HCC-4, CCL16

<400> SEQUENCE: 80

Gln Pro Lys Val Pro Glu Trp Val Asn Thr Pro Ser Thr Cys Cys Leu
 1               5                  10                  15

Lys Tyr Tyr Glu Lys Val Leu Pro Arg Arg Leu Val Val Gly Tyr Arg
             20                  25                  30

Lys Ala Leu Asn Cys His Leu Pro Ala Ile Ile Phe Val Thr Lys Arg
         35                  40                  45

Asn Arg Glu Val Cys Thr Asn Pro Asn Asp Asp Trp Val Gln Glu Tyr
```

-continued

```
                    50                  55                  60
Ile Lys Asp Pro Asn Leu Pro Leu Leu Pro Thr Arg Asn Leu Ser Thr
 65                  70                  75                  80

Val Lys Ile Ile Thr Ala Lys Asn Gly Gln Pro Gln Leu Leu Asn Ser
                 85                  90                  95

Gln

<210> SEQ ID NO 81
<211> LENGTH: 75
<212> TYPE: PRT
<213> ORGANISM: Homo sapiens
<220> FEATURE:
<221> NAME/KEY: MISC_FEATURE
<222> LOCATION: (1)..(75)
<223> OTHER INFORMATION: Human MPIF-1, CCL23

<400> SEQUENCE: 81

Arg Phe His Ala Thr Ser Ala Asp Cys Cys Ile Ser Tyr Thr Pro Arg
 1               5                  10                  15

Ser Ile Pro Cys Ser Leu Leu Glu Ser Tyr Phe Glu Thr Asn Ser Glu
                20                  25                  30

Cys Ser Lys Pro Gly Val Ile Phe Leu Thr Lys Gly Arg Arg Phe
            35                  40                  45

Cys Ala Asn Pro Ser Asp Lys Gln Val Gln Val Cys Met Arg Met Leu
 50                  55                  60

Lys Leu Asp Thr Arg Ile Lys Thr Arg Lys Asn
 65                  70                  75

<210> SEQ ID NO 82
<211> LENGTH: 69
<212> TYPE: PRT
<213> ORGANISM: Homo sapiens
<220> FEATURE:
<221> NAME/KEY: MISC_FEATURE
<222> LOCATION: (1)..(69)
<223> OTHER INFORMATION: Human PARC, CCL18

<400> SEQUENCE: 82

Ala Gln Val Gly Thr Asn Lys Glu Leu Cys Cys Leu Val Tyr Thr Ser
 1               5                  10                  15

Trp Gln Ile Pro Gln Lys Phe Ile Val Asp Tyr Ser Glu Thr Ser Pro
                20                  25                  30

Gln Cys Pro Lys Pro Gly Val Ile Leu Leu Thr Lys Arg Gly Arg Gln
            35                  40                  45

Ile Cys Ala Asp Pro Asn Lys Lys Trp Val Gln Lys Tyr Ile Ser Asp
 50                  55                  60

Leu Lys Leu Asn Ala
 65

<210> SEQ ID NO 83
<211> LENGTH: 74
<212> TYPE: PRT
<213> ORGANISM: Homo sapiens

<400> SEQUENCE: 83

Gly Pro Ala Ser Val Pro Thr Thr Cys Cys Phe Asn Leu Ala Asn Arg
 1               5                  10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
```

```
                35                  40                  45
Ile Cys Ala Asp Pro Lys Lys Lys Trp Val Gln Asp Ser Met Lys Tyr
 50                  55                  60

Leu Asp Gln Lys Ser Pro Thr Pro Lys Pro
 65                  70
```

<210> SEQ ID NO 84
<211> LENGTH: 93
<212> TYPE: PRT
<213> ORGANISM: Homo sapiens

<400> SEQUENCE: 84

```
Val Val Ile Pro Ser Pro Cys Cys Met Phe Phe Val Ser Lys Arg Ile
  1               5                  10                  15

Pro Glu Asn Arg Val Val Ser Tyr Gln Leu Ser Ser Arg Ser Thr Cys
                 20                  25                  30

Leu Lys Gly Gly Val Ile Phe Thr Thr Lys Lys Gly Gln Gln Phe Cys
             35                  40                  45

Gly Asp Pro Lys Gln Glu Trp Val Gln Arg Tyr Met Lys Asn Leu Asp
 50                  55                  60

Ala Lys Gln Lys Lys Ala Ser Pro Arg Ala Arg Ala Val Ala Val Lys
 65                  70                  75                  80

Gly Pro Val Gln Arg Tyr Pro Gly Asn Gln Thr Thr Cys
                 85                  90
```

<210> SEQ ID NO 85
<211> LENGTH: 71
<212> TYPE: PRT
<213> ORGANISM: Homo sapiens

<400> SEQUENCE: 85

```
Thr Arg Gly Ser Asp Ile Ser Lys Thr Cys Cys Phe Gln Tyr Ser His
  1               5                  10                  15

Lys Pro Leu Pro Trp Thr Trp Val Arg Ser Tyr Glu Phe Thr Ser Asn
                 20                  25                  30

Ser Cys Ser Gln Arg Ala Val Ile Phe Thr Thr Lys Arg Gly Lys Lys
             35                  40                  45

Val Cys Thr His Pro Arg Lys Lys Trp Val Gln Lys Tyr Ile Ser Leu
 50                  55                  60

Leu Lys Thr Pro Lys Gln Leu
 65                  70
```

<210> SEQ ID NO 86
<211> LENGTH: 69
<212> TYPE: PRT
<213> ORGANISM: Homo sapiens

<400> SEQUENCE: 86

```
Gly Pro Tyr Gly Ala Asn Met Glu Asp Ser Val Cys Cys Arg Asp Tyr
  1               5                  10                  15

Val Arg Tyr Arg Leu Pro Leu Arg Val Val Lys His Phe Tyr Trp Thr
                 20                  25                  30

Ser Asp Ser Cys Pro Arg Pro Gly Val Val Leu Leu Thr Phe Arg Asp
             35                  40                  45

Lys Glu Ile Cys Ala Asp Pro Arg Val Pro Trp Val Lys Met Ile Leu
 50                  55                  60

Asn Lys Leu Ser Gln
 65
```

<210> SEQ ID NO 87
<211> LENGTH: 71
<212> TYPE: PRT
<213> ORGANISM: Homo sapiens

<400> SEQUENCE: 87

Ala Arg Gly Thr Asn Val Gly Arg Glu Cys Cys Leu Glu Tyr Phe Lys
1               5                   10                  15

Gly Ala Ile Pro Leu Arg Lys Leu Lys Thr Trp Tyr Gln Thr Ser Glu
            20                  25                  30

Asp Cys Ser Arg Asp Ala Ile Val Phe Val Thr Val Gln Gly Arg Ala
        35                  40                  45

Ile Cys Ser Asp Pro Asn Asn Lys Arg Val Lys Asn Ala Val Lys Tyr
    50                  55                  60

Leu Gln Ser Leu Glu Arg Ser
65                  70

<210> SEQ ID NO 88
<211> LENGTH: 70
<212> TYPE: PRT
<213> ORGANISM: Homo sapiens

<400> SEQUENCE: 88

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
65                  70

<210> SEQ ID NO 89
<211> LENGTH: 77
<212> TYPE: PRT
<213> ORGANISM: Homo sapiens

<400> SEQUENCE: 89

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
    50                  55                  60

Leu Gln Arg Thr Ser Ala Lys Met Lys Arg Arg Ser Ser
65                  70                  75

<210> SEQ ID NO 90
<211> LENGTH: 111
<212> TYPE: PRT
<213> ORGANISM: Homo sapiens

<400> SEQUENCE: 90

Ser Asp Gly Gly Ala Gln Asp Cys Cys Leu Lys Tyr Ser Gln Arg Lys

```
                1               5                   10                  15
            Ile Pro Ala Lys Val Val Arg Ser Tyr Arg Lys Gln Glu Pro Ser Leu
                            20                  25                  30

Gly Cys Ser Ile Pro Ala Ile Leu Phe Leu Pro Arg Lys Arg Ser Gln
                            35                  40                  45

Ala Glu Leu Cys Ala Asp Pro Lys Glu Leu Trp Val Gln Gln Leu Met
                50                      55                  60

Gln His Leu Asp Lys Thr Pro Ser Pro Gln Lys Pro Ala Gln Gly Cys
            65                      70                  75                  80

Arg Lys Asp Arg Gly Ala Ser Lys Thr Gly Lys Gly Lys Gly Ser
                                85                  90                  95

Lys Gly Cys Lys Arg Thr Glu Arg Ser Gln Thr Pro Lys Gly Pro
                            100                 105                 110

<210> SEQ ID NO 91
<211> LENGTH: 73
<212> TYPE: PRT
<213> ORGANISM: Homo sapiens

<400> SEQUENCE: 91

Lys Ser Met Gln Val Pro Phe Ser Arg Cys Cys Phe Ser Phe Ala Glu
1               5                   10                  15

Gln Glu Ile Pro Leu Arg Ala Ile Leu Cys Tyr Arg Asn Thr Ser Ser
                20                  25                  30

Ile Cys Ser Asn Glu Gly Leu Ile Phe Lys Leu Lys Arg Gly Lys Glu
            35                  40                  45

Ala Cys Ala Leu Asp Thr Val Gly Trp Val Gln Arg His Arg Lys Met
    50                      55                  60

Leu Arg His Cys Pro Ser Lys Arg Lys
65                      70

<210> SEQ ID NO 92
<211> LENGTH: 127
<212> TYPE: PRT
<213> ORGANISM: Homo sapiens

<400> SEQUENCE: 92

Gln Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
                20                  25                  30

Gly Ser Cys Asn Leu Pro Ala Ala Ile Phe Tyr Leu Pro Lys Arg His
            35                  40                  45

Arg Lys Val Cys Gly Asn Pro Lys Ser Arg Glu Val Gln Arg Ala Met
    50                      55                  60

Lys Leu Leu Asp Ala Arg Asn Lys Val Phe Ala Lys Leu His His Asn
65                      70                  75                  80

Met Gln Thr Phe Gln Ala Gly Pro His Ala Val Lys Lys Leu Ser Ser
                85                  90                  95

Gly Asn Ser Lys Leu Ser Ser Ser Lys Phe Ser Asn Pro Ile Ser Ser
                100                 105                 110

Ser Lys Arg Asn Val Ser Leu Leu Ile Ser Ala Asn Ser Gly Leu
                115                 120                 125

<210> SEQ ID NO 93
<211> LENGTH: 88
<212> TYPE: PRT
```

<213> ORGANISM: Homo sapiens

<400> SEQUENCE: 93

Phe Leu Leu Pro Pro Ser Thr Ala Cys Cys Thr Gln Leu Tyr Arg Lys
1               5                   10                  15

Pro Leu Ser Asp Lys Leu Leu Arg Lys Val Ile Gln Val Glu Leu Gln
            20                  25                  30

Glu Ala Asp Gly Asp Cys His Leu Gln Ala Phe Val Leu His Leu Ala
        35                  40                  45

Gln Arg Ser Ile Cys Ile His Pro Gln Asn Pro Ser Leu Ser Gln Trp
    50                  55                  60

Phe Glu His Gln Glu Arg Lys Leu His Gly Thr Leu Pro Lys Leu Asn
65                  70                  75                  80

Phe Gly Met Leu Arg Lys Met Gly
                85

<210> SEQ ID NO 94
<211> LENGTH: 105
<212> TYPE: PRT
<213> ORGANISM: Homo sapiens

<400> SEQUENCE: 94

Ile Leu Pro Ile Ala Ser Ser Cys Cys Thr Glu Val Ser His His Ile
1               5                   10                  15

Ser Arg Arg Leu Leu Glu Arg Val Asn Met Cys Arg Ile Gln Arg Ala
            20                  25                  30

Asp Gly Asp Cys Asp Leu Ala Ala Val Ile Leu His Val Lys Arg Arg
        35                  40                  45

Arg Ile Cys Val Ser Pro His Asn His Thr Val Lys Gln Trp Met Lys
    50                  55                  60

Val Gln Ala Ala Lys Lys Asn Gly Lys Gly Asn Val Cys His Arg Lys
65                  70                  75                  80

Lys His His Gly Lys Arg Asn Ser Asn Arg Ala His Gln Gly Lys His
                85                  90                  95

Glu Thr Tyr Gly His Lys Thr Pro Tyr
            100                 105

<210> SEQ ID NO 95
<211> LENGTH: 94
<212> TYPE: PRT
<213> ORGANISM: Homo sapiens

<400> SEQUENCE: 95

Met Val Gly Ser Glu Val Ser Asp Lys Arg Thr Cys Val Ser Leu Thr
1               5                   10                  15

Thr Gln Arg Leu Pro Val Ser Arg Ile Lys Thr Tyr Thr Ile Thr Glu
            20                  25                  30

Gly Ser Leu Arg Ala Val Ile Phe Ile Thr Lys Arg Gly Leu Lys Val
        35                  40                  45

Cys Ala Asp Pro Gln Ala Thr Trp Val Arg Asp Val Val Arg Ser Met
    50                  55                  60

Asp Arg Lys Ser Asn Thr Arg Asn Asn Met Ile Gln Thr Lys Pro Thr
65                  70                  75                  80

Gly Thr Gln Gln Ser Thr Asn Thr Ala Val Thr Leu Thr Gly
                85                  90

<210> SEQ ID NO 96

```
<211> LENGTH: 339
<212> TYPE: PRT
<213> ORGANISM: Homo sapiens

<400> SEQUENCE: 96

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Met Gly Pro Val Pro Ala His Thr
            260                 265                 270

Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg

<210> SEQ ID NO 97
<211> LENGTH: 72
<212> TYPE: PRT
<213> ORGANISM: Homo sapiens

<400> SEQUENCE: 97
```

```
Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65              70

<210> SEQ ID NO 98
<211> LENGTH: 73
<212> TYPE: PRT
<213> ORGANISM: Homo sapiens

<400> SEQUENCE: 98

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
        35                  40                  45

Lys Ala Cys Leu Asn Pro Ala Ser Pro Ile Val Lys Lys Ile Ile Glu
    50                  55                  60

Lys Met Leu Asn Ser Asp Lys Ser Asn
65              70

<210> SEQ ID NO 99
<211> LENGTH: 73
<212> TYPE: PRT
<213> ORGANISM: Homo sapiens

<400> SEQUENCE: 99

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
            20                  25                  30

Pro His Cys Ala Gln Thr Glu Val Ile Ala Thr Leu Lys Asn Gly Gln
        35                  40                  45

Lys Ala Cys Leu Asn Pro Ala Ser Pro Met Val Lys Lys Ile Ile Glu
    50                  55                  60

Lys Met Leu Lys Asn Gly Lys Ser Asn
65              70

<210> SEQ ID NO 100
<211> LENGTH: 73
<212> TYPE: PRT
<213> ORGANISM: Homo sapiens

<400> SEQUENCE: 100

Ala Ser Val Val Thr Glu Leu Arg Cys Gln Cys Leu Gln Thr Leu Gln
1               5                   10                  15

Gly Ile His Leu Lys Asn Ile Gln Ser Val Asn Val Arg Ser Pro Gly
            20                  25                  30

Pro His Cys Ala Gln Thr Glu Val Ile Ala Thr Leu Lys Asn Gly Lys
        35                  40                  45

Lys Ala Cys Leu Asn Pro Ala Ser Pro Met Val Gln Lys Ile Ile Glu
```

```
                    50                  55                  60

Lys Ile Leu Asn Lys Gly Ser Thr Asn
 65                  70

<210> SEQ ID NO 101
<211> LENGTH: 78
<212> TYPE: PRT
<213> ORGANISM: Homo sapiens

<400> SEQUENCE: 101

Ala Gly Pro Ala Ala Val Leu Arg Glu Leu Arg Cys Val Cys Leu
 1               5                  10                  15

Gln Thr Thr Gln Gly Val His Pro Lys Met Ile Ser Asn Leu Gln Val
                20                  25                  30

Phe Ala Ile Gly Pro Gln Cys Ser Lys Val Glu Val Val Ala Ser Leu
            35                  40                  45

Lys Asn Gly Lys Glu Ile Cys Leu Asp Pro Glu Ala Pro Phe Leu Lys
        50                  55                  60

Lys Val Ile Gln Lys Ile Leu Asp Gly Gly Asn Lys Glu Asn
 65                  70                  75

<210> SEQ ID NO 102
<211> LENGTH: 75
<212> TYPE: PRT
<213> ORGANISM: Homo sapiens

<400> SEQUENCE: 102

Val Ser Ala Val Leu Thr Glu Leu Arg Cys Thr Cys Leu Arg Val Thr
 1               5                  10                  15

Leu Arg Val Asn Pro Lys Thr Ile Gly Lys Leu Gln Val Phe Pro Ala
                20                  25                  30

Gly Pro Gln Cys Ser Lys Val Glu Val Val Ala Ser Leu Lys Asn Gly
            35                  40                  45

Lys Gln Val Cys Leu Asp Pro Glu Ala Pro Phe Leu Lys Lys Val Ile
        50                  55                  60

Gln Lys Ile Leu Asp Ser Gly Asn Lys Lys Asn
 65                  70                  75

<210> SEQ ID NO 103
<211> LENGTH: 70
<212> TYPE: PRT
<213> ORGANISM: Homo sapiens

<400> SEQUENCE: 103

Ala Glu Leu Arg Cys Met Cys Ile Lys Thr Thr Ser Gly Ile His Pro
 1               5                  10                  15

Lys Asn Ile Gln Ser Leu Glu Val Ile Gly Lys Gly Thr His Cys Asn
                20                  25                  30

Gln Val Glu Val Ile Ala Thr Leu Lys Asp Gly Arg Lys Ile Cys Leu
            35                  40                  45

Asp Pro Asp Ala Pro Arg Ile Lys Lys Ile Val Gln Lys Lys Leu Ala
        50                  55                  60

Gly Asp Glu Ser Ala Asp
 65                  70

<210> SEQ ID NO 104
<211> LENGTH: 70
<212> TYPE: PRT
<213> ORGANISM: Homo sapiens
```

-continued

<400> SEQUENCE: 104

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70

<210> SEQ ID NO 105
<211> LENGTH: 78
<212> TYPE: PRT
<213> ORGANISM: Homo sapiens

<400> SEQUENCE: 105

Met Val Pro Leu Ser Arg Thr Val Arg Cys Thr Cys Ile Ser Ile Ser
1               5                   10                  15

Asn Gln Pro Val Asn Pro Arg Ser Leu Glu Lys Leu Glu Ile Ile Pro
            20                  25                  30

Ala Ser Gln Phe Cys Pro Arg Val Glu Ile Ile Ala Thr Met Lys Lys
        35                  40                  45

Lys Gly Glu Lys Arg Cys Leu Asn Pro Glu Ser Lys Ala Ile Lys Asn
    50                  55                  60

Leu Leu Lys Ala Val Ser Lys Glu Arg Ser Lys Arg Ser Pro
65                  70                  75

<210> SEQ ID NO 106
<211> LENGTH: 103
<212> TYPE: PRT
<213> ORGANISM: Homo sapiens

<400> SEQUENCE: 106

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
            20                  25                  30

Ser Pro Ser Cys Glu Lys Ile Glu Ile Ile Ala Thr Leu Lys Asn Gly
        35                  40                  45

Val Gln Thr Cys Leu Asn Pro Asp Ser Ala Asp Val Lys Glu Leu Ile
    50                  55                  60

Lys Lys Thr Glu Lys Gln Val Ser Gln Lys Lys Gln Lys Asn Gly
65                  70                  75                  80

Lys Lys His Gln Lys Lys Lys Val Leu Lys Val Arg Lys Ser Gln Arg
            85                  90                  95

Ser Arg Gln Lys Lys Thr Thr
            100

<210> SEQ ID NO 107
<211> LENGTH: 73
<212> TYPE: PRT
<213> ORGANISM: Homo sapiens

<400> SEQUENCE: 107

Phe Pro Met Phe Lys Arg Gly Arg Cys Leu Cys Ile Gly Pro Gly Val

```
                1               5                   10                  15
Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
                35                  40                  45

Lys Gly Gln Arg Cys Leu Asn Pro Lys Ser Lys Gln Ala Arg Leu Ile
50                  55                  60

Ile Lys Lys Val Glu Arg Lys Asn Phe
65                  70

<210> SEQ ID NO 108
<211> LENGTH: 68
<212> TYPE: PRT
<213> ORGANISM: Homo sapiens

<400> SEQUENCE: 108

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
                35                  40                  45

Val Cys Ile Asp Pro Lys Leu Lys Trp Ile Gln Glu Tyr Leu Glu Lys
50                  55                  60

Ala Leu Asn Lys
65

<210> SEQ ID NO 109
<211> LENGTH: 87
<212> TYPE: PRT
<213> ORGANISM: Homo sapiens

<400> SEQUENCE: 109

Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
                20                  25                  30

Pro Arg Gly Asn Gly Cys Pro Arg Lys Glu Ile Ile Val Trp Lys Lys
                35                  40                  45

Asn Lys Ser Ile Val Cys Val Asp Pro Gln Ala Glu Trp Ile Gln Arg
                50                  55                  60

Met Met Glu Val Leu Arg Lys Arg Ser Ser Ser Thr Leu Pro Val Pro
65                  70                  75                  80

Val Phe Lys Arg Lys Ile Pro
                85

<210> SEQ ID NO 110
<211> LENGTH: 89
<212> TYPE: PRT
<213> ORGANISM: Homo sapiens

<400> SEQUENCE: 110

Asn Glu Gly Ser Val Thr Gly Ser Cys Tyr Cys Gly Lys Arg Ile Ser
1               5                   10                  15

Ser Asp Ser Pro Pro Ser Val Gln Phe Met Asn Arg Leu Arg Lys His
                20                  25                  30

Leu Arg Ala Tyr His Arg Cys Leu Tyr Tyr Thr Arg Phe Gln Leu Leu
                35                  40                  45
```

Ser Trp Ser Val Cys Gly Gly Asn Lys Asp Pro Trp Val Gln Glu Leu
    50                  55                  60

Met Ser Cys Leu Asp Leu Lys Glu Cys Gly His Ala Tyr Ser Gly Ile
65                  70                  75                  80

Val Ala His Gln Lys His Leu Leu Pro
                85

<210> SEQ ID NO 111
<211> LENGTH: 77
<212> TYPE: PRT
<213> ORGANISM: Homo sapiens

<400> SEQUENCE: 111

Ser Lys Cys Lys Cys Ser Arg Lys Gly Pro Lys Ile Arg Tyr Ser Asp
1               5                   10                  15

Val Lys Lys Leu Glu Met Lys Pro Lys Tyr Pro His Cys Glu Glu Lys
                20                  25                  30

Met Val Ile Ile Thr Thr Lys Ser Val Ser Arg Tyr Arg Gly Gln Glu
            35                  40                  45

His Cys Leu His Pro Lys Leu Gln Ser Thr Lys Arg Phe Ile Lys Trp
    50                  55                  60

Tyr Asn Ala Trp Asn Glu Lys Arg Arg Val Tyr Glu Glu
65                  70                  75

<210> SEQ ID NO 112
<211> LENGTH: 69
<212> TYPE: PRT
<213> ORGANISM: Mus musculus
<220> FEATURE:
<221> NAME/KEY: MISC_FEATURE
<222> LOCATION: (1)..(69)
<223> OTHER INFORMATION: Murine MIP-1alpha, CCL3

<400> SEQUENCE: 112

Ala Pro Tyr Gly Ala Asp Thr Pro Thr Ala Cys Cys Phe Ser Tyr Ser
1               5                   10                  15

Arg Lys Ile Pro Arg Gln Phe Ile Val Asp Tyr Phe Glu Thr Ser Ser
                20                  25                  30

Leu Cys Ser Gln Pro Gly Val Ile Phe Leu Thr Lys Arg Asn Arg Gln
            35                  40                  45

Ile Cys Ala Asp Ser Lys Glu Thr Trp Val Gln Glu Tyr Ile Thr Asp
    50                  55                  60

Leu Glu Leu Asn Ala
65

<210> SEQ ID NO 113
<211> LENGTH: 69
<212> TYPE: PRT
<213> ORGANISM: Mus musculus
<220> FEATURE:
<221> NAME/KEY: MISC_FEATURE
<222> LOCATION: (1)..(69)
<223> OTHER INFORMATION: Murine MIP-1beta, CCL4

<400> SEQUENCE: 113

Ala Pro Met Gly Ser Asp Pro Thr Ser Cys Cys Phe Ser Tyr Thr
1               5                   10                  15

Ser Arg Gln Leu His Arg Ser Phe Val Met Asp Tyr Tyr Glu Thr Ser
                20                  25                  30

Ser Leu Cys Ser Lys Pro Ala Val Val Phe Leu Thr Lys Arg Gly Arg

```
                    35                  40                  45

Gln Ile Cys Ala Asn Pro Ser Glu Pro Trp Val Thr Glu Tyr Met Ser
        50                  55                  60

Asp Leu Glu Leu Asn
65

<210> SEQ ID NO 114
<211> LENGTH: 68
<212> TYPE: PRT
<213> ORGANISM: Mus musculus
<220> FEATURE:
<221> NAME/KEY: MISC_FEATURE
<222> LOCATION: (1)..(68)
<223> OTHER INFORMATION: Murine RANTES, CCL5

<400> SEQUENCE: 114

Ser Pro Tyr Gly Ser Asp Thr Thr Pro Cys Cys Phe Ala Tyr Leu Ser
1               5                   10                  15

Leu Ala Leu Pro Arg Ala His Val Lys Glu Tyr Phe Tyr Thr Ser Ser
            20                  25                  30

Lys Cys Ser Asn Leu Ala Val Val Phe Val Thr Arg Arg Asn Arg Gln
        35                  40                  45

Val Cys Ala Asn Pro Glu Lys Lys Trp Val Gln Glu Tyr Ile Asn Tyr
    50                  55                  60

Leu Glu Met Ser
65

<210> SEQ ID NO 115
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: Murine MCP-1, CCL2

<400> SEQUENCE: 115

Gln Pro Asp Ala Val Asn Ala Pro Leu Thr Cys Cys Tyr Ser Phe Thr
1               5                   10                  15

Ser Lys Met Ile Pro Met Ser Arg Leu Glu Ser Tyr Lys Arg Ile Thr
            20                  25                  30

Ser Ser Arg Cys Pro Lys Glu Ala Val Val Phe Val Thr Lys Leu Lys
        35                  40                  45

Arg Glu Val Cys Ala Asp Pro Lys Lys Glu Trp Val Gln Thr Tyr Ile
    50                  55                  60

Lys Asn Leu Asp Arg Asn Gln Met Arg Ser Glu Pro Thr Thr Leu Phe
65                  70                  75                  80

Lys Thr Ala Ser Ala Leu Arg Ser Ser Ala Pro Leu Asn Val Lys Leu
                85                  90                  95

Thr Arg Lys Ser Glu Ala Asn Ala Ser Thr Thr Phe Ser Thr Thr Thr
            100                 105                 110

Ser Ser Thr Ser Val Gly Val Thr Ser Val Thr Val Asn
        115                 120                 125

<210> SEQ ID NO 116
<211> LENGTH: 82
<212> TYPE: PRT
<213> ORGANISM: Mus musculus
<220> FEATURE:
<221> NAME/KEY: MISC_FEATURE
<222> LOCATION: (1)..(82)
```

-continued

<223> OTHER INFORMATION: Murine MCP-5, CCL12

<400> SEQUENCE: 116

```
Gly Pro Asp Ala Val Ser Thr Pro Val Thr Cys Cys Tyr Asn Val Val
1               5                   10                  15

Lys Gln Lys Ile His Val Arg Lys Leu Lys Ser Tyr Arg Arg Ile Thr
            20                  25                  30

Ser Ser Gln Cys Pro Arg Glu Ala Val Ile Phe Arg Thr Ile Leu Asp
        35                  40                  45

Lys Glu Ile Cys Ala Asp Pro Lys Glu Lys Trp Val Lys Asn Ser Ile
    50                  55                  60

Asn His Leu Asp Lys Thr Ser Gln Thr Phe Ile Leu Glu Pro Ser Cys
65                  70                  75                  80

Leu Gly
```

<210> SEQ ID NO 117
<211> LENGTH: 246
<212> TYPE: PRT
<213> ORGANISM: Cowpox virus

<400> SEQUENCE: 117

```
Met Lys Gln Ile Val Leu Ala Cys Ile Cys Leu Ala Ala Val Ala Ile
1               5                   10                  15

Pro Thr Ser Leu Gln Gln Ser Phe Ser Ser Ser Ser Ser Cys Thr Glu
            20                  25                  30

Glu Glu Asn Lys His His Met Gly Ile Asp Val Ile Ile Lys Val Thr
        35                  40                  45

Lys Gln Asp Gln Thr Pro Thr Asn Asp Lys Ile Cys Gln Ser Val Thr
    50                  55                  60

Glu Val Thr Glu Ser Glu Asp Glu Ser Glu Glu Val Val Lys Gly Asp
65                  70                  75                  80

Pro Thr Thr Tyr Tyr Thr Val Val Gly Gly Gly Leu Thr Met Asp Phe
                85                  90                  95

Gly Phe Thr Lys Cys Pro Lys Ile Ser Ser Ile Ser Glu Tyr Ser Asp
            100                 105                 110

Gly Asn Thr Val Asn Ala Arg Leu Ser Ser Val Ser Pro Gly Gln Gly
        115                 120                 125

Lys Asp Ser Pro Ala Ile Thr Arg Glu Glu Ala Leu Ser Met Ile Lys
    130                 135                 140

Asp Cys Glu Met Ser Ile Asn Ile Lys Cys Ser Glu Glu Glu Lys Asp
145                 150                 155                 160

Ser Asn Ile Lys Thr His Pro Val Leu Gly Ser Asn Ile Ser His Lys
                165                 170                 175

Lys Val Ser Tyr Glu Asp Ile Ile Gly Ser Thr Ile Val Asp Thr Lys
            180                 185                 190

Cys Val Lys Asn Leu Glu Ile Ser Val Arg Ile Gly Asp Met Cys Lys
        195                 200                 205

Glu Ser Ser Glu Leu Glu Val Lys Asp Gly Phe Lys Tyr Val Asp Gly
    210                 215                 220

Ser Ala Ser Glu Asp Ala Ala Asp Asp Thr Ser Leu Ile Asn Ser Ala
225                 230                 235                 240

Lys Leu Ile Ala Cys Val
                245
```

The invention claimed is:

1. An isolated antibody or antigen binding fragment thereof that binds to at least CCL3/MIP-1α, CCL4/MIP-1β, and CCL4/RANTES chemokines, wherein the antibody comprises the three heavy chain CDRs (HCDR1, HCDR2, and HCDR3) contained within the heavy chain variable region sequence selected from SEQ ID NOS:2, 12, 22, 32, 42, 52, or 62.

2. The isolated or purified monoclonal antibody of claim 1 that is a chimeric monoclonal antibody or an antigen binding fragment thereof.

3. The isolated or purified monoclonal antibody of claim 1 that is a humanized monoclonal antibody or an antigen binding fragment thereof.

4. The isolated or purified monoclonal antibody of claim 1 that is a full-length monoclonal antibody.

5. An antigen binding fragment of the isolated or purified monoclonal antibody of claim 1.

6. The fragment of claim 5 that is an Fab' or F(ab')2.

7. The monoclonal antibody or fragment thereof of claim 1 that has been conjugated to an effector moiety, targeting moiety, heterologous protein, toxin, enzyme, cytokine, chemical tag, radiological tag, a substance that increases its biological half-life or a substance that increases its biological availability.

8. A composition comprising (i) the isolated or purified monoclonal antibody or the fragment thereof of claim 1 and (ii) a carrier or excipient.

9. The isolated antibody or antigen binding fragment thereof of claim 1, wherein the antibody comprises a heavy chain variable region comprising the HCDR1 sequence of SEQ ID NO:13, the HCDR2 sequence of SEQ ID NO:14, and the HCDR3 sequence of SEQ ID NO:15 and a light chain variable region comprising the LCDR1 sequence of SEQ ID NO:18, the LCDR2 sequence of SEQ ID NO:19, and the LCDR3 sequence of SEQ ID NO:20.

10. The isolated antibody or antigen binding fragment thereof of claim 1, wherein the antibody comprises a heavy chain variable region comprising the HCDR1 sequence of SEQ ID NO:23, the HCDR2 sequence of SEQ ID NO:24, and the HCDR3 sequence of SEQ ID NO:25 and a light chain variable region comprising the LCDR1 sequence of SEQ ID NO:28, the LCDR2 sequence of SEQ ID NO:29, and the LCDR3 sequence of SEQ ID NO:30.

11. The isolated antibody or antigen binding fragment thereof of claim 1, wherein the antibody comprises a heavy chain variable region comprising the HCDR1 sequence of SEQ ID NO:43, the HCDR2 sequence of SEQ ID NO:44, and the HCDR3 sequence of SEQ ID NO:45 and a light chain variable region comprising the LCDR1 sequence of SEQ ID NO:48, the LCDR2 sequence of SEQ ID NO:49, and the LCDR3 sequence of SEQ ID NO:50.

12. The isolated antibody or antigen binding fragment thereof of claim 3, wherein the antibody comprises a heavy chain variable region comprising the HCDR1 sequence of SEQ ID NO:53, the HCDR2 sequence of SEQ ID NO:54, and the HCDR3 sequence of SEQ ID NO:55 and a light chain variable region comprising the LCDR1 sequence of SEQ ID NO:58, the LCDR2 sequence of SEQ ID NO:59, and the LCDR3 sequence of SEQ ID NO:60.

13. The isolated antibody or antigen binding fragment thereof of claim 3, wherein the antibody comprises a heavy chain variable region comprising the HCDR1 sequence of SEQ ID NO:63, the HCDR2 sequence of SEQ ID NO:64, and the HCDR3 sequence of SEQ ID NO:65 and a light chain variable region comprising the LCDR1 sequence of SEQ ID NO:68, the LCDR2 sequence of SEQ ID NO:69, and the LCDR3 sequence of SEQ ID NO:70.

14. The isolated antibody or antigen binding fragment thereof of claim 1, wherein the antibody comprises a heavy chain variable region sequence comprising SEQ ID NO:2 and a light chain variable region sequence comprising SEQ ID NO:7.

15. The isolated antibody or antigen binding fragment thereof of claim 1, wherein the antibody comprises a heavy chain variable region sequence comprising SEQ ID NO:12 and a light chain variable region sequence comprising SEQ ID NO:17.

16. The isolated antibody or antigen binding fragment thereof of claim 1, wherein the antibody comprises a heavy chain variable region sequence comprising SEQ ID NO:22 and a light chain variable region sequence comprising SEQ ID NO:27.

17. The isolated antibody or antigen binding fragment thereof of claim 1, wherein the antibody comprises a heavy chain variable region sequence comprising SEQ ID NO:42 and a light chain variable region sequence comprising SEQ ID NO:47.

18. The isolated antibody or antigen binding fragment thereof of claim 3, wherein the antibody comprises a heavy chain variable region sequence comprising SEQ ID NO:52 and a light chain variable region sequence comprising SEQ ID NO:57.

19. The isolated antibody or antigen binding fragment thereof of claim 3, wherein the antibody comprises a heavy chain variable region sequence comprising SEQ ID NO:62 and a light chain variable region sequence comprising SEQ ID NO:67.

* * * * *